(12) United States Patent
Brown et al.

(10) Patent No.: US 12,168,799 B2
(45) Date of Patent: *Dec. 17, 2024

(54) HAIRPIN LOOP METHOD FOR DOUBLE STRAND POLYNUCLEOTIDE SEQUENCING USING TRANSMEMBRANE PORES

(71) Applicant: Oxford Nanopore Technologies PLC, Oxford (GB)

(72) Inventors: Clive Gavin Brown, Cambridge (GB); James Clarke, Oxford (GB); Graham Hall, Oxford (GB); Gavin Harper, Sonning (GB); Andrew John Heron, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 554 days.

This patent is subject to a terminal disclaimer.

(21) Appl. No.: 17/496,956

(22) Filed: Oct. 8, 2021

(65) Prior Publication Data

US 2022/0127669 A1  Apr. 28, 2022

Related U.S. Application Data

(63) Continuation of application No. 16/428,834, filed on May 31, 2019, now Pat. No. 11,168,363, which is a continuation of application No. 15/944,365, filed on Apr. 3, 2018, now Pat. No. 10,597,713, which is a continuation of application No. 14/234,698, filed as application No. PCT/GB2012/051786 on Jul. 25, 2012, now Pat. No. 9,957,560, application No. 17/496,956 is a continuation of application No. 16/782,350, filed on Feb. 5, 2020, now Pat. No. 11,261,487.

(60) Provisional application No. 61/511,436, filed on Jul. 25, 2011.

(51) Int. Cl.
C12Q 1/6869 (2018.01)
G01N 27/447 (2006.01)
G01N 33/487 (2006.01)

(52) U.S. Cl.
CPC ..... *C12Q 1/6869* (2013.01); *G01N 27/44717* (2013.01); *G01N 27/44791* (2013.01); *G01N 33/48721* (2013.01)

(58) Field of Classification Search
CPC ............ C12Q 1/6869; C12Q 1/6811; C12Q 2525/301; C12Q 2537/1376; C12Q 2565/631; C12Q 2535/119; G01N 27/44717; G01N 27/44791; G01N 33/48721

See application file for complete search history.

(56) References Cited

U.S. PATENT DOCUMENTS

| | | |
|---|---|---|
| 5,215,899 A | 6/1993 | Dattagupta |
| 5,424,413 A | 6/1995 | Hogan et al. |
| 5,561,043 A | 10/1996 | Cantor et al. |
| 5,714,320 A | 2/1998 | Kool |
| 5,777,078 A | 7/1998 | Bayley et al. |
| 5,795,782 A | 8/1998 | Church et al. |
| 5,817,771 A | 10/1998 | Bayley et al. |
| 5,866,328 A | 2/1999 | Bensimon et al. |
| 5,866,336 A | 2/1999 | Nazarenko et al. |
| 5,985,834 A | 11/1999 | Engel et al. |
| 6,015,714 A | 1/2000 | Baldarelli et al. |
| 6,087,099 A | 7/2000 | Gupte et al. |
| 6,123,819 A | 9/2000 | Peeters |
| 6,127,166 A | 10/2000 | Bayley et al. |
| 6,251,610 B1 | 6/2001 | Gupte et al. |
| 6,274,320 B1 | 8/2001 | Rothberg et al. |
| 6,362,002 B1 | 3/2002 | Denison et al. |
| 6,403,319 B1 | 6/2002 | Lizardi et al. |
| 6,426,231 B1 | 7/2002 | Bayley et al. |
| 6,451,563 B1 | 9/2002 | Wittig et al. |
| 6,451,593 B1 | 9/2002 | Wittig et al. |
| 6,465,193 B2 | 10/2002 | Akeson et al. |
| 6,498,023 B1 | 12/2002 | Abarzua |
| 6,627,067 B1 | 9/2003 | Branton et al. |
| 6,709,861 B2 | 3/2004 | Mead et al. |
| 6,787,308 B2 | 9/2004 | Balasubramanian et al. |
| 6,824,659 B2 | 11/2004 | Bayley et al. |
| 6,863,833 B1 | 3/2005 | Bloom et al. |
| 6,916,665 B2 | 7/2005 | Bayley et al. |

(Continued)

FOREIGN PATENT DOCUMENTS

| | | |
|---|---|---|
| CN | 101495656 A | 7/2009 |
| CN | 102245760 A | 11/2011 |

(Continued)

OTHER PUBLICATIONS

Laszlo et al, Detection and mapping of 5-methylcytosine and 5-hydroxymethyl cytosine with nanopore MspA (post art), PNAS, 110, 18904-18909 (Year: 2013).*

(Continued)

*Primary Examiner* — Narayan K Bhat
(74) *Attorney, Agent, or Firm* — Wolf, Greenfield & Sacks, P.C.

(57) ABSTRACT

The invention relates to a new method of sequencing a double stranded target polynucleotide. The two strands of the double stranded target polynucleotide are linked by a bridging moiety. The two strands of the target polynucleotide are separated using a polynucleotide binding protein and the target polynucleotide is sequenced using a transmembrane pore.

14 Claims, 28 Drawing Sheets

Specification includes a Sequence Listing.

(56) References Cited

U.S. PATENT DOCUMENTS

| | | |
|---|---|---|
| 6,927,070 B1 | 8/2005 | Bayley et al. |
| 7,087,729 B1 | 8/2006 | Prive |
| 7,189,503 B2 | 3/2007 | Akeson et al. |
| 7,238,485 B2 | 7/2007 | Akeson et al. |
| 7,361,466 B2 | 4/2008 | Korlach et al. |
| 7,507,575 B2 | 3/2009 | Bedingham et al. |
| 7,700,281 B2 | 4/2010 | Kubu et al. |
| 7,745,116 B2 | 6/2010 | Williams |
| 8,105,846 B2 | 1/2012 | Bayley et al. |
| 8,143,030 B2 | 3/2012 | Maxham et al. |
| 8,153,375 B2 | 4/2012 | Travers et al. |
| 8,343,746 B2 | 1/2013 | Rank et al. |
| 8,383,369 B2 | 2/2013 | Maxham et al. |
| 8,628,940 B2 | 1/2014 | Sorenson et al. |
| 8,652,779 B2 | 2/2014 | Turner et al. |
| 8,785,211 B2 | 7/2014 | Bayley et al. |
| 8,822,160 B2 | 9/2014 | Bayley et al. |
| 8,889,348 B2 | 11/2014 | Ju |
| 9,057,102 B2 | 6/2015 | Turner et al. |
| 9,116,118 B2 | 8/2015 | Turner et al. |
| 9,145,623 B2 | 9/2015 | Kavanagh et al. |
| 9,150,918 B2 | 10/2015 | Turner et al. |
| 9,542,527 B2 | 1/2017 | Travers et al. |
| 9,546,400 B2 | 1/2017 | Turner et al. |
| 9,551,023 B2 | 1/2017 | Turner et al. |
| 9,556,480 B2 | 1/2017 | Turner et al. |
| 9,582,640 B2 | 2/2017 | Travers et al. |
| 9,600,626 B2 | 3/2017 | Travers et al. |
| 9,670,526 B2 | 6/2017 | Kokoris et al. |
| 9,678,056 B2 | 6/2017 | Turner et al. |
| 9,738,929 B2 | 8/2017 | Turner et al. |
| 9,957,560 B2 | 5/2018 | Brown et al. |
| 10,131,944 B2 | 11/2018 | Bernick et al. |
| 10,221,450 B2 | 3/2019 | Heron et al. |
| 10,227,632 B2 | 3/2019 | Jarvius |
| 10,501,767 B2 | 12/2019 | Stoddart et al. |
| 10,570,440 B2 | 2/2020 | White et al. |
| 10,597,713 B2 | 3/2020 | Brown et al. |
| 10,669,578 B2 | 6/2020 | Clarke et al. |
| 10,851,409 B2 | 12/2020 | Brown et al. |
| 11,155,860 B2 | 10/2021 | White et al. |
| 11,168,363 B2 | 11/2021 | Brown et al. |
| 11,186,857 B2 | 11/2021 | Stoddart et al. |
| 11,261,487 B2 | 3/2022 | Brown et al. |
| 11,268,139 B2 | 3/2022 | Lu |
| 11,352,664 B2 | 6/2022 | Mckeown |
| 11,390,904 B2 | 7/2022 | White |
| 11,459,606 B2 | 10/2022 | Mckeown |
| 11,542,551 B2 | 1/2023 | Clarke et al. |
| 11,560,589 B2 | 1/2023 | Heron et al. |
| 11,649,480 B2 | 5/2023 | Stoddart et al. |
| 11,725,205 B2 | 8/2023 | White |
| 2001/0039039 A1 | 11/2001 | Weissman et al. |
| 2002/0028458 A1 | 3/2002 | Lexow |
| 2002/0094526 A1 | 7/2002 | Bayley et al. |
| 2002/0098530 A1 | 7/2002 | Pfeifer et al. |
| 2002/0132350 A1 | 9/2002 | Suzuki et al. |
| 2002/0142331 A1 | 10/2002 | Fu et al. |
| 2002/0177701 A1 | 11/2002 | Weissman et al. |
| 2002/0197618 A1 | 12/2002 | Sampson |
| 2003/0044816 A1 | 3/2003 | Denison et al. |
| 2003/0059778 A1 | 3/2003 | Berlin et al. |
| 2003/0087232 A1 | 5/2003 | Christians et al. |
| 2003/0099951 A1 | 5/2003 | Akeson et al. |
| 2003/0108902 A1 | 6/2003 | Abarzua |
| 2003/0118595 A1 | 6/2003 | Niemeyer et al. |
| 2003/0165936 A1 | 9/2003 | Rabbani et al. |
| 2003/0166137 A1 | 9/2003 | Zuker et al. |
| 2003/0211502 A1 | 11/2003 | Sauer et al. |
| 2003/0215881 A1 | 11/2003 | Bayley et al. |
| 2004/0055901 A1 | 3/2004 | Petersen et al. |
| 2004/0214177 A1 | 10/2004 | Bension |
| 2004/0229315 A1 | 11/2004 | Lee et al. |
| 2005/0042633 A1 | 2/2005 | Williams |
| 2005/0053961 A1 | 3/2005 | Akeson et al. |
| 2005/0142559 A1 | 6/2005 | Makrigiorgos |
| 2005/0221316 A1 | 10/2005 | Pedersen et al. |
| 2005/0227239 A1 | 10/2005 | Joyce |
| 2005/0260655 A1 | 11/2005 | Liu et al. |
| 2006/0063171 A1 | 3/2006 | Akeson et al. |
| 2006/0086626 A1 | 4/2006 | Joyce |
| 2006/0141516 A1 | 6/2006 | Kobold et al. |
| 2006/0147935 A1 | 7/2006 | Linnarsson |
| 2006/0292611 A1 | 12/2006 | Berka et al. |
| 2007/0015182 A1 | 1/2007 | Abarzua |
| 2007/0020640 A1 | 1/2007 | McCloskey |
| 2007/0031857 A1 | 2/2007 | Makarov et al. |
| 2007/0122885 A1 | 5/2007 | Reeves et al. |
| 2007/0224613 A1 | 9/2007 | Strathmann |
| 2007/0269825 A1 | 11/2007 | Wang et al. |
| 2007/0287151 A1 | 12/2007 | Linnarsson |
| 2008/0108082 A1 | 5/2008 | Rank et al. |
| 2008/0166724 A1 | 7/2008 | Gerber et al. |
| 2008/0206252 A1 | 8/2008 | Pennica et al. |
| 2008/0311582 A1 | 12/2008 | Bayley et al. |
| 2009/0098612 A1 | 4/2009 | Rhee et al. |
| 2009/0191598 A1 | 7/2009 | Ruan et al. |
| 2009/0256116 A1 | 10/2009 | Shumaker-Parry et al. |
| 2009/0269771 A1 | 10/2009 | Schroeder |
| 2009/0280538 A1 | 11/2009 | Patel et al. |
| 2009/0298075 A1 | 12/2009 | Travers et al. |
| 2010/0003560 A1 | 1/2010 | Shibata |
| 2010/0035254 A1 | 2/2010 | Williams |
| 2010/0035260 A1 | 2/2010 | Olasagasti et al. |
| 2010/0075309 A1 | 3/2010 | Maxham et al. |
| 2010/0075327 A1 | 3/2010 | Maxham et al. |
| 2010/0075328 A1 | 3/2010 | Bjornson et al. |
| 2010/0092960 A1 | 4/2010 | Fehr |
| 2010/0120098 A1 | 5/2010 | Grunenwald et al. |
| 2010/0121582 A1 | 5/2010 | Pan et al. |
| 2010/0221212 A1 | 9/2010 | Stagliano et al. |
| 2010/0221716 A1 | 9/2010 | Flusberg et al. |
| 2010/0276588 A1 | 11/2010 | Syms |
| 2010/0331194 A1 | 12/2010 | Turner et al. |
| 2011/0019186 A1 | 1/2011 | Himmelhaus et al. |
| 2011/0124518 A1 | 5/2011 | Cantor |
| 2011/0214991 A1 | 9/2011 | Kim et al. |
| 2011/0224106 A1 | 9/2011 | Eshoo et al. |
| 2011/0281768 A1 | 11/2011 | Travers et al. |
| 2011/0287435 A1 | 11/2011 | Grunenwald et al. |
| 2011/0311965 A1 | 12/2011 | Maglia et al. |
| 2012/0010085 A1 | 1/2012 | Rava et al. |
| 2012/0015821 A1 | 1/2012 | Raymond |
| 2012/0058468 A1 | 3/2012 | Mckeown |
| 2012/0100530 A1 | 4/2012 | Moysey et al. |
| 2012/0107802 A1 | 5/2012 | Stoddart et al. |
| 2012/0196279 A1 | 8/2012 | Underwood et al. |
| 2012/0244525 A1 | 9/2012 | Hendrickson |
| 2013/0017978 A1 | 1/2013 | Kavanagh et al. |
| 2013/0048499 A1 | 2/2013 | Mayer et al. |
| 2013/0078624 A1 | 3/2013 | Holmes et al. |
| 2013/0143802 A1 | 6/2013 | Chilkoti |
| 2013/0195908 A1 | 8/2013 | Leonetti et al. |
| 2013/0203123 A1 | 8/2013 | Nelson et al. |
| 2013/0327644 A1 | 12/2013 | Turner et al. |
| 2014/0134618 A1 | 5/2014 | Kokoris et al. |
| 2014/0134629 A1 | 5/2014 | Turner et al. |
| 2014/0186823 A1 | 7/2014 | Clarke et al. |
| 2014/0206842 A1 | 7/2014 | Majeed et al. |
| 2014/0262784 A1 | 9/2014 | Clarke et al. |
| 2014/0296089 A1 | 10/2014 | Holmes et al. |
| 2014/0308661 A1 | 10/2014 | Holmes et al. |
| 2015/0008126 A1 | 1/2015 | Maglia et al. |
| 2015/0045257 A1 | 2/2015 | Kavanagh et al. |
| 2015/0152492 A1 | 6/2015 | Brown et al. |
| 2015/0167075 A1 | 6/2015 | Turner et al. |
| 2015/0175663 A1 | 6/2015 | Yokoi et al. |
| 2015/0197796 A1 | 7/2015 | White et al. |
| 2015/0218629 A1 | 8/2015 | Heron et al. |
| 2015/0265994 A1 | 9/2015 | Hyde et al. |
| 2015/0285781 A1 | 10/2015 | Heron et al. |
| 2015/0307934 A1 | 10/2015 | Turner et al. |
| 2016/0010147 A1 | 1/2016 | Heron et al. |
| 2016/0010148 A1 | 1/2016 | Turner et al. |

(56) References Cited

U.S. PATENT DOCUMENTS

| | | |
|---|---|---|
| 2016/0011169 A1 | 1/2016 | Turner et al. |
| 2016/0194677 A1 | 7/2016 | Stoddart et al. |
| 2016/0257942 A1 | 9/2016 | Bruce et al. |
| 2016/0281159 A1 | 9/2016 | Brown et al. |
| 2016/0362739 A1 | 12/2016 | Brown et al. |
| 2017/0002406 A1 | 1/2017 | Bowen et al. |
| 2017/0067101 A1 | 3/2017 | Clarke et al. |
| 2017/0226503 A1 | 8/2017 | Strachan et al. |
| 2017/0240955 A1 | 8/2017 | White |
| 2017/0314062 A1 | 11/2017 | Kokoris et al. |
| 2017/0321266 A1 | 11/2017 | Mckeown |
| 2018/0030506 A1 | 2/2018 | Fujioka |
| 2018/0051277 A1 | 2/2018 | Godfrey et al. |
| 2018/0291440 A1 | 10/2018 | Mckeown |
| 2018/0291441 A1 | 10/2018 | Brown et al. |
| 2019/0194722 A1 | 6/2019 | Stoddart et al. |
| 2019/0211390 A1 | 7/2019 | Heron et al. |
| 2019/0376132 A1 | 12/2019 | Mckeown |
| 2020/0002761 A1 | 1/2020 | Mckeown |
| 2020/0024655 A1 | 1/2020 | Brown et al. |
| 2020/0032248 A1 | 1/2020 | White et al. |
| 2020/0109396 A1 | 4/2020 | Tsai et al. |
| 2020/0131549 A1 | 4/2020 | Stoddart et al. |
| 2020/0239950 A1 | 7/2020 | Brown et al. |
| 2020/0291452 A1 | 9/2020 | White |
| 2020/0318179 A1 | 10/2020 | Clarke et al. |
| 2022/0145383 A1 | 5/2022 | White et al. |
| 2022/0186274 A1 | 6/2022 | Stoddart et al. |
| 2023/0046363 A1 | 2/2023 | White |
| 2023/0065890 A1 | 3/2023 | Mckeown |
| 2023/0212665 A1 | 7/2023 | Heron et al. |
| 2023/0250474 A1 | 8/2023 | Clarke et al. |
| 2023/0374567 A1 | 11/2023 | Stoddart et al. |
| 2024/0117337 A1 | 4/2024 | White |

FOREIGN PATENT DOCUMENTS

| | | |
|---|---|---|
| CN | 105209634 A | 12/2015 |
| CN | 105705656 A | 6/2016 |
| DE | 112016000293 T5 | 9/2017 |
| EP | 2682460 A1 | 1/2014 |
| EP | 3470529 A1 | 4/2019 |
| GB | 2130219 A | 5/1984 |
| GB | 2237390 A | 5/1991 |
| GB | 2453377 A | 4/2009 |
| JP | H11-137260 A | 5/1999 |
| JP | 2012-506704 A | 3/2012 |
| WO | WO 1994/23065 | 10/1994 |
| WO | WO 1999/05167 | 2/1999 |
| WO | WO 2000/28312 A1 | 5/2000 |
| WO | WO 2001/40516 A2 | 6/2001 |
| WO | WO 2001/42782 A1 | 6/2001 |
| WO | WO 2001/59453 A2 | 8/2001 |
| WO | WO 2002/42496 A2 | 5/2002 |
| WO | WO 2003/095669 A1 | 11/2003 |
| WO | WO 2005/056750 A2 | 6/2005 |
| WO | WO 2005/068656 A1 | 7/2005 |
| WO | WO 2005/118877 A2 | 12/2005 |
| WO | WO 2005/124888 A1 | 12/2005 |
| WO | WO 2006/020775 A2 | 2/2006 |
| WO | WO 2006/028508 A2 | 3/2006 |
| WO | WO 2006/100484 A2 | 9/2006 |
| WO | WO 2007/057668 A1 | 5/2007 |
| WO | WO 2007/075987 A2 | 7/2007 |
| WO | WO 2007/084103 A2 | 7/2007 |
| WO | WO 2007/114693 A2 | 10/2007 |
| WO | WO 2007/146158 A1 | 12/2007 |
| WO | WO 2008/045575 A2 | 4/2008 |
| WO | WO 2008/083554 A1 | 7/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/044170 A1 | 4/2009 |
| WO | WO 2009/077734 A2 | 6/2009 |
| WO | WO 2009/120372 A2 | 10/2009 |
| WO | WO 2009/120374 A2 | 10/2009 |
| WO | WO 2010/004265 A1 | 1/2010 |
| WO | WO 2010/004273 A1 | 1/2010 |
| WO | WO 2010/030683 A1 | 3/2010 |
| WO | WO 2010/034018 A2 | 3/2010 |
| WO | WO 2010/048605 A1 | 4/2010 |
| WO | WO 2010/051773 A1 | 5/2010 |
| WO | WO 2010/086602 A1 | 8/2010 |
| WO | WO 2010/086603 A1 | 8/2010 |
| WO | WO 2010/086622 A1 | 8/2010 |
| WO | WO 2010/094040 A1 | 8/2010 |
| WO | WO 2010/109107 A1 | 9/2010 |
| WO | WO 2010/109197 A2 | 9/2010 |
| WO | WO 2010/117470 A1 | 10/2010 |
| WO | WO 2010/122293 A1 | 10/2010 |
| WO | WO 2010/146349 A1 | 12/2010 |
| WO | WO 2011/067559 A1 | 6/2011 |
| WO | WO 2012/033524 A2 | 3/2012 |
| WO | WO 2012/061832 A1 | 5/2012 |
| WO | WO 2012/083249 A2 | 6/2012 |
| WO | WO 2012/098561 A2 | 7/2012 |
| WO | WO 2012/098562 A2 | 7/2012 |
| WO | WO 2012/103545 A1 | 8/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/131962 A1 | 9/2013 |
| WO | WO 2013/153359 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/108810 A2 | 7/2014 |
| WO | WO 2014/135838 A1 | 9/2014 |
| WO | WO 2014/153408 A1 | 9/2014 |
| WO | WO 2015/022544 A1 | 2/2015 |
| WO | WO 2015/031909 A1 | 3/2015 |
| WO | WO 2015/055981 A2 | 4/2015 |
| WO | WO 2015/056028 A1 | 4/2015 |
| WO | WO 2015/110777 A1 | 7/2015 |
| WO | WO 2015/110813 A1 | 7/2015 |
| WO | WO 2015/189636 A1 | 12/2015 |
| WO | WO 2015/200609 A1 | 12/2015 |
| WO | WO 2016/003814 A1 | 1/2016 |
| WO | WO 2016/022557 A1 | 2/2016 |
| WO | WO 2016/028887 A1 | 2/2016 |
| WO | WO 2016/034591 A2 | 3/2016 |
| WO | WO 2016/055777 A2 | 4/2016 |
| WO | WO 2016/059363 A1 | 4/2016 |
| WO | WO 2017/215500 A1 | 12/2017 |

OTHER PUBLICATIONS

International Search Report and Written Opinion for Application No. PCT/GB2012/051786, mailed Nov. 6, 2012.
International Preliminary Report on Patentability for Application No. PCT/GB2012/051786, mailed Jan. 28, 2014.
[No Author Listed], Multiplex sequencing. https://www.illumina.com/science/technology/next-generation-sequencing/multiplex-sequencing.html. Printed on Nov. 4, 2021. 1 page.
[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.
Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.
Altschul et al., Basic local alignment search tool. J Mol Biol. Oct. 5, 1990;215(3):403-10.

(56) References Cited

OTHER PUBLICATIONS

Altschul, A protein alignment scoring system sensitive at all evolutionary distances. J Mol Evol. Mar. 1993;36(3):290-300.
Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.
Ashkenasy et al., Recognizing a single base in an individual DNA strand: a step toward DNA sequencing in nanopores. Angew Chem Int Ed Engl. Feb. 18, 2005;44(9):1401-4.
Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley, Sequencing single molecules of DNA. Curr Opin Chem Biol. Dec. 2006; 10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Berger et al., Universal bases for hybridization, replication and chain termination. Nucleic Acids Res. Aug. 1, 2000;28(15):2911-4.
Bowie et al., Deciphering the message in protein sequences: tolerance to amino acid substitutions. Science. Mar. 16, 1990;247(4948):1306-10.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci U S A. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Cheng, et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.
Chin et al., The origin of the Haitian cholera outbreak strain. N Engl J Med. Jan. 6, 2011;364(1):33-42 and Supplemental Mateial. doi: 10.1056/NEJMoa1012928. Epub Dec. 9, 2010. Author Manuscript. 304 pages.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Colas et al., Microscopical investigations of nisin-loaded nanoliposomes prepared by Mozafari method and their bacterial targeting. Micron. 2007;38(8):841-7. Epub Jul. 3, 2007.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.

(56) References Cited

OTHER PUBLICATIONS

Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.

Devereux et al., A comprehensive set of sequence analysis programs for the VAX. Nucleic Acids Res. Jan. 11, 1984;12(1 Pt 1):387-95.

Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.

Dorre et al., Techniques for single molecule sequencing. Bioimaging, vol. 5:139-152 (1997).

Eid et al., Real-time DNA sequencing from single polymerase molecules. Science. Jan. 2, 2009;323(5910):133-8. doi:10.1126/science.1162986. Epub Nov. 20, 2008.

Eliseev et al., Aminocyclodextrins as Selective Hosts with Several Binding Sites for Nucleotides. Angew. Chem. Int. Ed. Engl., vol. 32(9):1331-1333 (1993).

Eliseev et al., Molecular Recognition of Nucleotides, Nucleosides, and Sugars by Aminocyclodextrins. J. Am. Chem. Soc., 1994;116:6081-6088.

El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.

Erie et al., A dumbbell-shaped, double-hairpin structure of DNA: a thermodynamic investigation. Biochemistry. Nov. 3, 1987;26(22):7150-9.

Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.

Faller et al., The structure of a mycobacterial outer-membrane channel. Science. Feb. 20, 2004;303(5661):1189-92. doi: 10.1126/science.1094114.

Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.

Flusberg et al., Direct detection of DNA methylation during single-molecule, real-time sequencing. Nat Methods. Jun. 2010;7(6):461-5. doi: 10.1038/nmeth.1459. Epub May 9, 2010.

Gacillàn-Barcia et al., The diversity of conjugative relaxases and its application in plasmid classification. FEMS Microbiol Rev. May 2009;33(3):657-87.

Genschel et al., Interaction of E. coli single-stranded DNA binding protein (SSB) with exonuclease I. The carboxy-terminus of SSB is the recognition site for the nuclease. Biol Chem. Mar. 2000;381(3):183-92.

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.

Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.

Gill et al., Nucleic acid isothermal amplification technologies: a review. Nucleosides Nucleotides Nucleic Acids. Mar. 2008;27(3):224-43. doi: 10.1080/15257770701845204.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. Epub May 21, 2007.

Gu et al., Capture of a single molecule in a nanocavity. Science. Jan. 26, 2001;291(5504):636-40.

Gu et al., Electroosmotic enhancement of the binding of a neutral molecule to a transmembrane pore. Proc Natl Acad Sci U S A. Dec. 23, 2003;100(26):15498-503. Epub Dec. 15, 2003.

Gu et al., Prolonged residence time of a noncovalent molecular adapter, beta-cyclodextrin, within the lumen of mutant alpha-hemolysin pores. J Gen Physiol. Nov. 2001;118(5):481-94.

Gu et al., Reversal of charge selectivity in transmembrane protein pores by using noncovalent molecular adapters. Proc Natl Acad Sci U S A. Apr. 11, 2000;97(8):3959-64.

Gu et al., Single molecule sensing by nanopores and nanopore devices. Analyst. Mar. 2010;135(3):441-51. doi: 10.1039/b907735a. Epub Dec. 22, 2009.

Gu et al., Stochastic sensing of organic analytes by a pore-forming protein containing a molecular adapter. Nature. Apr. 22, 1999;398(6729):686-90.

Guan et al., Stochastic sensing of TNT with a genetically engineered pore. Chembiochem. Oct. 2005;6(10):1875-81.

Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.

Han et al., Characterization and optimization of an entropic trap for DNA separation. Anal Chem. Jan. 15, 2002;74(2):394-401.

Han et al., RecJ exonuclease: substrates, products and interaction with SSB. Nucleic Acids Res. Feb. 18, 2006;34(4):1084-91. Print 2006.

He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.

He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Henrickson et al., Driven DNA transport into an asymmetric nanometer-scale pore. Phys Rev Lett. Oct. 2, 2000;85(14):3057-60.

Heredia et al., In vitro double transposition for DNA identification. Anal Biochem. Apr. 1, 2010;399(1):78-83. doi: 10.1016/j.ab.2009.11.030. Epub Nov. 26, 2009.

Heron et al., Simultaneous measurement of ionic current and fluorescence from single protein pores. J Am Chem Soc. Feb. 11, 2009;131(5):1652-3. doi: 10.1021/ja808128s.

Hobbs et al., SSB protein limits RecOR binding onto single-stranded DNA. J Biol Chem. Apr. 13, 2007;282(15):11058-67. Epub Feb. 1, 2007.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.

Hornblower et al., Single-molecule analysis of DNA-protein complexes using nanopores. Nat Methods. Apr. 2007;4(4):315-7. Epub Mar. 4, 2007.

Howorka et al., DNA Duplex Formation of Individual DNA Strands within a Single Protein Pore. Biophysical Journal, vol. 82{1, pt. 2):508a, No. 2482-Plat (2002).

Howorka et al., Improved protocol for high-throughput cysteine scanning mutagenesis. Biotechniques. Nov. 1998;25(5):764-6, 768, 770 passim.

Howorka et al., Kinetics of duplex formation for individual DNA strands within a single protein nanopore. Proc Natl Acad Sci U S A. Nov. 6, 2001;98(23):12996-3001. Epub Oct. 23, 2001.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.

(56) References Cited

OTHER PUBLICATIONS

Hwang et al., Electrical behavior of droplet interface bilayer networks: experimental analysis and modeling. J Am Chem Soc. Sep. 26, 2007;129(38):11854-64. Epub Sep. 1, 2007.

Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.

Ivanov et al., DNA tunneling detector embedded in a nanopore. Nano Lett. Jan. 12, 2011;11(1):279-85. doi: 10.1021/nl103873a. Epub Dec. 6, 2010.

Jayasinghe et al., The leukocidin pore: evidence for an octamer with four LukF subunits and four LukS subunits alternating around a central axis. Protein Sci. Oct. 2005;14(10):2550-61.

Jung et al., The internal cavity of the staphylococcal alpha-hemolysin pore accommodates approximately 175 exogenous amino acid residues. Biochemistry. Jun. 28, 2005;44(25):8919-29.

Kahvejian et al., Making single-molecule sequencing a reality. American Laboratory. Jan. 1, 2008;40(20):48-53. www.americanlaboratory.com/913-Technical-Articles/780-Making-Single-Molecule-Sequencing-a-Reality/. Last accessed Dec. 10, 2021.

Kalisch et al., Covalently linked sequencing primer linkers (splinkers) for sequence analysis of restriction fragments. Gene. 1986;44(2-3):263-70.

Kanan et al., Reaction discovery enabled by DNA-templated synthesis and in vitro selection. Nature. Sep. 30, 2004;431(7008):545-9.

Kang et al., Single protein pores containing molecular adapters at high temperatures. Angew Chem Int Ed Engl. Feb. 25, 2005;44(10):1495-9.

Kasianowicz et al., Characterization of individual polynucleotide molecules using a membrane channel. Proc Natl Acad Sci U S A. Nov. 26, 1996;93(24):13770-3.

Keyser, Controlling molecular transport through nanopores. J R Soc Interface. Oct. 7, 2011;8(63):1369-78. doi: 10.1098/rsif.2011.0222. Epub Jun. 29, 2011.

Khulbe et al., DNA translocation through a-hemolysin nanopores with potential application to macromolecular data storage. Journal Applied Physics, vol. 97(104317):1-7 (2005).

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kovall et al., Toroidal structure of lambda-exonuclease. Science. Sep. 19, 1997;277(5333):1824-7.

Kozarewa et al., 96-plex molecular barcoding for the Illumina Genome Analyzer. Methods Mol Biol. 2011;733:279-98. doi: 10.1007/978-1-61779-089-8_20.

Kozlov et al., Regulation of Single-stranded DNA Binding by the C Termini of *Esherichia coli* Single-stranded DNA-binding (SBB) Protein. J. Biol. Chem. May 28, 2010;285(22):17246-52.

Kuipers, Random mutagenesis by using mixtures of dNTP and dITP in PCR. Methods Mol Biol. 1996;57:351-6. doi: 10.1385/0-89603-332-5:351.

Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.

Langecker et al., Synthetic lipid membrane channels formed by designed DNA nanostructures. Science. Nov. 16, 2012;338(6109):932-6. doi: 10.1126/science.1225624.

Lazar et al., Transforming growth factor alpha: mutation of aspartic acid 47 and leucine 48 results in different biological activities. Mol Cell Biol. Mar. 1988;8(3):1247-52.

Lee et al., Importance of the conserved CA dinucleotide at Mu termini. J Mol Biol. Nov. 30, 2001;314(3):433-44.

Li et al., DNA molecules and configurations in a solid-state nanopore microscope. Nat Mater. Sep. 2003;2(9):611-5. Epub Aug. 24, 2003.

Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Liu et al., Adding new chemistries to the genetic code. Annu Rev Biochem. 2010;79:413-44. doi: 10.1146/annurev.biochem.052308.105824.

Liu et al., Structure of the DNA repair helicase XPD. Cell. May 30, 2008;133(5):801-12. doi: 10.1016/j.cell.2008.04.029.

Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.

Lohman et al., Non-hexameric DNA helicases and translocases: mechanisms and regulation. Nat Rev Mol Cell Biol. May 2008;9(5):391-401. doi: 10.1038/nrm2394.

Lovett et al., Identification and purification of a single-stranded-DNA-specific exonuclease encoded by the recJ gene of *Escherichia coli*. Proc Natl Acad Sci U S A. Apr. 1989;86(8):2627-31.

Lovrinovic et al., Rapid synthesis of DNA-cysteine conjugates for expressed protein ligation. Biochem Biophys Res Commun. Sep. 30, 2005;335(3):943-8.

Lu et al., Peptide inhibitors identify roles for SSB C-terminal residues in SSB/Exonuclease I complex formation. Biochemistry. Jul. 28, 2009; 48(29): 6764-6771. doi: 10.1021/bi900361r. Author Manuscript.

Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.

Luo et al., Influence of polymer-pore interactions on translocation. Phys Rev Lett. Oct. 5, 2007;99(14):148102. Epub Oct. 1, 2007.

Lutz et al., Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.

Ma et al., Bright functional rotaxanes. Chem Soc Rev. Jan. 2010;39(1):70-80. doi: 10.1039/b901710k. Epub Jul. 21, 2009.

Maglia et al., Analysis of single nucleic acid molecules with protein nanopores. Methods Enzymol. 2010;475:591-623. doi: 10.1016/S0076-6879(10)75022-9.

Maglia et al., Enhanced translocation of single DNA molecules through alpha-hemolysin nanopores by manipulation of internal charge. Proc Natl Acad Sci U S A. Dec. 16, 2008;105(50):19720-5. doi: 10.1073/pnas.0808296105. Epub Dec. 5, 2008.

Martin et al., Nanoscale protein pores modified with PAMAM dendrimers. J Am Chem Soc. Aug. 8, 2007;129(31):9640-9. Epub Jul. 18, 2007.

Martínez et al., The mRNA cap structure stimulates rate of poly(A) removal and amplifies processivity of degradation. J Biol Chem. Jul. 27, 2001;276(30):27923-9. Epub May 18, 2001.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

(56) References Cited

OTHER PUBLICATIONS

Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
Mitchell et al., Chemical tags facilitate the sensing of individual DNA strands with nanopores. Angew Chem Int Ed Engl. 2008;47(30):5565-8. doi:10.1002/anie.200800183.
Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.
Mol et al., Structure and function of the multifunctional DNA-repair enzyme exonuclease III. Nature. Mar. 23, 1995;374(6520):381-6.
Montal et al., Formation of bimolecular membranes from lipid monolayers and a study of their electrical properties. Proc Natl Acad Sci U S A. Dec. 1972;69(12):3561-6.
Movileanu et al., Detecting protein analytes that modulate transmembrane movement of a polymer chain within a single protein pore. Nat Biotechnol. Oct. 2000;18(10):1091-5.
Movileanu et al., Location of a constriction in the lumen of a transmembrane pore by targeted covalent attachment of polymer molecules. J Gen Physiol. Mar. 2001;117(3):239-52.
Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.
Nakane et al., A nanosensor for transmembrane capture and identification of single nucleic Acid molecules. Biophys J. Jul. 2004;87(1):615-21. Erratum in: Biophys J. Nov. 2004;87(5):3618.
Nakane et al., Nanopore sensors for nucleic acid analysis. J. Phys.: Condens. Matter, vol. 15: R 1365-R1393 (2003).
Niemeyer et al., DNA-directed assembly of bienzymic complexes from in vivo biotinylated NAD(P)H:FMN oxidoreductase and luciferase. Chembiochem. Mar. 1, 2002;3(2-3):242-5.
Nikolov et al., Behavior of giant vesicles with anchored DNA molecules. Biophys J. Jun. 15, 2007;92(12):4356-68. Epub Mar. 23, 2007.
North et al., Host factors that promote transpososome disassembly and the PriA-PriC pathway for restart primosome assembly. Mol Microbiol. Jun. 2005;56(6):1601-16.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
O'Shea et al., X-ray structure of the GCN4 leucine zipper, a two-stranded, parallel coiled coil. Science. Oct. 25, 1991;254(5031):539-44.
Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.
Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.
Pettersson et al., Generations of sequencing technologies. Genomics. Feb. 2009;93(2):105-11. doi: 10.1016/j.ygeno.2008.10.003. Epub Nov. 21, 2008.
Pfeiffer et al., Bivalent cholesterol-based coupling of oligonucletides to lipid membrane assemblies. J Am Chem Soc. Aug. 25, 2004;126(33):10224-5.
Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.
Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.

Remaut et al., Protein-protein interaction through beta-strand addition. Trends Biochem Sci. Aug. 2006;31(8):436-44. Epub Jul. 7, 2006.
Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.
Saariaho et al., Characteristics of MuA transposase-catalyzed processing of model transposon end DNA hairpin substrates. Nucleic Acids Res. Jun. 6, 2006;34(10):3139-49. Print 2006.
Sanchez-Quesada et al., Cyclic Peptides as Molecular Adapters for a Pore-Forming Protein. Journal American Chemical Society, vol. 122(48):11757-11766 (2000).
Sanchez-Quesada et al., Single DNA rotaxanes of a transmembrane pore protein. Angew Chem Int Ed Engl. Jun. 7, 2004;43(23):3063-7.
Sanderson, Personal genomes: Standard and pores. Nature. Nov. 6, 2008;456(7218):23-5. doi: 10.1038/456023a.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.x. Epub Mar. 9, 2008.
Sauer-Budge et al., Unzipping kinetics of double-stranded DNA in a nanopore. Phys Rev Lett. Jun. 13, 2003;90(23):238101. Epub Jun. 9, 2003.
Schneider et al., DNA sequencing with nanopores. Nat Biotechnol. Apr. 10, 2012;30(4):326-8. doi: 10.1038/nbt.2181.
Seeman, Nucleic acid junctions and lattices. J Theor Biol. Nov. 21, 1982;99(2):237-47.
Seo et al., Click chemistry to construct fluorescent oligonucleotides for DNA sequencing. J Org Chem. Jan. 24, 2003;68(2):609-12.
Seol et al., Stretching of homopolymeric RNA reveals single-stranded helices and base-stacking. Phys Rev Lett. Apr. 13, 2007;98(15):158103. Epub Apr. 12, 2007.
Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.
Shendure et al., Overview of DNA sequencing strategies. Curr Protoc Mol Biol. Jan. 2008;Chapter 7:Unit 7.1. doi: 10.1002/0471142727.mb0701s81.
Shin et al., Kinetics of a reversible covalent-bond-forming reaction observed at the single-molecule level. Angew Chem Int Ed Engl. Oct. 4, 2002;41(19):3707-9; 3523.
Smeets et al., Salt dependence of ion transport and DNA translocation through solid-state nanopores. Nano Lett. Jan. 2006;6(1):89-95.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Song et al., Structure of staphylococcal alpha-hemolysin, a heptameric transmembrane pore. Science. Dec. 13, 1996;274(5294):1859-66.
Soni et al., Synchronous optical and electrical detection of biomolecules traversing through solid-state nanopores. Rev Sci Instrum. Jan. 2010;81(1):014301. doi: 10.1063/1.3277116.
Spee et al., Efficient random mutagenesis method with adjustable mutation frequency by use of PCR and dITP. Nucleic Acids Res. Feb. 11, 1993;21(3):777-8. doi: 10.1093/nar/21.3.777.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sutherland et al., An analysis of mismatched duplex DNA unzipping through a bacterial nanopore. Biochem Cell Biol. Jun. 2004;82(3):407-12.
Tadey et al., Capillary electrophoretic separation of nucleotide isomers via complexation with cyclodextrin and borate. J Chromatogr B Biomed Appl. Jul. 15, 1994;657(2):365-72.
Thomas et al., Processivity of DNA exonucleases. J Biol Chem. Jan. 25, 1978;253(2):424-9.

(56) References Cited

OTHER PUBLICATIONS

Tohda et al., "Channel Mimetic Sensing Membranes for Nucleotides Based on Multitopic Hydrogen Bonding," Israel Journal of Chemistry, vol. 37:267-275 (1997).
Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
Tung et al., Preparation and applications of peptide-oligonucleotide conjugates. Bioconjug Chem. Sep.-Oct. 2000;11(5):605-18.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
United States District Court for the District of Delaware Order. *Pacific Biosciences of California, Inc. v. Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Heel et al., Single-particle electron cryo-microscopy: towards atomic resolution. Q Rev Biophys. Nov. 2000;33(4):307-69.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., A simple and reproducible method for directed evolution: combination of random mutation with dITP and DNA fragmentation with endonuclease V. Mol Biotechnol. Jan. 2013;53(1):49-54. doi: 10.1007/s12033-012-9516-9.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011; 6(4): 253-260. EPub Feb. 20, 2011. doi: 10.1038/nnano.2011.12.
Cui et al., Maize Mu transposon and its application in reverse genetic research. Bulletin of Agricultural Science and Technology. Dec. 31, 2010;1:35-38.
Manosas et al., Magnetic tweezers for the study of DNA tracking motors. Methods Enzymol. 2010;475:297-320. doi: 10.1016/S0076-6879(10)75013-8.
Matson et al., The gene 4 protein of bacteriophage T7. Characterization of helicase activity. J Biol Chem. Nov. 25, 1983;258(22):14017-24.
Mitchel et al., Heteroduplex DNA position defines the roles of the Sgs1, Srs2, and Mph1 helicases in promoting distinct recombination outcomes. PLoS Genet. 2013;9(3):e1003340. doi: 10.1371/journal.pgen.1003340. Epub Mar. 14, 2013.
Nakai et al., Handoff from recombinase to replisome: insights from transposition. Proc Natl Acad Sci U S A. Jul. 17, 2001;98(15):8247-54. doi: 10.1073/pnas.111007898.
Notomi et al., Loop-mediated isothermal amplification of DNA. Nucleic Acids Res. Jun. 15, 2000;28(12):E63. doi: 10.1093/nar/28.12.e63.
Singleton et al., Structure and mechanism of helicases and nucleic acid translocases. Annu Rev Biochem. 2007;76:23-50. doi: 10.1146/annurev.biochem.76.052305.115300.
Skipper et al., DNA transposon-based gene vehicles—scenes from an evolutionary drive. J Biomed Sci. Dec. 9, 2013;20(1):92. doi: 10.1186/1423-0127-20-92.

* cited by examiner

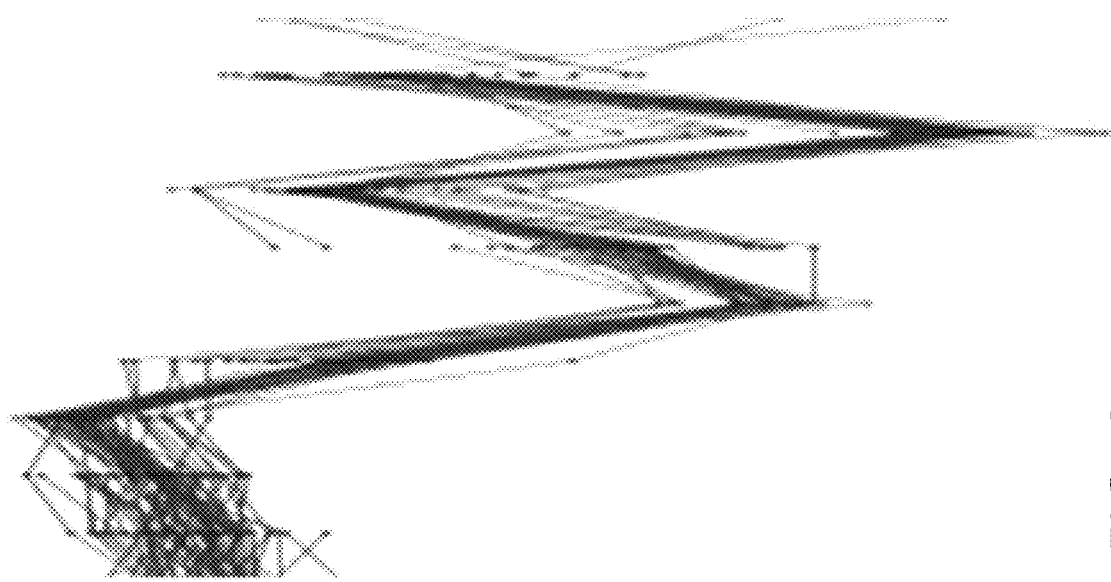
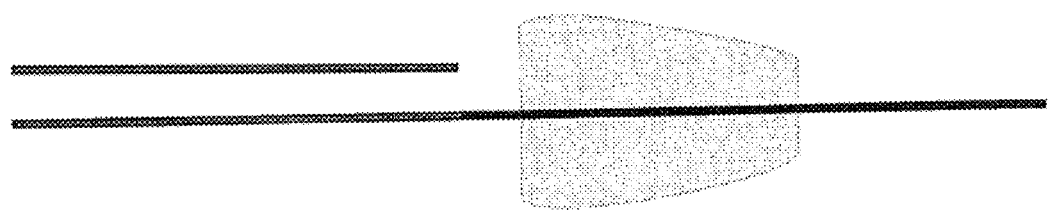
FIG. 4

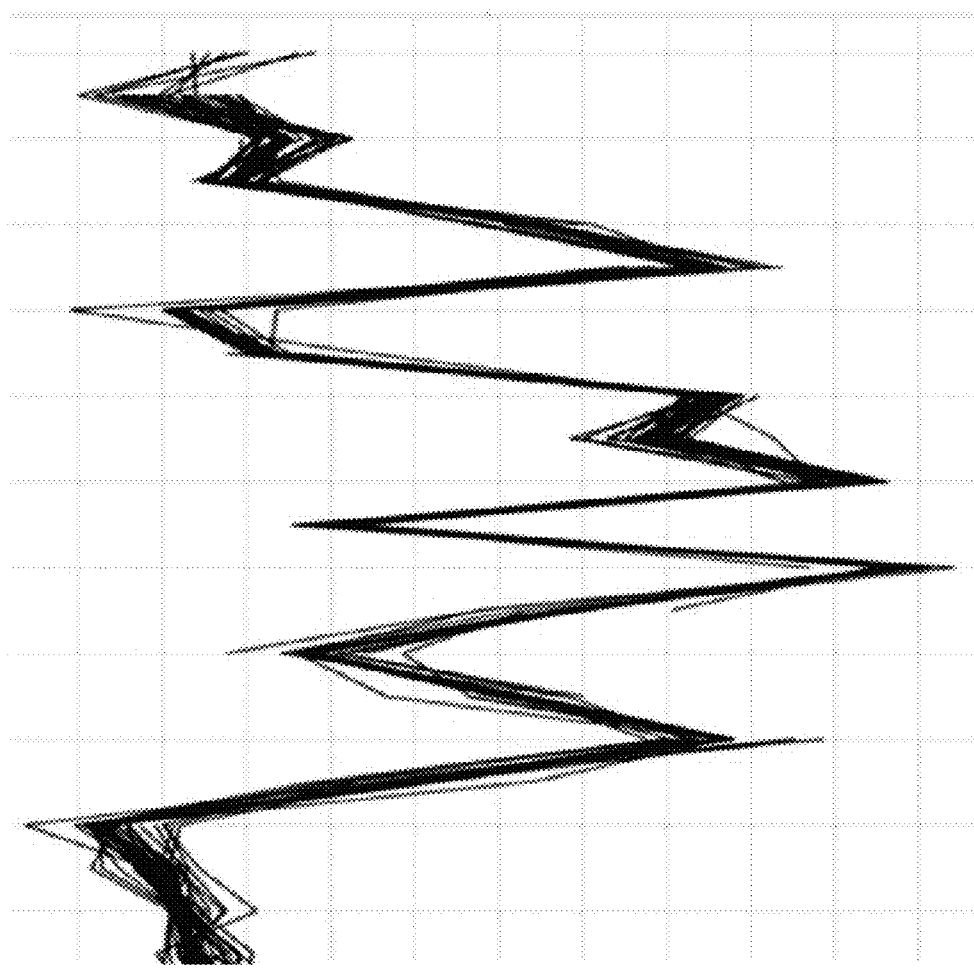
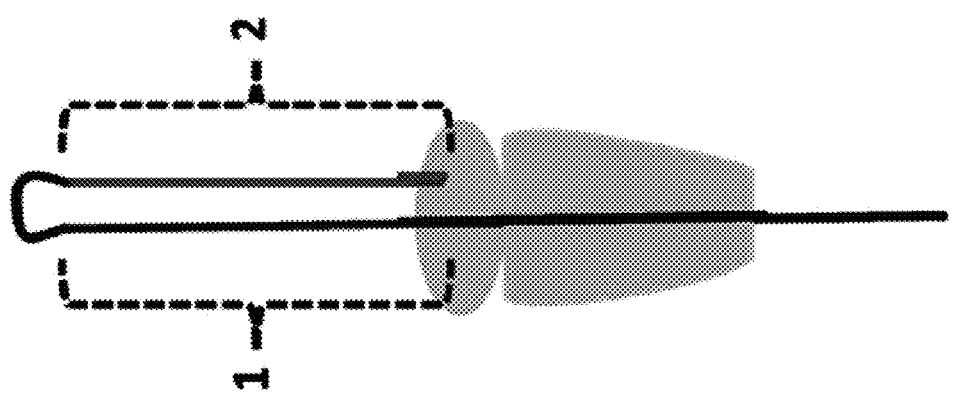
FIG. 5

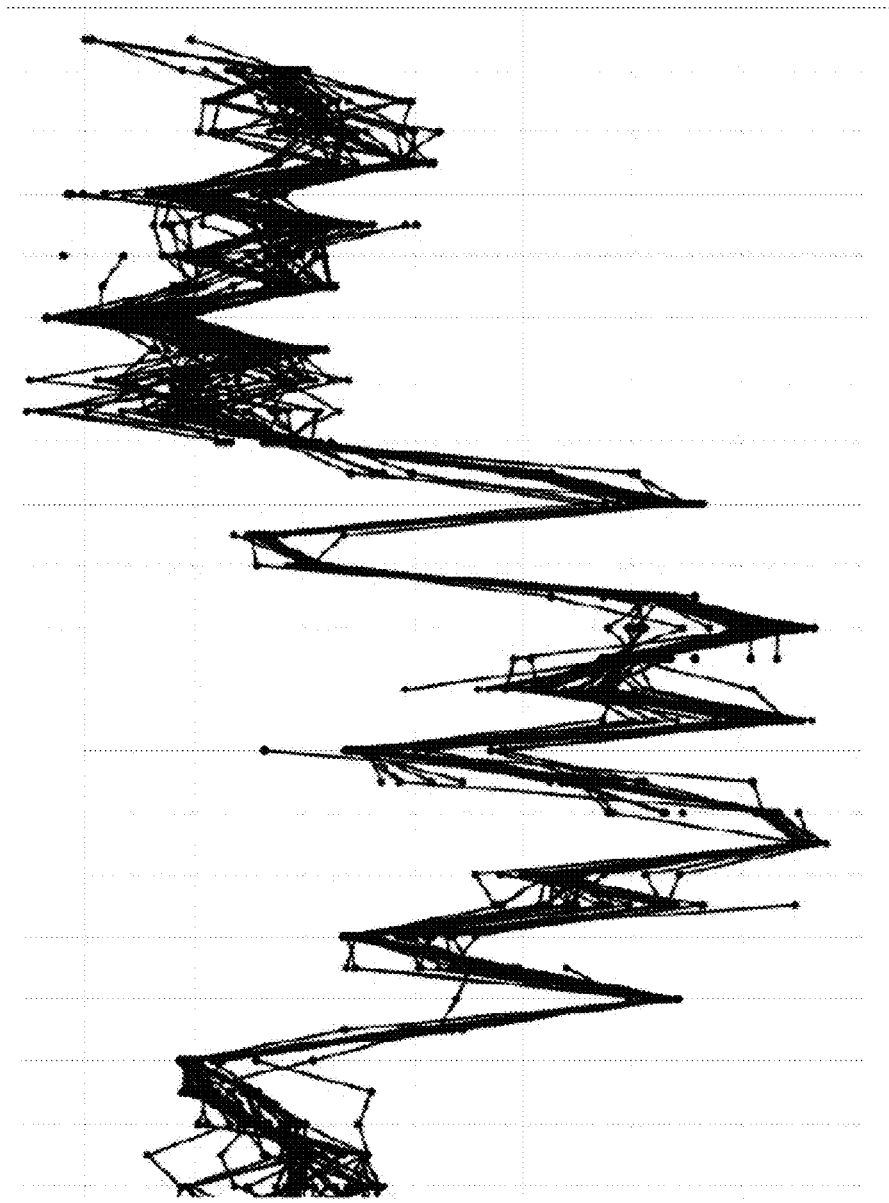
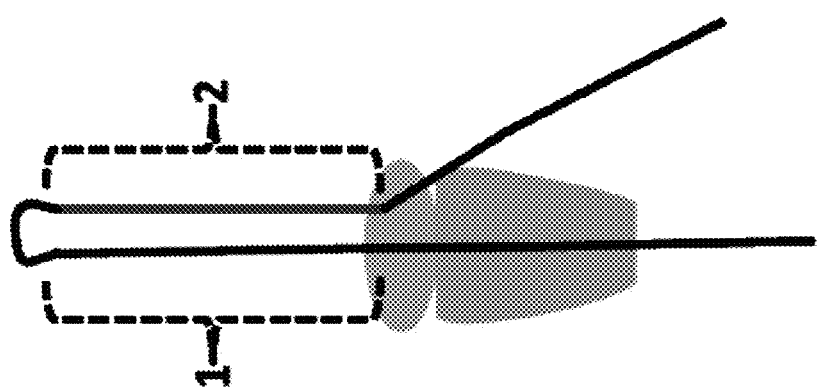
FIG. 6

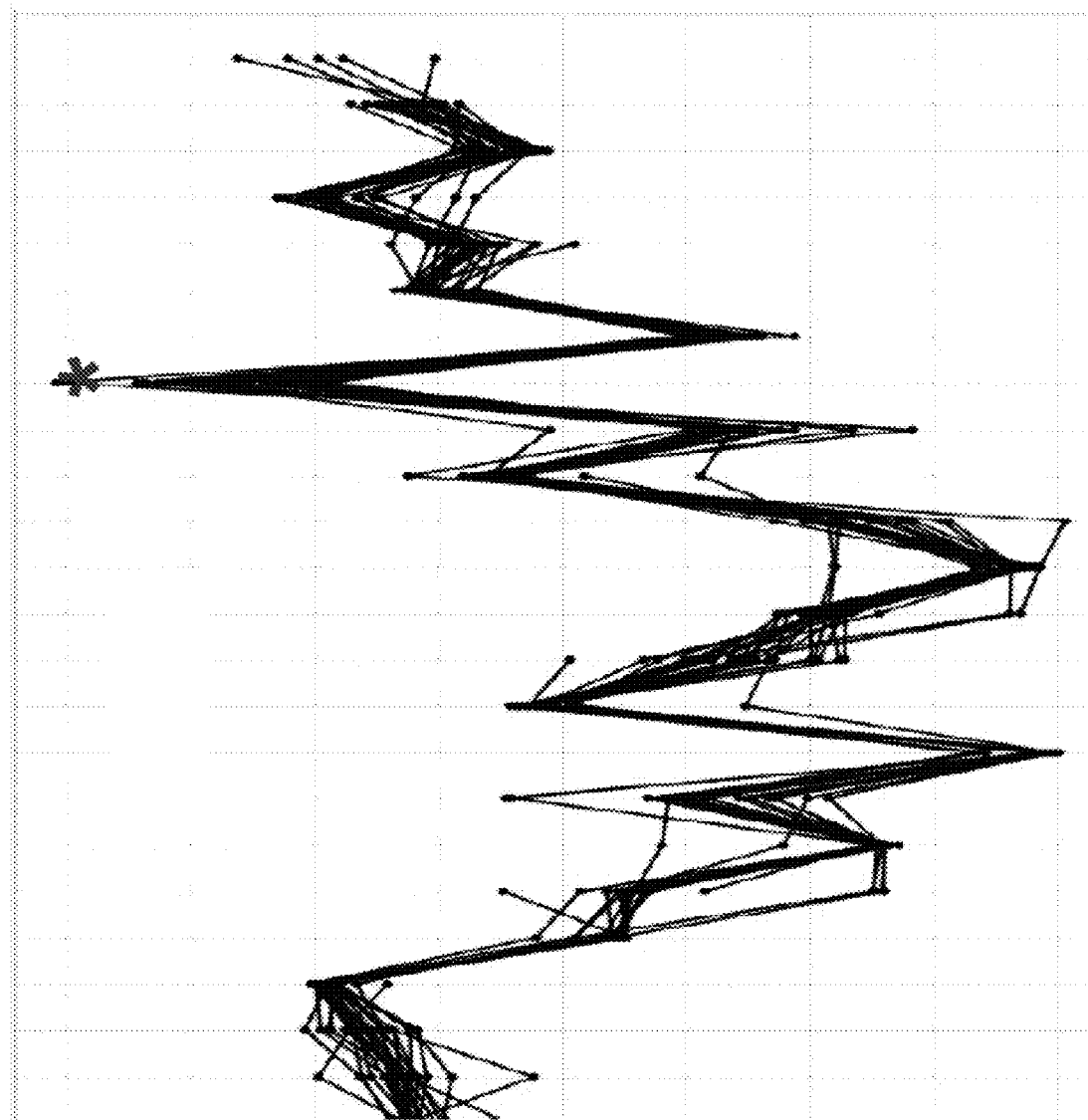
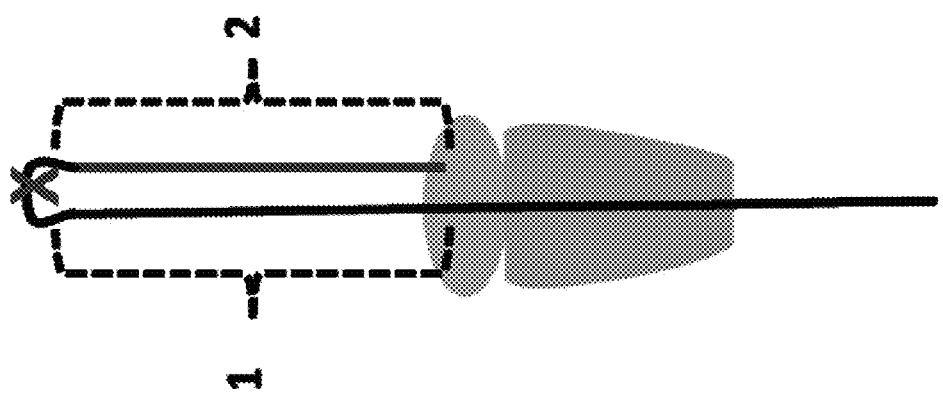
FIG. 7

HAIRPIN LOOP METHOD FOR DOUBLE STRAND POLYNUCLEOTIDE SEQUENCING USING TRANSMEMBRANE PORES

RELATED APPLICATIONS

This application is a continuation of U.S. application Ser. No. 16/782,350, filed Feb. 20, 2020, and a continuation of U.S. application Ser. No. 16/428,834, filed May 31, 2019, which is a continuation of U.S. application Ser. No. 15/944,365 filed on Apr. 3, 2018, which is a continuation of U.S. application Ser. No. 14/234,698 filed on Apr. 25, 2014, which is a national stage filing under U.S.C. § 371 of PCT International Application No. PCT/GB2012/051786, with an international filing date of Jul. 25, 2012, which claims the benefit under 35 U.S.C. § 119(e) to U.S. Provisional Application Ser. No. 61/511,436 filed on Jul. 25, 2011, the contents of each of which are incorporated herein by reference in their entireties.

REFERENCE TO AN ELECTRONIC SEQUENCE LISTING

The contents of the electronic sequence listing (0036670031US07-SEQ-KZM.txt; Size: 31,704 bytes; and Date of Creation: Oct. 8, 2021) is herein incorporated by reference in its entirety.

FIELD OF THE INVENTION

The invention relates to a new method of sequencing a double stranded target polynucleotide. The two strands of the target polynucleotide are linked by a bridging moiety. The two strands of the target polynucleotide are separated by a polynucleotide binding protein. Sequencing of the target polynucleotide is carried out using a transmembrane pore.

BACKGROUND OF THE INVENTION

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a drop in the current flow when an analyte, such as a nucleotide, resides transiently in the barrel for a certain period of time. Nanopore detection of the nucleotide gives a current blockade of known signature and duration. The concentration of a nucleotide can then be determined by the number of blockade events (where an event is the translocation of an analyte through the nanopore) per unit time to a single pore.

In the "Strand Sequencing" method, a single polynucleotide strand is passed through the pore and the nucleotides are directly identified. Strand Sequencing can involve the use of a nucleotide handling enzyme, such as Phi29 DNA polymerase, to control the movement of the polynucleotide through the pore. Nanopore sequencing, using enzymes to control the translocation of dsDNA through the nanopore, has in the past focused on only reading one strand of a dsDNA construct. When the enzyme is used as polymerase, the portion to be sequenced is single stranded. This is fed through the nanopore and the addition of dNTPs at a primer/template junction on top of the strand pulls the single stranded portion through the nanopore in a controlled fashion. The majority of the published literature uses this approach to control strand movement (Lieberman et al. (2010) "Processive Replication of Single DNA Molecules in a Nanopore Catalyzed by phi29 DNA Polymerase" J. Am. Chem. Soc. 132(50): 17961-17972). In the polymerase mode, the complementary strand cannot be sequenced. When the enzyme is used as a double stranded exonuclease as published (Lieberman et al. (2010) supra), the unzipping of the complementary strand is accompanied by the digestion of this strand. It is therefore not possible to sequence the complementary strand with this approach. The complementary strand cannot therefore be captured and sequenced by the nanopore. Hence, only half of the DNA information in dsDNA is sequenced.

In more detail, when both polymerase and exonuclease activity are inhibited (by running without tri-phosphates bases and with excess of EDTA), enzymes such as Phi29 DNA polymerase have been shown to unzip dsDNA when pulled through a nanopore by a strong applied field (FIG. 1) (Lieberman et al. (2010) supra). This has been termed unzipping mode. Unzipping mode implies that it is the unzipping of dsDNA above or through the enzyme, and importantly, it is the requisite force required to disrupt the interactions of both strands with the enzyme and to overcome the hydrogen bonds between the hybridised strands. In the past the second complementary strand was considered to be essential for efficient enzyme binding. In addition, it was thought that the requisite force required to unzip the strand above or in the enzyme was a dominant braking effect slowing DNA through the pore. Herein we describe how enzymes such as Phi29 DNA polymerase can act as a molecular brake for ssDNA, enabling sufficient controlled movement through a nanopore for sequencing around the hairpin turns of specially designed dsDNA constructs to sequence both the sense and anti-sense strands of dsDNA (FIG. 2). Unzipping mode has in the past predominantly been performed using templates where the distal part of the analyte is blunt ended (FIG. 1). Small hairpins have occasionally been used, but were only included to simplify DNA design. Previous work has not considered the use of hairpins on long dsDNA to provide the ability to read both strands. This is because the unzipping movement model has not considered Phi29 DNA polymerase or related enzymes capable of controlling the movement of the DNA when entering ssDNA regions (i.e. when moving around the hairpin and along the anti-sense strand—FIG. 2).

SUMMARY OF THE INVENTION

The inventors have surprisingly demonstrated that both strands of a double stranded target polynucleotide can be sequenced by a nanopore when the two strands are linked by a bridging moiety and then separated. Furthermore, the inventors have also surprisingly shown that an enzyme, such as Phi29 DNA polymerase, is capable of separating the two strands of a double stranded polynucleotide, such as DNA, linked by a bridging moiety and controlling the movement of the resulting single stranded polynucleotide through the transmembrane pore.

The ability to sequence both strands of a double stranded polynucleotide by linking the two strands with a bridging moiety has a number of advantages, not least that both the sense and anti-sense strands of the polynucleotide can be sequenced. These advantages are discussed in more detail below.

Accordingly, the invention provides a method of sequencing a double stranded target polynucleotide, comprising:
(a) providing a construct comprising the target polynucleotide, wherein the two strands of the target polynucleotide are linked at or near one end of the target polynucleotide by a bridging moiety;
(b) separating the two strands of the target polynucleotide to provide a single stranded polynucleotide comprising one strand of the target polynucleotide linked to the other strand of the target polynucleotide by the bridging moiety;
(c) moving the single stranded polynucleotide through a transmembrane pore such that a proportion of the nucleotides in the single stranded polynucleotide interact with the pore; and
(d) measuring the current passing through the pore during each interaction and thereby determining or estimating the sequence of the target polynucleotide,
wherein the separating in step (b) comprises contacting the construct with a polynucleotide binding protein which separates the two strands of the target polynucleotide.

The invention also provides:
a kit for preparing a double stranded target polynucleotide for sequencing comprising (a) a bridging moiety capable of linking the two strands of the target polynucleotide at or near one end and (b) at least one polymer,
a method of preparing a double stranded target polynucleotide for sequencing, comprising:
(a) linking the two strands of the target polynucleotide at or near one end with a bridging moiety; and
(b) attaching one polymer to one strand at the other end of the target polynucleotide and thereby forming a construct that allows the target polynucleotide to be sequenced using a transmembrane pore;
a method of sequencing a double stranded target polynucleotide, comprising:
(a) providing a construct comprising the target polynucleotide, wherein the two strands of the target polynucleotide are linked at or near one end of the target polynucleotide by a bridging moiety;
(b) separating the two strands of the target polynucleotide to provide a single stranded polynucleotide comprising one strand of the target polynucleotide linked to the other strand of the target polynucleotide by the bridging moiety;
(c) synthesising a complement of the single stranded polynucleotide, such that the single stranded polynucleotide and complement form a double stranded polynucleotide;
(d) linking the two strands of the double stranded polynucleotide at or near one end of the double stranded polynucleotide using a bridging moiety;
(e) separating the two strands of the double stranded polynucleotide to provide a further single stranded polynucleotide comprising the original single stranded polynucleotide linked to the complement by the bridging moiety;
(f) moving the complement through a transmembrane pore such that a proportion of the nucleotides in the complement interact with the pore; and
(g) measuring the current passing through the pore during each interaction and thereby determining or estimating the sequence of the target polynucleotide, wherein the separating in step (e) comprises contacting the construct with a polynucleotide binding protein which separates the two strands of the target polynucleotide;
an apparatus for sequencing a double stranded target polynucleotide, comprising: (a) a membrane; (b) a plurality of transmembrane pores in the membrane; (c) a plurality of polynucleotide binding proteins which are capable of separating the two strands of the target polynucleotide; and (d) instructions for carrying out the method of the invention; and
an apparatus for sequencing a double stranded target polynucleotide, comprising: (a) a membrane; (b) a plurality of transmembrane pores in the membrane; and (c) a plurality of polynucleotide binding proteins which are capable of separating the two strands of the target polynucleotide, wherein the apparatus is set up to carry out the method of the invention.

DESCRIPTION OF THE FIGURES

FIG. 4 shows a schematic of the DNA-Enzyme-nanopore complex (left) sequenced in unzipping mode through MspA nanopores using Phi29 DNA polymerase, and the consensus sequence obtained from them (right). Section 1 marks the sense section of DNA, and section 2 marks the anti-sense section. This figure shows DNA sequencing of a short dsDNA construct. In this construct the dsDNA section is not connected by a hairpin, so the enzyme falls off the end of the DNA, and only the template/sense strand is sequenced (except for the last ~20 bases).

FIG. 5 shows a schematic of the DNA-Enzyme-nanopore complex (left) sequenced in unzipping mode through MspA nanopores using Phi29 DNA polymerase, and the consensus sequence obtained from them (right). Section 1 marks the sense section of DNA, and section 2 the anti-sense section. DNA sequencing of a short dsDNA construct with a hairpin. In this construct the enzyme moves along the sense strand, around the hairpin loop, and down the anti-sense strand, permitting sequencing of both the sense and the first part of the anti-sense strand.

FIG. 6 shows a schematic of the DNA-Enzyme-nanopore complex (left) sequenced in unzipping mode through MspA nanopores using Phi29 DNA polymerase, and the consensus sequence obtained from them (right). Section 1 marks the sense section of DNA, and section 2 the anti-sense section. Similar to FIG. 5, this construct permits sequencing of both the sense and anti-sense strands, but the additional 3'-ssDNA overhang permits reading of the full length of the anti-sense strand before the enzyme falls off the end of the DNA.

FIG. 7 shows a schematic of the DNA-Enzyme-nanopore complex (left) sequenced in unzipping mode through MspA nanopores using Phi29 DNA polymerase, and the consensus sequence obtained from them (right). Section 1 marks the sense section of DNA, and section 2 the anti-sense section. Similar to FIG. 5, this construct permits sequencing of both the sense and anti-sense strands, however, this construct has a single abasic residue (shown as a cross) in the hairpin, which provides a clear marker in the DNA sequence to identify the sense and anti-sense sect ions.

DESCRIPTION OF THE SEQUENCE LISTING

Figure 1:
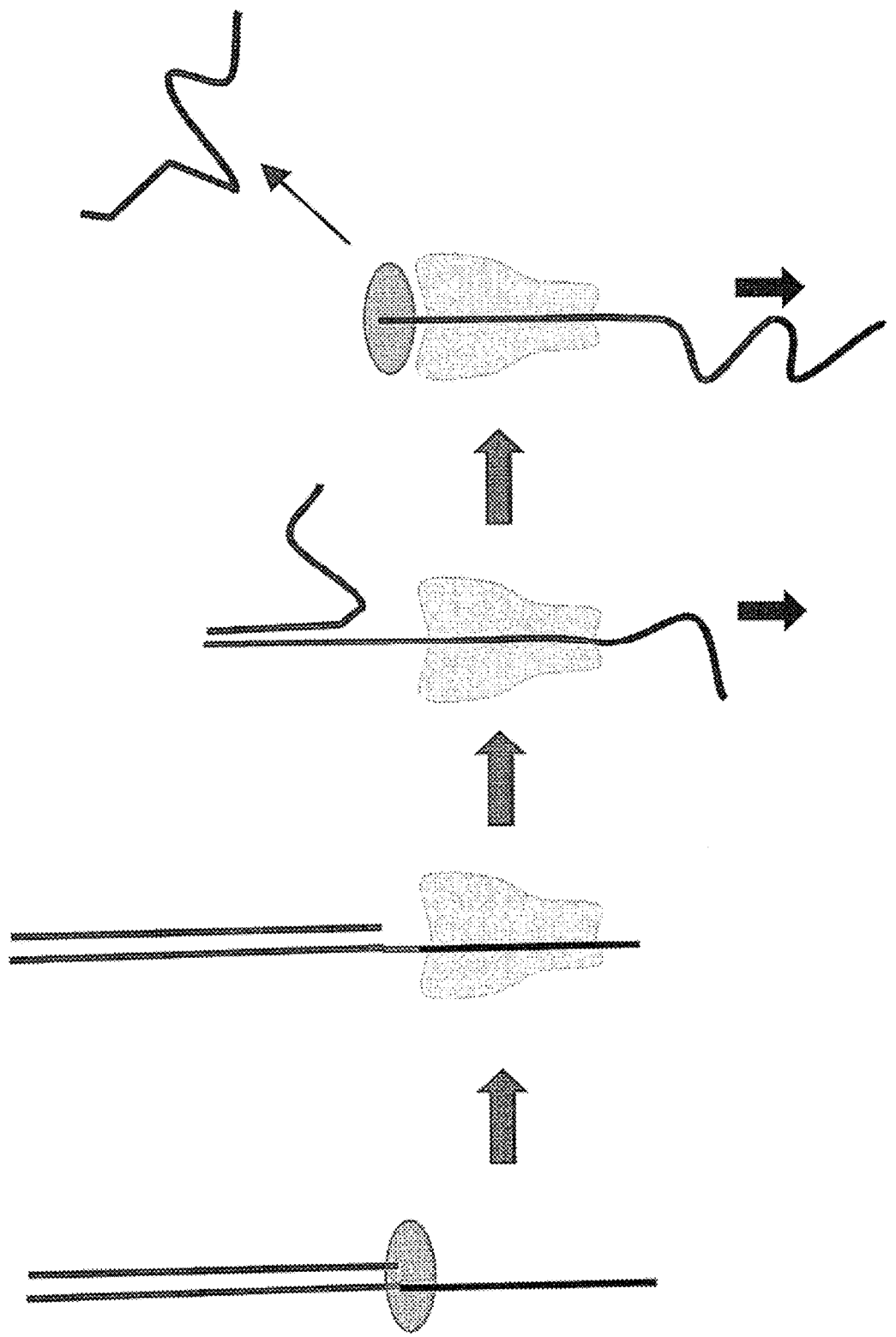
FIG. 1 shows a schematic of enzyme controlled dsDNA and ssDNA translocation through a nanopore. An enzyme (e.g. Phi29 DNA polymerase) that is incubated with dsDNA having an ssDNA leader binds at the ssDNA-dsDNA interface. DNA-enzyme complexes are captured by a nanopore under an applied field. Under the field, the template strand of the DNA is slowly stripped through the enzyme in a controlled base-by-base manner, in the process unzipping the complementary primer strand of the dsDNA in or above the enzyme. Once the enzyme reaches the end of the dsDNA it falls off the DNA, releasing it through the nanopore.
Figure 2:
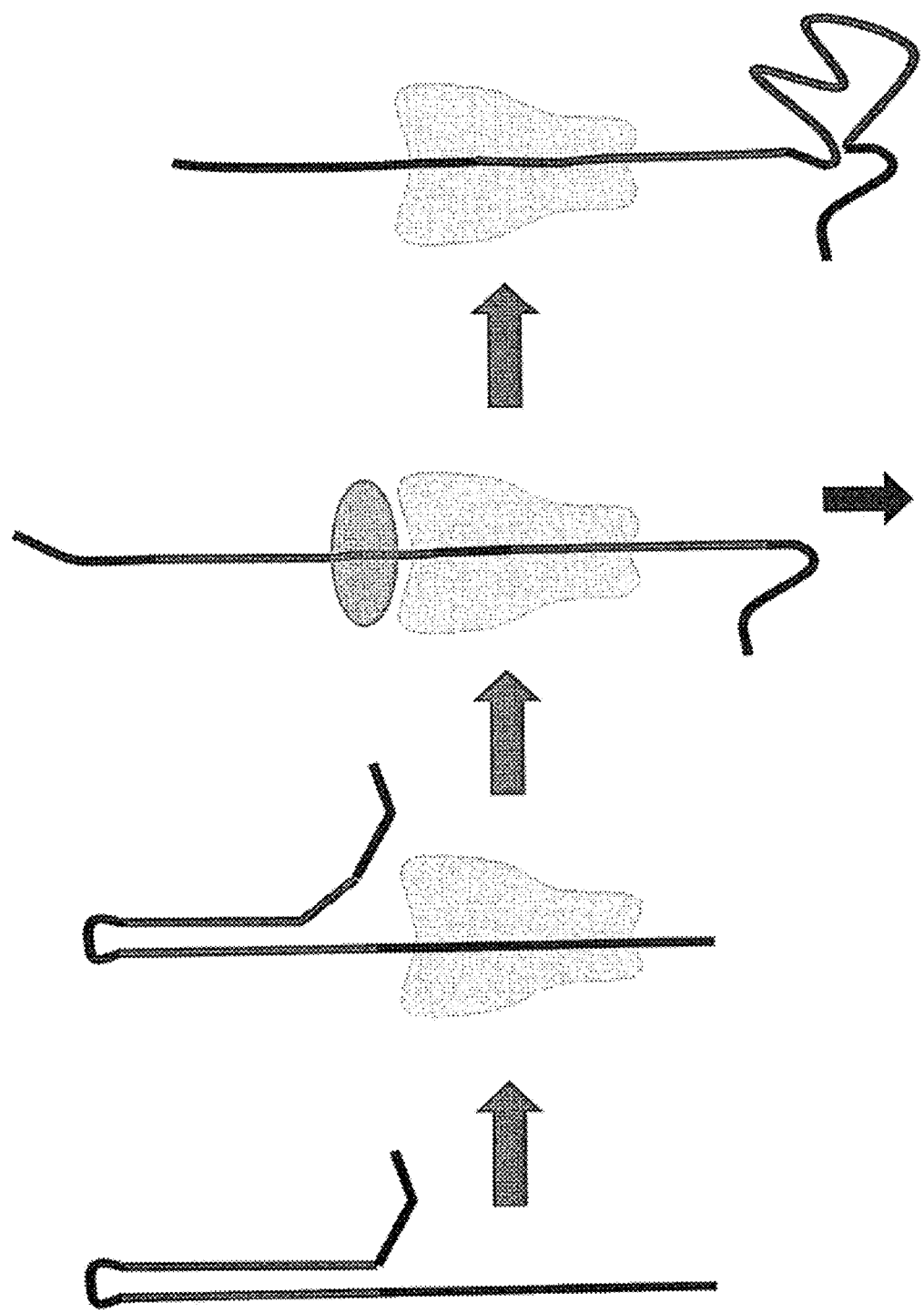
FIG. 2 shows another schematic of enzyme controlled dsDNA and ssDNA translocation through a nanopore. The dsDNA has a hairpin turn linking the sense and anti-sense strands of the dsDNA. Once the enzyme reaches the hairpin it remain bound to the DNA, proceeds around the hairpin turn, and along the anti-sense strand. In the hairpin and antisense regions the enzyme functions as an ssDNA molecular brake, continuing to sufficiently control translocation of the DNA through the nanopore to sequence the DNA.

SEQ ID NO: 1 shows the codon optimised polynucleotide sequence encoding the NNN-RRK mutant MspA monomer.

SEQ ID NO: 2 (also referred to as "B1") shows the amino acid sequence of the mature form of the NNN-RRK mutant of the MspA monomer. The mutant lacks the signal sequence and includes the following mutations: D90N, D91N, D93N, D118R, D134R and E139K. These mutations allow DNA transition through the MspA pore.

SEQ ID NO: 3 shows the polynucleotide sequence encoding one subunit of α-hemolysin-E111N/K147N (α-HL-NN; Stoddart et al., PNAS, 2009; 106(19): 7702-7707).

SEQ ID NO: 4 shows the amino acid sequence of one subunit of α-HL-NN.

SEQ ID NO: 5 shows the codon optimised polynucleotide sequence encoding the Phi29 DNA polymerase.

SEQ ID NO: 6 shows the amino acid sequence of the Phi29 DNA polymerase.

SEQ ID NOs: 7 to 9 show the amino acid sequences of the mature forms of the MspB, C and D mutants respectively. The mature forms lack the signal sequence.

SEQ ID NOs.: 10 to 15 show the sequences used to illustrate homopolymer reads.

SEQ ID NOs: 16 to 36 show the sequences used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a nucleic acid sequence" includes two or more such sequences, and the like.

All publications, patents and patent applications cited herein, whether supra or infra, are hereby incorporated by reference in their entirety.

Methods of the Invention

The invention provides a method for sequencing a double stranded target polynucleotide. The method comprises linking the two strands of the target polynucleotide by a bridging moiety. The two strands of the target polynucleotide are separated to provide a single stranded polynucleotide by contacting the construct comprising the target polynucleotide with a polynucleotide binding protein. The single stranded polynucleotide is moved through a transmembrane pore. A proportion of the nucleotides in the single stranded polynucleotide interact with the pore. The current passing through the pore is measured during each interaction and the sequence of the target polynucleotide is estimated or determined. The target polynucleotide is therefore sequenced using Strand Sequencing. This method may be referred to herein as the "MONO" method.

As discussed above, linking the two strands of the target polynucleotide by a bridging moiety allows both strands of the target polynucleotide to be sequenced by the transmembrane pore. This method is advantageous because it doubles the amount of information obtained from a single double stranded target polynucleotide construct. Moreover, because the sequence in the complementary 'anti-sense' strand is necessarily orthogonal to the sequence of the 'sense' strand, the information from the two strands can be combined informatically. Thus, this mechanism provides an orthogonal proof-reading capability that provides higher confidence observations.

Furthermore, the other major advantages of the method of the invention are:

1) Coverage of missed nucleotides: the method substantially minimises issues of any missed nucleotides or groups of nucleotides (e.g. due to movement issues such as the strand slipping through the pore), since any states that might be missed in one strand are likely to be covered by the orthogonal information obtained from its complement region.

2) Coverage of problematic sequence motifs: any difficult to sequence motifs are covered by the orthogonal and opposite information in the complementary strand, which having a different sequence will not have the same sequence dependent issues. For example, this is particularly relevant for sequence motifs that produce only small changes in current, or have similar current levels—i.e. consecutive base motifs that when moved through the nanopore produce the same current block, and are therefore not observed as there is no step change in current. Any similar current levels from one sequence motif will be covered by the entirely different current levels obtained from its orthogonal sequence in the complement strand.

In addition to the advantages discussed above there are a number of special cases where the concept of reading both strands of the double stranded polynucleotide can be utilized to provide further benefits.

1. Epigenetic Information

Being able to identify epigenetic information (such as 5-methylcytosine of 5-hydroxymenthylcytosine nucleotides) or damaged bases within a natural DNA strand is desirable in a wide range of applications. At present, it is difficult to extract this information as the majority of DNA sequencing technologies rely on DNA amplification as part of their sequencing chemistry. This information can be extracted, but requires chemical treatment followed by amplification, both of which can introduce errors.

Nanopore sequencing is also a single molecule sequencing technology and therefore can be performed without the need of DNA amplification. It has been shown that nanopores can detect modifications to the standard four DNA nucleotides. Reading both strands of the polynucleotide can be useful in detecting DNA modifications in situations where a modified base behaves in a similar way (generates a similar current signal) to another base. For example if methylcytosine (mC) behaves in a similar way to thymidine there is an error associated with assigning a mC to a T. In the sense strand, there is a probability of the base being called a mC or a T. However, in the anti-sense strand, the corresponding base may appear as a G with a high probability. Thus by "proof reading" the anti-sense strand, it is highly likely that the base in the sense strand was a mC rather than a T.

Figure 15:
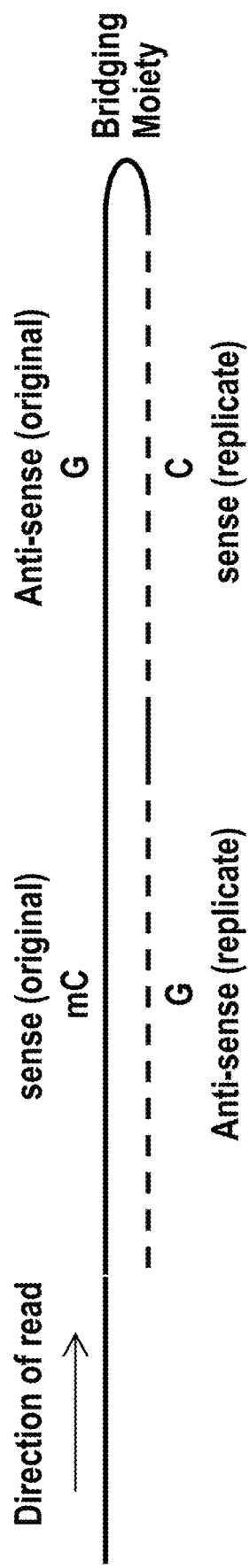
FIG. 15 shows where amplification may be added as part of the sample preparation to aid the detection of epigenetic information. A nucleotide has been constructed so that the following information is read through the pore: sense (original), antisense (original), bridging moiety, sense (replicate), antisense (replicate). Information on the methylated base (mC) is therefore obtained four times.

Reading the sense and the anti-sense strand can be performed without the need of amplification or replication. However, amplification or replication may be added as part of the sample preparation to aid the detection of epigenetic information. A nucleotide strand may be constructed (described in detail below) where the following information is read through the nanopore in the following order: sense (original), antisense (original), -bridging moiety-, sense (complement), antisense (complement) (FIG. 15).

In this scheme, information on the methylated base will be obtained four times. If the epigenetic base is in the original sense strand (in this case, mC), the following information will be obtained with a high probability: sense (original)—mC, anti-sense (original)—G, sense (complement)—C, and anti-sense (compliment)—G. It is clear that the original sense read and the replicated sense read will give different results, while the both anti-sense reads will yield the same base call. This information can be used to indicate the position of the epigenetic base in the original sense strand.

2. RNA-DNA Double Reads

Figure 16:
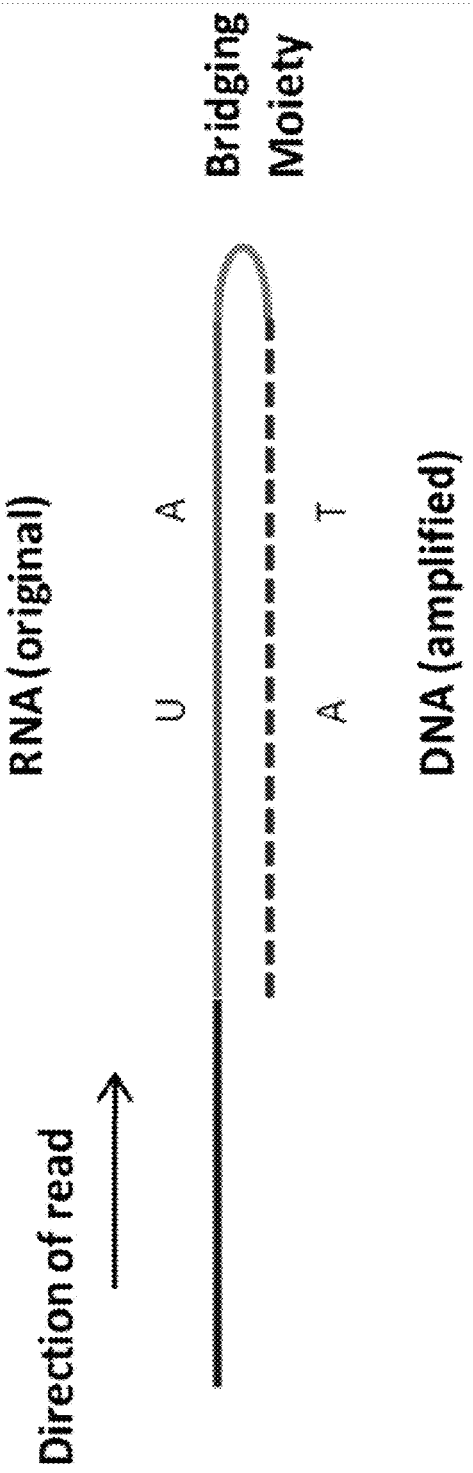
FIG. 16 shows how RNA can be sequenced. A bridging moiety is attached to a piece of RNA and the DNA reverse complement added to the RNA via a reverse transcriptase. The RNA is read, followed by the DNA of the reverse complement.

A similar scheme can be used to sequence RNA. A bridging moiety can be attached to a piece of RNA and the DNA reverse complement added to the RNA via a reverse transcriptase (resulting construct shown in FIG. 16)

In this scheme, the RNA is read followed by a DNA read of the reverse complement. Information from both the RNA and the DNA reads can be combined to increase the accuracy of determining or estimating the RNA sequence. For example, if a uracil base (U) in RNA gives a similar read to a cytosine, then the corresponding base could be used to resolve this error. If the corresponding DNA base is G, then it is highly likely that the RNA base was a C, however if the DNA base is called as an A, then it is likely that the RNA base was a U.

3. Homopolymer Reads

Homopolymer reads may be a problem for single molecule nanopore sequencing. If the homopolymer region is longer than the reading section of the pore, the length of the homopolymer section will be difficult to determine.

It has already been shown that Phi29 can be used to read around a hairpin, allowing the sense and the antisense strand to be read. Amplification can be used to generate the antisense strand using a polymerase and a set of regular DNA triphosphates; dTTP, dGTP, dATP, dCTP. To overcome the problem of homopolymer reads, the antisense strand can be synthesised with the addition of a different base in combination with the original dTTP, dGTP, dATP, dCTP. This could be a natural base analogue such as inosine (I). The base will have a random chance of incorporating compared to the correct natural base and the insertion rates can be controlled by varying the concentration of the triphosphate species.

Through the addition of the alternative base, there will be a probability of an alternative base being inserted into the reverse complement of a homopolymer region. The result of this is that the homopolymer run will be reduced in length to a point where it can be read by the reading section of the nanopore. For example, a homopolymer group of AAAAAAAAAAAA (SEQ ID NO: 10) will have random insertions of the alternative base and may give TTTITIIT-TTI (SEQ ID NO: 11) (where I is inosine).

```
Original DNA + Hairpin (SEQ ID NO: 12):
5'-TTTTTTTTTTTTTTTTTTTTXXXXXTGTACTGCCGTACGTAAAAAAA

TAGCTGATCGTACTTACTAGCATGTT
```

```
Regular Conversion (SEQ ID NO: 13):
5'-TTTTTTTTTTTTTTTTTTTXXXXXTGTACTGCCGTACGTAAAAAA

TAGCTGATCGTACTTACATGACGGCATGCATTTTTTATCGACTAGCATG

TT

Proposed Scheme 1 (G, T, A, C is randomly
replaced by analogue I) (SEQ ID NO 14):
5'-TTTTTTTTTTTTTTTTTTTXXXXXTGTACTGCCGTACGTAAAAAA

TAGCTGATCGTACTTAIATIACGICATGIATTITTITATIGACTAGCATG

TT
(abasic = X)
```

The base analogue could be generic (replace T, G, A, or C), or it could be specific to one base (e.g. deoxyuridine (U) just replaces T).

```
Proposed Scheme 2 (T is randomly replaced
by analogue U) (SEQ ID NO: 15):
5'-TTTTTTTTTTTTTTTTTTTXXXXXTGTACTGCCGTACGTAAAAAA

TAGCTGATCGTACTTACAUGACGGCATGCAUTTTUTTATCGACTAGCATG

TT
(abasic = X)
```

In both scheme one and two, the homopolymer stretch has been reduced to allow individual nucleotides or groups of nucleotides to be estimated or determined. The sense strand will be a natural DNA strand, while the anti-sense will contain a mixture of natural bases and base analogues. The combination of data from the sense and the antisense reads can be used to estimate the length of the homopolymer run in the original DNA section.

Double Stranded Target Polynucleotide

The method of the invention is for sequencing a double stranded polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. The nucleotide can be oxidized or methylated. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (COP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, CMP, UMP, dAMP, dTMP, dGMP or dCMP.

A nucleotide may contain a sugar and at least one phosphate group (i.e. lack a nucleobase).

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea, coffee.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

If the target polynucleotide is coupled to the membrane as discussed in more detail below, the method of the invention is particularly advantageous for human DNA sequencing because only small amounts of purified DNA can be obtained from human blood. The method preferably allows sequencing of a target polynucleotide that is present at a concentration of from about 0.1 pM to about 1 nM, such as less than 1 pM, less than 10 pM or less than 100 pM.

Construct

The method of the invention involves providing a construct comprising the double stranded target nucleotide to be sequenced. The construct typically allows both strands of the target polynucleotide to be sequenced by a transmembrane pore.

The construct comprises a bridging moiety which is capable of linking the two strands of the target polynucleotide. The bridging moiety typically covalently links the two strands of the target polynucleotide. The bridging moiety can be anything that is capable of linking the two strands of the target polynucleotide, provided that the bridging moiety does not interfere with movement of the single stranded polynucleotide through the transmembrane pore. Suitable bridging moieties include, but are not limited to a polymeric linker, a chemical linker, a polynucleotide or a polypeptide. Preferably, the bridging moiety comprises DNA. RNA, modified DNA (such as abasic DNA), RNA, PNA, LNA or PEG. The bridging moiety is more preferably DNA or RNA.

The bridging moiety is most preferably a hairpin loop. The hairpin loop is typically 4 to 100 nucleotides in length, preferably 4 to 8 nucleotides in length.

The bridging moiety is linked to the target polynucleotide construct by any suitable means known in the art. The bridging moiety may be synthesized separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide.

The construct comprising the target polynucleotide also preferably comprises at least one polymer at the opposite end of the target polynucleotide to the bridging moiety. Such polymer(s) aid the sequencing method of the invention as discussed in more detail below. Suitable polymers include polynucleotides (DNA/RNA), modified polynucleotides such as modified DNA, PNA, LNA, PEG or polypeptides.

The construct preferably comprises a leader polymer. The leader polymer is linked to the target polynucleotide at the opposite end to the bridging moiety. The leader polymer helps the double stranded target polynucleotide to engage with the transmembrane pore or with a polynucleotide binding protein, such as Phi29 DNA polymerase, that helps to separate the two strands and/or controls the movement of the single stranded polynucleotide through the pore. Transmembrane pores and polynucleotide binding proteins are discussed in more detail below.

The leader polymer can be a polynucleotide such as DNA or RNA, a modified polynucleotide (such as abasic DNA), PNA, LNA, PEG or a polypeptide. The leader polymer is preferably a polynucleotide and is more preferably a single stranded polynucleotide. The leader polymer can be any of the polynucleotides discussed above. The single stranded leader polymer is most preferably a single strand of DNA. The leader polymer can be any length, but is typically 27 to 150 nucleotides in length, such as from 50 to 150 nucleotides in length.

The addition of sections of single stranded polynucleotide to a double stranded polynucleotide can be performed in various ways. A chemical or enzymatic ligation can be done. In addition, the Nextera method by Epicentre is suitable. The inventors have developed a PCR method using a sense primer that, as usual contains a complementary section to the start of the target region of genomic DNA, but was additionally preceded with a 50 polyT section. To prevent the polymerase from extending the complementary strand opposite the polyT section and thereby create a blunt ended PCR product (as is normal), four abasic sites were added between the polyT section and the complimentary priming section. These abasic sites will prevent the polymerase from extending beyond this region and so the polyT section will remain as 5' single stranded DNA on each of the amplified copies. Other possible modifications which could also stop polymerase extension include RNA, PNA or morpholino bases, iso-dC or iso-dG.

The construct preferably further comprises a polymer tail (also linked to the target polynucleotide at the opposite end to the bridging moiety). The polymer tail aids sequencing of the target construct by the transmembrane pore. In particular, the polymer tail typically ensures that the entirety of the double stranded polynucleotide (i.e. all of both strands) can be read and sequenced by the transmembrane pore. As discussed below, polynucleotide binding proteins, such as Phi29 DNA polymerase, can control the movement of the single stranded polynucleotides through the transmembrane pore. The protein typically slows the movement of the polynucleotide through the pore. For instance. Phi29 DNA polymerase acts like a brake slowing the movement of the polynucleotide through the pore along the potential applied across the membrane. Once the polynucleotide is no longer in contact with the binding protein, it is free to move through the pore at such a rate that sequence information is difficult to obtain. Since there is normally a short distance from the protein to the pore, typically approximately 20 nucleotides some sequence information (approximately equal to that distance) may be missed. A tail polymer "extends" the length of the single stranded polynucleotide such that its movement may be controlled by the nucleic acid binding protein while all of both strands of the target polynucleotide pass through the pore and are sequenced. Such embodiments ensure that sequence information can be obtained from the entirety of both strands in the target polynucleotide. The tail polymer may also provide a site for a primer to bind, which allows the nucleic acid binding protein to separate the two strands of the target polynucleotide.

The tail polymer can be a polynucleotide such as DNA or RNA, a modified polynucleotide (such as abasic DNA), PNA, LNA, PEG or a polypeptide. The tail polymer is preferably a polynucleotide and is more preferably a single stranded polynucleotide. The tail polymer can be any of the polynucleotides discussed above.

The construct preferably also comprises one or more markers, which result in a distinctive current (characteristic signature current) when passed through the transmembrane pore. The markers are typically used to allow the position of the single stranded polynucleotide in relation to the pore to be estimated or determined. For instance, the signal from a marker positioned between both strands of the target polynucleotide indicates that one strand has been sequenced and the other is about to enter the pore. Hence, such markers can be used to differentiate between the sense and anti-sense strands of target DNA. The marker(s) may also be used to identify the source of the target polynucleotide. Suitable markers include, but are not limited to abasic regions, specific sequences of nucleotides, unnatural nucleotides, fluorophores or cholesterol. The markers are preferably an abasic region or a specific sequence of nucleotides.

The marker(s) may be positioned anywhere in the construct. The marker(s) can be positioned in the bridging moiety. The marker(s) can also be positioned near the bridging moiety. Near the bridging moiety preferably refers to within 10 to 100 nucleotides of the bridging moiety.

The markers can also be positioned within the leader polymer or the tail polymer.

The construct may be coupled to the membrane using any known method. If the membrane is an amphiphilic layer, such as a lipid bilayer (as discussed in detail below), the construct is preferably coupled to the membrane via a polypeptide present in the membrane or a hydrophobic anchor present in the membrane. The hydrophobic anchor is preferably a lipid, fatty acid, sterol, carbon nanotube or amino acid.

The construct may be coupled directly to the membrane. The construct is preferably coupled to the membrane via a linker. Preferred linkers include, but are not limited to, polymers, such as polynucleotides, polyethylene glycols (PEGs) and polypeptides. If a polynucleotide is coupled directly to the membrane, then some sequence data will be lost as the sequencing run cannot continue to the end of the polynucleotide due to the distance between the membrane and the detector. If a linker is used, then the polynucleotide can be processed to completion. If a linker is used, the linker may be attached to the construct at any position. The linker is preferably attached to the polynucleotide at the tail polymer.

The coupling may be stable or transient. For certain applications, the transient nature of the coupling is preferred. If a stable coupling molecule were attached directly to either the 5 or 3' end of a polynucleotide, then some sequence data will be lost as the sequencing run cannot continue to the end of the polynucleotide due to the distance between the bilayer and the enzymes active site. If the coupling is transient, then when the coupled end randomly becomes free of the bilayer, then the polynucleotide can be processed to completion. Chemical groups that form stable or transient links with the membrane are discussed in more detail below. The construct may be transiently coupled to an amphiphilic layer or lipid bilayer using cholesterol or a fatty acyl chain. Any fatty acyl chain having a length of from 6 to 30 carbon atoms, such as hexadecanoic acid, may be used.

In preferred embodiments, construct is coupled to an amphiphilic layer such as a lipid bilayer. Coupling of polynucleotides to synthetic lipid bilayers has been carried out previously with various different tethering strategies. These are summarised in Table 1 below.

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules," *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer with a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

Separating

The two strands of the target polynucleotide are separated using a polynucleotide binding protein.

The polynucleotide binding protein is preferably derived from a polynucleotide handling enzyme. However, the enzyme may be used under conditions in which is does not catalyze a reaction. For instance, a protein derived from Phi29 DNA polymerase may be run in an unzipping mode as discussed in more detail below.

A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and preferably controlling its movement through the pore. For instance, the enzyme may be modified to remove its enzymatic activity or may be used under conditions which prevent it from acting as an enzyme. Such conditions are discussed in more detail below.

The polynucleotide binding protein is typically derived from the Picovirinae virus family. Suitable viruses include, but are not limited to, AHJD-like viruses and Phi29 like viruses. The polynucleotide binding protein is preferably derived front Phi29 DNA polymerase or a helicase.

A protein derived from Phi29 DNA polymerase comprises the sequence shown in SEQ ID NO: 6 or a variant thereof. Wild-type Phi29 DNA polymerase has polymerase and exonuclease activity. It may also unzip double stranded polynucleotides under the correct conditions. Hence, the enzyme may work in three modes. This is discussed in more detail below. A variant of SEQ ID NOs: 6 is an enzyme that has an amino acid sequence which varies from that of SEQ ID NO: 6 and which retains polynucleotide binding activity. The variant must work in at least one of the three modes discussed below. Preferably, the variant works in all three modes. The variant may include modifications that facilitate handling of the polynucleotide and/or facilitate its activity at high salt concentrations and/or room temperature. The variant may include Fidelity Systems' TOPO modification, which improves enzyme salt tolerance.

Over the entire length of the amino acid sequence of SEQ ID NO: 6, a variant will preferably be at least 40% homologous to that sequence based on amino acid identity. More preferably, the variant polypeptide may be at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described below. The variant may differ from the wild-type sequence in any of the ways discussed below with reference to SEQ ID NO: 2. The enzyme may be covalently attached to the pore as discussed below.

The method is preferably carried out using the protein derived from Phi29 DNA polymerase in unzipping mode. In this embodiment, steps (b), (c) and (d) are carried out in the absence of free nucleotides and the absence of an enzyme cofactor such that the polymerase controls the movement of the single stranded polynucleotide through the pore with the field resulting from the applied voltage (as it is unzipped). In this embodiment, the polymerase acts like a brake preventing the single stranded polynucleotide from moving through the pore too quickly under the influence of the applied voltage. The method preferably further comprises (e) lowering the voltage applied across the pore such that the single stranded polynucleotide moves through the pore in the opposite direction to that in steps (c) and (d) (i.e. as it re-anneals) and a proportion of the nucleotides in the polynucleotide interacts with the pore and (f) measuring the current passing through the pore during each interaction and thereby proof reading the sequence of the target polynucleotide obtained in step (d), wherein steps (e) and (f) are also carried out with a voltage applied across the pore.

The two strands of the target polynucleotide can be separated and duplicated at any stage before sequencing is carried out and as many times as necessary. For example, after separating the two strands of a first target polynucleotide construct as described above, a complementary strand to the resulting single stranded polynucleotide can be generated to form another double stranded polynucleotide. The two strands of this double stranded polynucleotide can then be linked using a bridging moiety to form a second construct. This may be referred to herein as the "DUO" method. This construct may then be used in the invention. In such an embodiment, one strand of the double stranded polynucleotide in the resulting construct contains both strands of the original target double stranded polynucleotide (in the first construct) linked by a bridging moiety. The sequence of the original target double stranded polynucleotide or the complement strand can be estimated or determined. This process of replication can be repeated as many times as necessary and provides additional proof reading as the target polynucleotide is in effect being read multiple times.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub units do not possess. Block copolymers can be engineered such that one of the monomer sub units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompasses a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The amphiphilic molecules may be chemically-modified or functionalised to facilitate coupling of the analyte.

The amphiphilic layer may be a monolayer or a bilayer. The amphiphilic layer is typically planar. The amphiphilic layer may be non-planar such as curved.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB081000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647).

Transmembrane Pore

A transmembrane pore is a structure that permits hydrated ions driven by an applied potential to flow from one side of the membrane to the other side of the membrane.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7 or 8 subunits. The pore is more preferably a heptameric or octameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smeg-*

*matis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-IIL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. The pore may also comprise one or more constructs which comprise two or more covalently attached monomers derived from Msp. Suitable pores are disclosed in U.S. Provisional Application No. 61/441,718 (filed 11 Feb. 2011). Preferably the pore is derived from MspA or a homolog or paralog thereof.

A monomer derived from Msp comprises the sequence shown in SEQ ID NO: 2 or a variant thereof. SEQ ID NO: 2 is the NNN-RRK mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Preferred variants are disclosed in International Application No. PCT/GB2012050301 (claiming priority from U.S. Provisional Application No. 61/441,718). Particularly preferred variants include, but are not limited to, those comprising the following substitution(s): L88N; L88S; L88Q; L88T; D90S; D90Q; D90Y; I105L; I105S; Q126R; G75S; G77S; G75S, G77S, L88N and Q126R; G75S, G77S, L88N, D90Q and Q126R; D90Q and Q126R; L88N, D90Q and Q126R; L88S and D90Q; L88N and D90Q; E59R; G75Q; 075N; 075S; G75T; G77Q; 077N; G77S; G77T; I78L; S81N; T83N; N86S; N86T; I87F; I87V; I87L; L88N; L88S; L88Y; L88F; L88V; L88Q; L88T; I89F; I89V; I89L; N90S; N90Q; N90L; N90Y; N91S; N91 Q; N91L; N91M; N91I; N91A; N91V; N91G; G92A; G92S; N93S; N93A; N93T; I94L; T95V; A96R; A96D; A96V; A96N; A96S; A96T; P97S; P98S; F99S; G100S; L101F; N102K; N102S; N102T; S103A; S103Q; S103N; S103G; S103T; V104I; I105Y; I105L; I105A; I105G; I105Q; I105N; I105S; I105T; T106F; T106I; T106V; T106S; N108P; N108S; D90Q and I105A; D90S and G92S; L88T and D90S; I87Q and D90S; I89Y and D90S; L88N and I89F; L88N and I89Y; D90S and G92A; D90S and I94N; D90S and V104I; L88D and I105K; L188N and Q126R; L188N, D90Q and D91R; L88N; D90Q and D91S; L88N; D90Q and I105V; D90Q; D93S and I105A; N91 Y; N90Y and N91O; N90G and N91 Y; N90G and N91G; I05G; N90R; N91R; N90R and N91R; N90K; N91K; N90K and N91K; N90Q and N91G; N90G and N91Q; N90Q and N91Q; R118N; N91C; N90C; N90W; N91W; N90K; N91K; N90R; N91R; N90S and N91S; N90Y and I105A; N90G and I105A; N90Q and I105A; N90S and I105A; L88A and I105A; L88S and I105S; L88N and I105N; N90G and N93G; N90G; N93G; N90G and N91A; I105K; I105R; I105V; I105P; I105W; L88R; L88A; L88G; L88N; N90R and I105A; N90S and I105A; L88A and I105A; L88S and I105S; L88N and I105N; L88C; S103C; I105C; D134R.

In addition to the specific mutations discussed above, the variant may include other mutations. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (ncbi.nlm.nih.gov/).

SEQ ID NO: 2 is the NNN-RRK mutant of the MspA monomer. The variant may comprise any of the mutations in the MspB, C or D monomers compared with MspA. The mature forms of MspB. C and D are shown in SEQ ID NOs: 7 to 9. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| Ala | aliphatic, hydrophobic, neutral | Met | hydrophobic, neutral |
|---|---|---|---|
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels include, but are not limited to, fluorescent molecules, radio-isotopes, e.g. $^{125}I$, $^{35}S$, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. Suitable methods are discussed above.

The variant may include modifications that facilitate covalent attachment to or interaction with a nucleic acid binding protein. The variant preferably comprises one or more reactive cysteine residues that facilitate attachment to the nucleic acid binding protein. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may include fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of cx-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/

GB09/001690 (published as WO 2010/004273), PCT/GB09/001679 (published as WO 2010/004265) or PCT/GB10/000133 (published as WO 2010/086603).

Moving

In the method of the invention, the single stranded polynucleotide is moved through the transmembrane pore. Moving the single stranded polynucleotide through the transmembrane pore refers to moving the polynucleotide from one side of the pore to the other. Movement of the single stranded polynucleotide through the pore can be driven or controlled by potential or enzymatic action or both. The movement can be unidirectional or can allow both backwards and forwards movement.

A polynucleotide binding protein is preferably used to control the movement of the single stranded polynucleotide through the pore. This protein is preferably the same protein that separates the two strands of the polynucleotide. More preferably, this protein is Phi29 DNA polymerase. The three modes of Phi29 DNA polymerase, as discussed above, can be used to control the movement of the single stranded polynucleotide through the pore. Preferably, Phi29 DNA polymerase separates the target polynucleotide and controls the movement of the resulting single stranded polynucleotide through the transmembrane pore.

In some embodiments, the entire target polynucleotide (as a single stranded polynucleotide comprising the one strand of the target polynucleotide linked to the other strand of the target polynucleotide by the bridging moiety) will move through the pore. Thus, the entire target polynucleotide is moved through the pore and sequenced. In other embodiments, only part of the target polynucleotide moves through the pore. Such embodiments where only part of the target polynucleotide moves through the pore may be as follows:

(i) part of one strand of the target polynucleotide (for example part of the sense strand of DNA)
(ii) all of one strand of the target polynucleotide (for example all of the sense strand of DNA)
(iii) all of one strand (for example all of the sense strand of DNA) and part of the second strand (for example part of the anti-sense strand of DNA)

In embodiments where only part of one strand, or all of one strand and part of the other strand, moves through the pore it is irrelevant which of the original two strands (i.e. the sense and anti-sense strands) is fully or partially moved through the pore. Furthermore, the order of movement of the sense and antisense strands through the pore does not matter.

Figure 13:
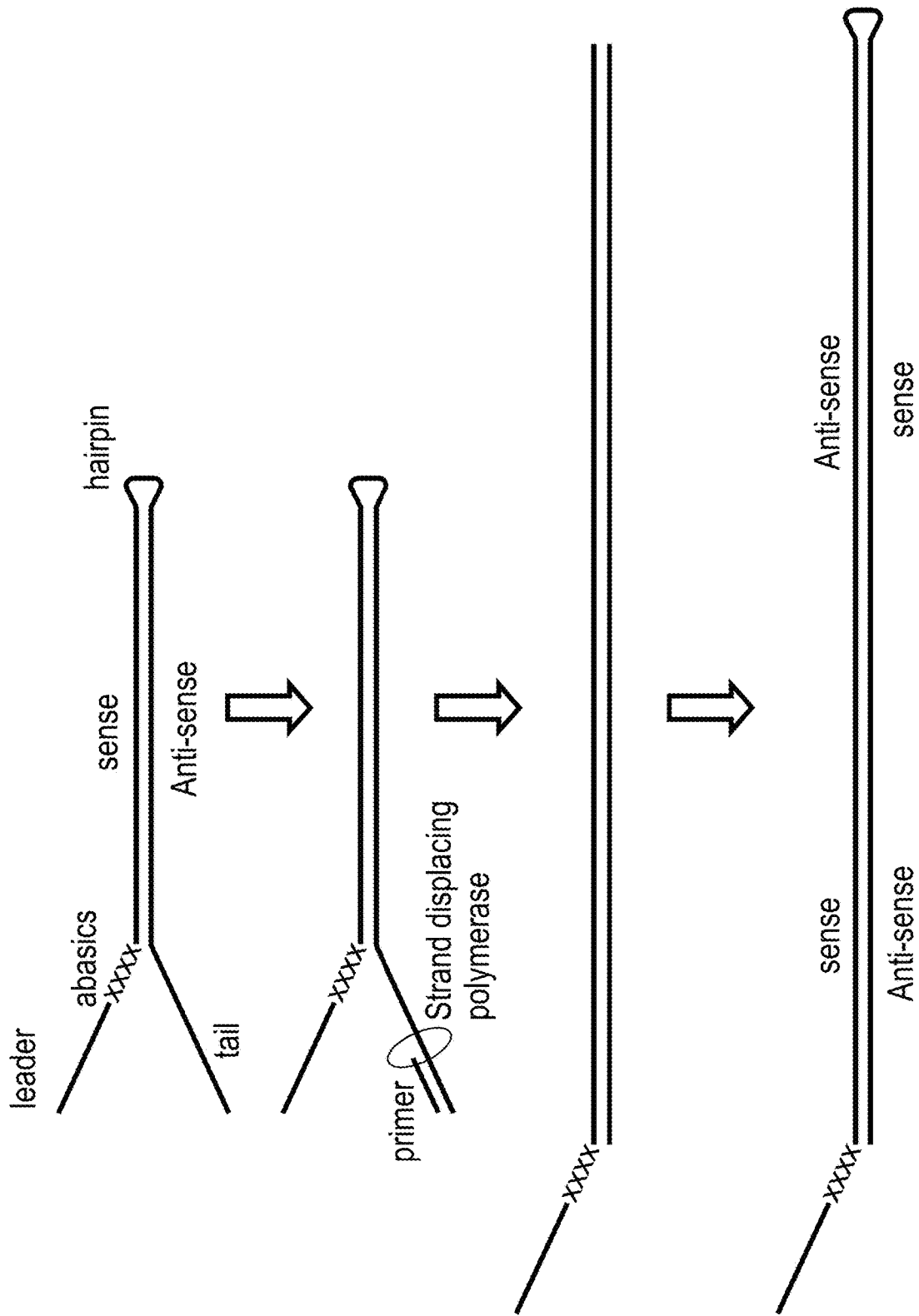
FIG. 13 shows a schematic of an alternative sample preparation for sequencing. A construct is illustrated comprising the target polynucleotide and a bridging moiety (hairpin) linking the two strands of the target polynucleotide. The construct also comprises a leader polymer (a single stranded sequence), a tail polymer (also a single stranded sequence) and an abasic marker region within the leader. The marker may prevent the enzyme from making the template completely blunt ended i.e. filling in opposite the required leader ssDNA. A strand displacing polymerase (nucleic acid binding protein) separates the two strands of the construct, initiating either via a complementary primer or by protein primed amplification from the tail polymer. A complement is generated to the resulting single stranded polynucleotide. The complement and the original sense and antisense single stranded polynucleotide analyte can be further modified by addition of a second bridging moiety (hairpin).
Figure 14:
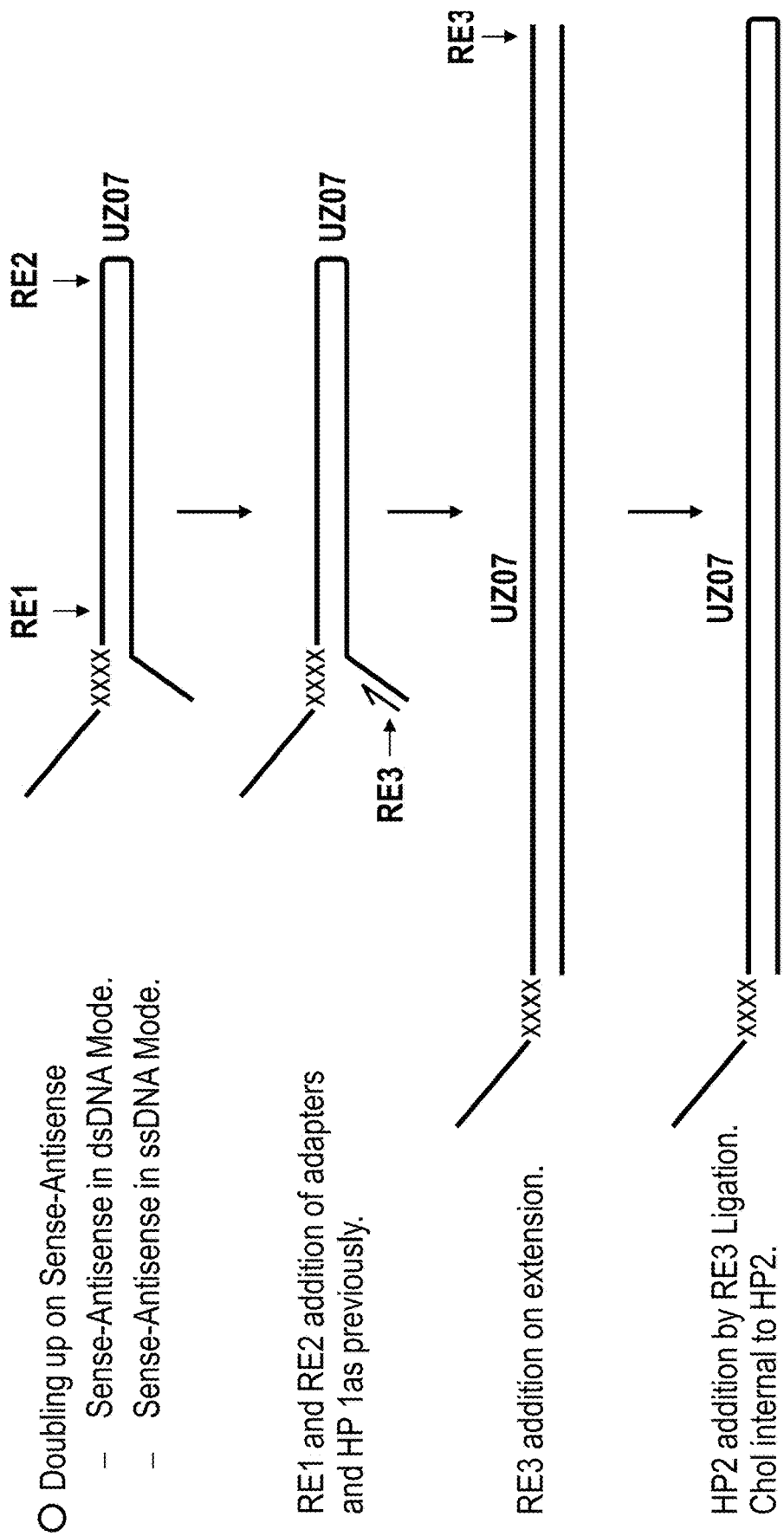
FIG. 14 shows a specific preparation of the construct comprising the target polynucleotide.

In some embodiments, as discussed above and shown in FIG. 13, after linking of the two strands of a double stranded analyte and separating the two linked strands into a single stranded target polynucleotide, a complementary strand to the single stranded target polynucleotide is generated to form a second construct. The two strands of the second construct may be linked together as described herein. The complementary strand of the second construct is then separated from the single stranded target polynucleotide. In this situation, the original single stranded target polynucleotide may move through the pore and/or the complementary strand may move through the pore. In some instances, only the complementary strand is sequenced. As described above, this process of separation and complementary strand generation can be repeated as many times as necessary. This may be referred to herein as the "DUO" method.

When the construct further comprises a leader polymer and a tail polymer, the single stranded target polynucleotide created after separating the two strands of the target polynucleotide preferably moves through the pore in the order of: (1) the leader polymer; (2) the one strand of the target polynucleotide; (3) the bridging moiety; (4) the other strand of the target polynucleotide; and (5) the tail polymer. This is an example of a sequencing a construct made according to the 'MONO' method.

In an alternative embodiment, a construct produced according to the DUO method may pass through the pore in the order of: (1) the leader polymer; (2) the first strand of the target polynucleotide; (3) the first bridging moiety; (4) the second strand of the target polynucleotide; (5) the second bridging moiety; (6) the complement of the second strand of the target polynucleotide; (7) the complement of the first bridging moiety; (8) the complement of the first strand of the target polynucleotide and (9) the tail polymer.

Methods of Sequencing a Double Stranded Target Polynucleotide

The method of the invention comprises moving the single stranded polynucleotide through a transmembrane pore such that a proportion of the nucleotides in the single stranded polynucleotide interact with the pore.

The method may be carried out using any suitable membrane as discussed above, preferably a lipid bilayer system in which a pore is inserted into a lipid bilayer. The method is typically carried out using (i) an artificial bilayer comprising a pore, (ii) an isolated, naturally-occurring lipid bilayer comprising a pore, or (iii) a cell having a pore inserted therein. The method is preferably carried out using an artificial lipid bilayer. The bilayer may comprise other transmembrane and/or intramembrane proteins as well as other molecules in addition to the pore. Suitable apparatus and conditions are discussed below with reference to the sequencing embodiments of the invention. The method of the invention is typically carried out in vitro.

The present invention provides methods of sequencing a double stranded target polynucleotide. As discussed above, a polynucleotide is a macromolecule comprising two or more pairs of nucleotides. The nucleotides may be any of those discussed above. The polynucleotide is preferably a nucleic acid.

These methods are possible because transmembrane protein pores can be used to differentiate nucleotides of similar structure on the basis of the different effects they have on the current passing through the pore. Individual nucleotides can be identified at the single molecule level from their current amplitude when they interact with the pore. The nucleotide is present in the pore if the current flows through the pore in a manner specific for the nucleotide (i.e. if a distinctive current associated with the nucleotide is detected flowing through the pore). Successive identification of the nucleotides in a target polynucleotide allows the sequence of the polynucleotide to be estimated or determined.

The method comprises (a) providing a construct comprising the target polynucleotide, wherein the two strands of the target polynucleotide are linked by the bridging moiety; (b) separating the two strands of the target polynucleotide by contacting the construct with a nucleic acid binding protein; (c) moving the resulting single stranded polynucleotide through the transmembrane pore, and (d) measuring the current passing through the pore during each interaction and thereby determining or estimating the sequence of the target polynucleotide. Hence, the method involves transmembrane pore sensing of a proportion of the nucleotides in a target polynucleotide as the nucleotides individually pass through the barrel or channel in order to sequence the target polynucleotide. As discussed above, this is Strand Sequencing.

The whole or only part of the target polynucleotide may be sequenced using this method. The polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs or 100000 or more nucleotide pairs in length. The polynucleotide can be naturally occurring or artificial. For instance, the method may be used to verify the sequence of a manufactured oligonucleotide. The methods are typically carried out in vitro.

The single stranded polynucleotide may interact with the pore on either side of the membrane. The single stranded polynucleotide may interact with the pore in any manner and at any site.

During the interaction between a nucleotide in the single stranded polynucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to determine or estimate the sequence of the target polynucleotide.

The sequencing methods may be carried out using any suitable membrane/pore system in which a pore is inserted into a membrane. The methods are typically carried out using a membrane comprising naturally-occurring or synthetic lipids. The membrane is typically formed in vitro. The methods are preferably not carried out using an isolated, naturally occurring membrane comprising a pore, or a cell expressing a pore. The methods are preferably carried out using an artificial membrane. The membrane may comprise other transmembrane and/or intramembrane proteins as well as other molecules in addition to the pore.

The membrane forms a barrier to the flow of ions, nucleotides and polynucleotides. The membrane is preferably an amphiphilic layer such as a lipid bilayer. Lipid bilayers suitable for use in accordance with the invention are described above.

The sequencing methods of the invention are typically carried out in vitro.

The sequencing methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The sequencing methods may be carried out using the apparatus described in International Application No. PCT/GB08/000562.

The methods of the invention involve measuring the current passing through the pore during interaction with the nucleotide(s). Therefore the apparatus also comprises an electrical circuit capable of applying a potential and measuring an electrical signal across the membrane and pore. The methods may be carried out using a patch clamp or a voltage clamp. The methods preferably involve the use of a voltage clamp.

The sequencing methods of the invention involve the measuring of a current passing through the pore during interaction with the nucleotide. Suitable conditions for measuring ionic currents through transmembrane protein pores are known in the art and disclosed in the Example. The method is typically carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore by using an increased applied potential.

The sequencing methods are typically carried out in the presence of any alkali metal chloride salt. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably from 150 mM to 1 M. High salt concentrations provide a high signal to noise ratio and allow for currents indicative of the presence of a nucleotide to be identified against the background of normal current fluctuations. Lower salt concentrations may be used if nucleotide detection is carried out in the presence of an enzyme. This is discussed in more detail below.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

As mentioned above, good nucleotide discrimination can be achieved at low salt concentrations if the temperature is increased. In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

The target polynucleotide being analysed can be combined with known protecting chemistries to protect the polynucleotide from being acted upon by the binding protein while in the bulk solution. The pore can then be used to remove the protecting chemistry. This can be achieved either by using protecting groups that are unhybridised by the pore, binding protein or enzyme under an applied potential (WO 2008/124107) or by using protecting chemistries that are removed by the binding protein or enzyme when held in close proximity to the pore (J Am Chem Soc. 2010 Dec. 22; 132(50):17961-72).

The Strand Sequencing method of the invention uses a polynucleotide binding protein to separate the two strands of the target polynucleotide. More preferably, the polynucleotide binding protein also controls the movement of the target polynucleotide through the pore. Examples of such proteins are given and discussed above.

The two strategies for single strand sequencing are the translocation of the single stranded polynucleotide through the transmembrane pore, both cis to trans and trans to cis, either with or against an applied potential. The most advantageous mechanism for strand sequencing is the controlled translocation of a single stranded polynucleotide through the nanopore under an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded polynucleotide can also be used in a similar manner. There are also possibilities for sequencing applications that require strand translocation against an applied potential, but the polynucleotide must be first "caught" by the enzyme under a reverse or no potential. With the potential then switched back following binding the strand will pass cis to trans through the pore and be held in an extended conformation by the current flow. The single strand polynucleotide exonucleases or single strand polynucleotide dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore.

In the most preferred embodiment, Strand Sequencing is carried out using a pore derived from Msp and a Phi29 DNA polymerase. The method comprises (a) providing the double stranded target polynucleotide construct; (b) allowing the target polynucleotide to interact with a Phi29 DNA polymerase, such that the strands are separated and the polymerase controls the movement of the target polynucleotide through the Msp pore and a proportion of the nucleotides in the target polynucleotide interacts with the pore; and (c) measuring the current passing through the pore during each interaction and thereby estimating or determining the sequence of the target polynucleotide, wherein steps (b) and (c) are carried out with a voltage applied across the pore.

When the target polynucleotide is contacted with a Phi29 DNA polymerase and a pore derived from Msp, the target polynucleotide firstly forms a complex with the Phi29 DNA polymerase. When the voltage is applied across the pore, the target polynucleotide/Phi29 DNA polymerase complex forms a complex with the pore and controls the movement of the single stranded polynucleotide through the pore.

This embodiment has three unexpected advantages. First, the target polynucleotide moves through the pore at a rate that is commercially viable yet allows effective sequencing. The target polynucleotide moves through the Msp pore more quickly than it does through a hemolysin pore. Second, an increased current range is observed as the polynucleotide moves through the pore allowing the sequence to be estimated or determined more easily. Third, a decreased current variance is observed when the specific pore and polymerase are used together thereby increasing the signal-to-noise ratio.

Any polynucleotide described above may be sequenced.

The pore may be any of the pores discussed above. The pore may comprise eight monomers comprising the sequence shown in SEQ ID NO: 2 or a variant thereof.

As discussed above, wild-type Phi29 DNA polymerase has polymerase and exonuclease activity. It may also unzip double stranded polynucleotides under the correct conditions. Hence, the enzyme may work in three modes (as discussed above). The method of the invention preferably involves an Msp pore and Phi29 DNA polymerase. The Phi29 DNA polymerase preferably separates the double stranded target polynucleotide and controls the movement of the resulting single stranded polynucleotide through the pore.

Any of the systems, apparatus or conditions discussed above may be used in accordance with this preferred embodiment. The salt concentration is typically from 0.15 M to 0.6 M. The salt is preferably KCl.

Kits

The present invention also provides kits for preparing a double stranded target polynucleotide for sequencing. The kit comprises (a) a bridging moiety capable of linking the two strands of the target polynucleotide and (b) at least one polymer.

In a preferred embodiment, the kit further comprises a leader polymer and a tail polymer. Leader polymers and tail polymers are described in detail above. If the leader and tail polymers are polynucleotides, the leader and tail polymers can be provided as a single unit. In this unit, a portion of the leader polymer and a portion of the tail polymer form a double strand. This double stranded region may typically be from 5 to 20 nucleotide pairs in length. The end of the double stranded portion of this unit is linked to the double stranded target polynucleotide. Suitable methods for linking two double stranded polynucleotides are known in the art. The remainder of the leader and tail polymer remain as single stranded polynucleotides.

The kit also preferably further comprises one or more markers that produce a distinctive current when they interact with a transmembrane pore. Such markers are described in detail above.

The kit preferably also comprises means to couple the target polynucleotide to a membrane. Means of coupling the target polynucleotide to a membrane are described above. The means of coupling preferably comprises a reactive group. Suitable groups include, but are not limited to, thiol, cholesterol, lipid and biotin groups.

The kit may further comprise the components of a membrane, such as the phospholipids needed to form a lipid bilayer.

Any of the embodiments discussed above with reference to the methods of the invention are equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Method of Preparing a Target Polynucleotide for Sequencing

The invention also provides a method of preparing a double stranded target polynucleotide for sequencing. This method generates the construct that allows the target polynucleotide to be sequenced. In this method, the two strands of the target polynucleotide are linked by a bridging moiety and a polymer is attached to one strand at the other end of the target polynucleotide. The polymer is preferably a leader polymer and the method also preferably further comprises attaching a tail polymer to the other strand of the target polynucleotide (i.e. at the same end as the leader polymer). Leader polymers and tail polymers are discussed in detail above.

The method preferably also further comprises attaching a means to couple the construct to the membrane to the construct. Such means are described above.

The bridging moiety may be synthesized separately and then chemically attached or enzymatically ligated to the target polynucleotide. Means for doing so are known in the art. Alternatively, the bridging moiety may be generated in the processing of the target polynucleotide. Again, suitable means are known in the art.

A suitable means for preparing a target polynucleotide for sequencing is illustrated in Example 3.

Apparatus

The invention also provides an apparatus for sequencing a double stranded target polynucleotide. The apparatus comprises (a) a membrane. (b) a plurality of transmembrane pores in the membrane, (c) a plurality of polynucleotide binding proteins capable of separating the two strands of the target polynucleotide and (d) instructions for carrying out the method of the invention. The apparatus may be any conventional apparatus for polynucleotide analysis, such as an array or a chip. Any of the embodiments discussed above with reference to the methods of the invention are equally applicable to the kits of the invention.

The apparatus is preferably set up to carry out the method of the invention.

Suitable nucleic acid binding proteins, such as Phi29 DNA polymerase, are described above.

The apparatus preferably comprises:
  a sensor device that is capable of supporting the membrane and plurality of pores and being operable to perform polynucleotide sequencing using the pores and proteins;
  at least one reservoir for holding material for performing the sequencing;
  a fluidics system configured to controllably supply material from the at least one reservoir to the sensor device; and
  a plurality of containers for receiving respective samples, the fluidics system being configured to supply the samples selectively from the containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

The following Examples illustrate the invention:

Example 1—Reading Around dsDNA Hairpins

Figure 3:
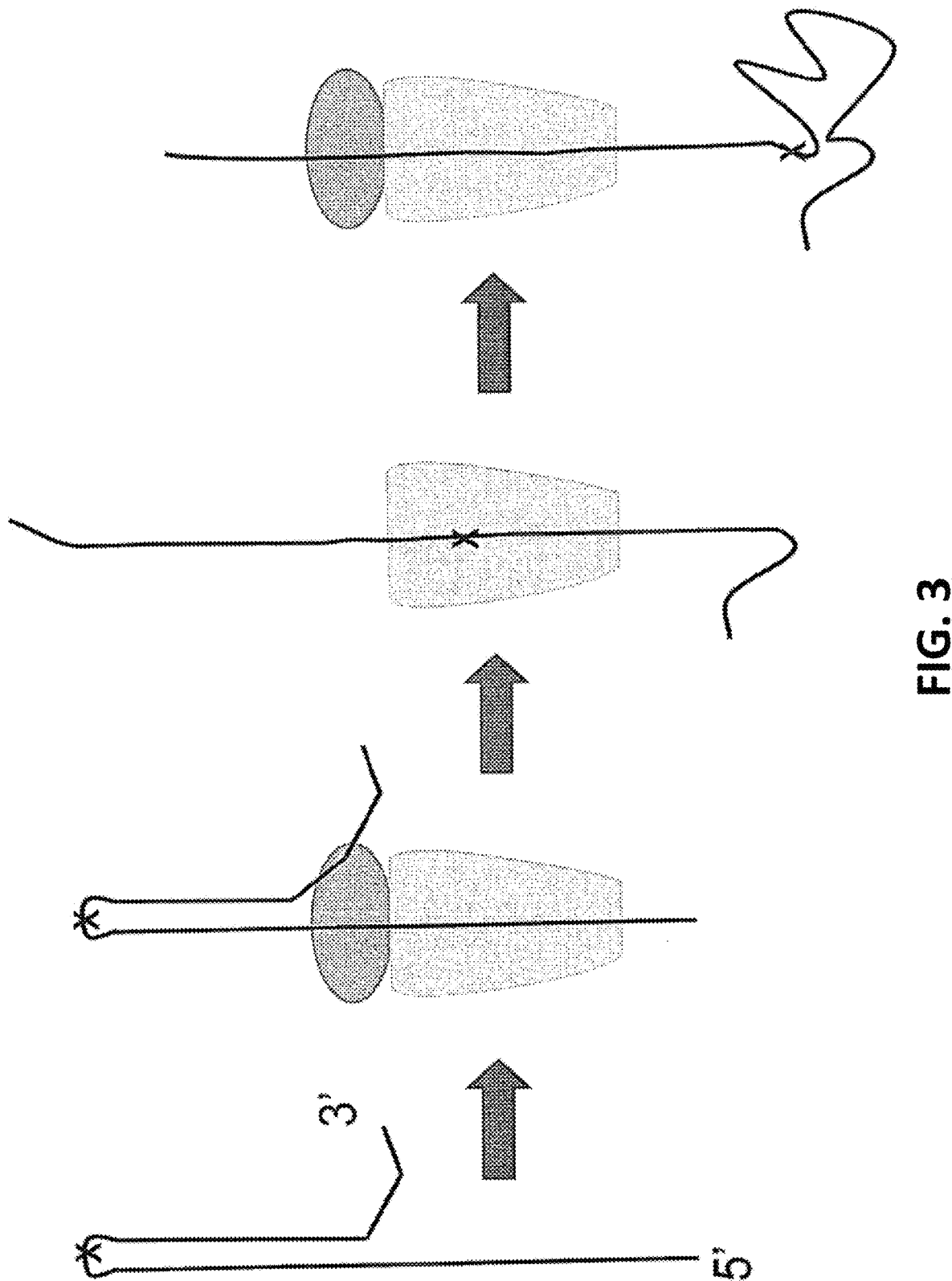
FIG. 3 shows a schematic overview of reading around a hairpin of dsDNA using the ability of the enzyme to control movement in ssDNA regions. The dsDNA has a 5'-ssDNA leader to allow capture by the nanopore. This is followed by a dsDNA section, where the sense and anti-sense strands are connected by a hairpin. The hairpin can optionally contain markers (e.g. abasic residues, shown in FIG. 3 as a cross) that are observed during sequencing, which permit simple identification of the sense and anti-sense strands during sequencing. The 3'-end of the anti-sense strand can optionally also have a 3'-ssDNA overhang, which if greater than ~20 bases allows full reading of the anti-sense strand (the read-head of the nanopore is ~20 bases downstrand from the top of the DNA in the enzyme).

The ability of an enzyme such as Phi29 DNA polymerase to act as a molecular brake along ssDNA, but still also functionally pass along dsDNA sections, can be exploited to read around the hairpin turn of dsDNA constructs, permitting DNA/RNA sequencing of both the sense and anti-sense strands. FIG. 3 illustrates how both the sense and anti-sense strands of dsDNA constructs with hairpin turns can be sequenced with an enzyme such as Phi29 DNA polymerase. In this implementation based on Phi29 DNA polymerase, the dsDNA constructs contain a 5'-ssDNA leader to enable capture under an applied field by a nanopore. This is followed by a dsDNA section that is linked by a hairpin turn. The hairpin turn can optionally contain a marker (X in FIG. 3) in the turn that creates a characteristic current signature to aid in identification of the sense strand region from the anti-sense region. Since the last ~20 bases in the current implementation are not sequenced because the read-head is ~20 bases downstrand of the enzyme when it falls off the end of the DNA, the constructs could also optionally contain a 3'-ssDNA extension to permit reading to the end of the anti-sense region.

The hairpin turns that link the two dsDNA sections could be made of, but are not limited to, sections of DNA/RNA, modified DNA or RNA, PNA, LNA, PEG, other polymer linkers, or short chemical linkers. The hairpin linkers could be synthesised separately and chemically attached or enzymatically ligated to dsDNA, or could be generated in processing of the genomic DNA.

Methods:

DNA: Four separate DNA constructs were prepared as shown in FIGS. 4-7 from synthetic DNA (Table 4).

TABLE 4

Synthetic DNA used in experiments of Example 1

| ONT Name | DNA sequence |
|---|---|
| UZ07 | 5'-CCCCCCCCCCCCCCCACCCCCCCCCCCCCCCCCCTA TTCTGTTTATGTTTCTTGTTTGTTAGCCTTTTGGCTAACA AACAAGAAACATAAACAGAATAG-3' (SEQ ID NO: 16) |
| UZ08 | 5'-CCCCCCCCCCCCCCCACCCCCCCCCCCCCCCCCCTA TTCTGTTTATGTTTCTTGTTTGTTAGCC-3' (SEQ ID NO: 17) |
| UZ12 | 5'-GGCTAACAAACAAGAAACATAAACAGAATAG-3' (SEQ ID NO: 18) |
| UA02 | 5'-CCCCCCCCCCCCCCCACCCCCCCCCCCCCCCCCCTA TTCTGTTTATGTTTCTTGTTTGTTAGCCTTTTGGCTAACA AACAAGAAACATAAACAGAATAGCCCCCCCCCCTCAGATC TCACTATC-3' (SEQ ID NO: 19) |

TABLE 4-continued

Synthetic DNA used in experiments of Example 1

| ONT Name | DNA sequence |
|---|---|
| MS23 | 5'-CCCCCCCCCCCCCCCACCCCCCCCCCCCCCCCCCTA<br>TTCTGTTTATGTTTCTTGTTTGTTAGCCTTXTTGGCTAAC<br>AAACAAGAAACATAAACAGAATAG-3'<br>(SEQ ID NO: 20) |

All DNA were purchased from Integrated DNA Technologies (IDT) as a PAGE purified dry pellet, and were resolvated in pure water to a final concentration of 100 M. The short dsDNA construct was prepared by hybridizing UZ08 to UZ12 (Table 4). To hybridize, equal quantities of the 100 pM DNA solutions were mixed together, heated to 95° C. on a hot plate, held at 95° C. for 10 min, then allowed to slowly cool to room temperature over the course of ~2 hours. This yields a final solution of hybridized DNA complex at 50 uM. The UZ07, UA02 and MS23 DNA constructs are hairpins with 4T turns (Table 4). To hybridize the sense and anti-sense regions, the 100 pM DNA solutions were heated to 95° C. on a hot plate, held at 95° C. for 10 min, then rapidly cooled to 4° C. by placing the samples in a refrigerator. The rapid cooling enhances intra-molecular hairpin formation over inter-molecular hybridization. The process yields a final solution of hybridized DNA hairpins at 100 μM.

MspA production: Purified MspA (NNNRRK) oligomers were made in a cell-free *Escherichia coli* in vitro transcription translation system (Promega). Purified oligomers were obtained by cutting the appropriate oligomer band from a gel after SDS-PAGE, then re-solvating in TE buffer.

Unzipping experiments: Electrical measurements were acquired from single MspA nanopores inserted in 1,2-diphytanoyl-glycero-3-phosphocholine lipid (Avanti Polar Lipids) bilayers. Bilayers were formed across ~100 μm diameter apertures in 20 μm thick PTFE films (in custom Delrin chambers) via the Montal-Mueller technique, separating two 1 mL buffered solutions. All experiments were carried out in a Strand EP buffer of 400 mM KCl, 10 mm Hepes, 1 mM EDTA, 1 mM DTT at pH 8.0. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage.

DNA construct and Phi29 DNA polymerase (Enzymatics, 150 μM) were added to 100 μL of strand EP buffer and pre-incubated for 5 mins (DNA=1 μM, Enzyme=2 μM). This pre-incubation mix was added to 900 μL of buffer in the cis compartment of the electrophysiology chamber to initiate capture and unzipping of the complexes in the MspA nanopore (to give final concentrations of DNA=0.1 μM, Enzyme=0.2 μM). Only one type of DNA was added into the system in a single experiment. Unzipping experiments were carried out at a constant potential of +180 mV.

Results:

Characteristic and consistent polymerase controlled DNA movements were observed when the dsDNA constructs with and without hairpins were unzipped through MspA nanopores using Phi29 DNA polymerase (FIGS. 4-7). FIGS. 4-7 show the consensus DNA sequence profiles obtained from multiple single translocations of an analyte through the nanopore) for each of the DNA constructs shown.

The d&DNA construct (UZ08+UZ12) with no hairpin shows a small number of sequence dependent states (typically ~10, FIG. 4). This is consistent with ~10-15 bases of the 31 in the dsDNA section passing through the read-head of the nanopore before the enzyme falls off the 3'-end of the DNA (~20 bases upstrand of the read-head), and the last ~20 bases translocate un-braked through the nanopore, too fast to be resolved.

UZ07 (Table 4) contains the same DNA sequence as UZ08-UZ12, but is a hairpin construct with a 4T turn connecting the sense and anti-sense strands. The consensus sequence obtained from UZ07 (FIG. 5) shares the same initial profile as UZ08+UZ12, but shows many more sequence states (typically >30) than that for UZ08+UZ12 dsDNA (FIG. 4). This shows that the enzyme is proceeding around the hairpin of the sense strand, and along the anti-sense strand. This allows downstrand reading of the entire sense strand, and part of the anti-sense strand (except the last ~20 bases before the enzyme falls of the 3'-end).

Figure 8:
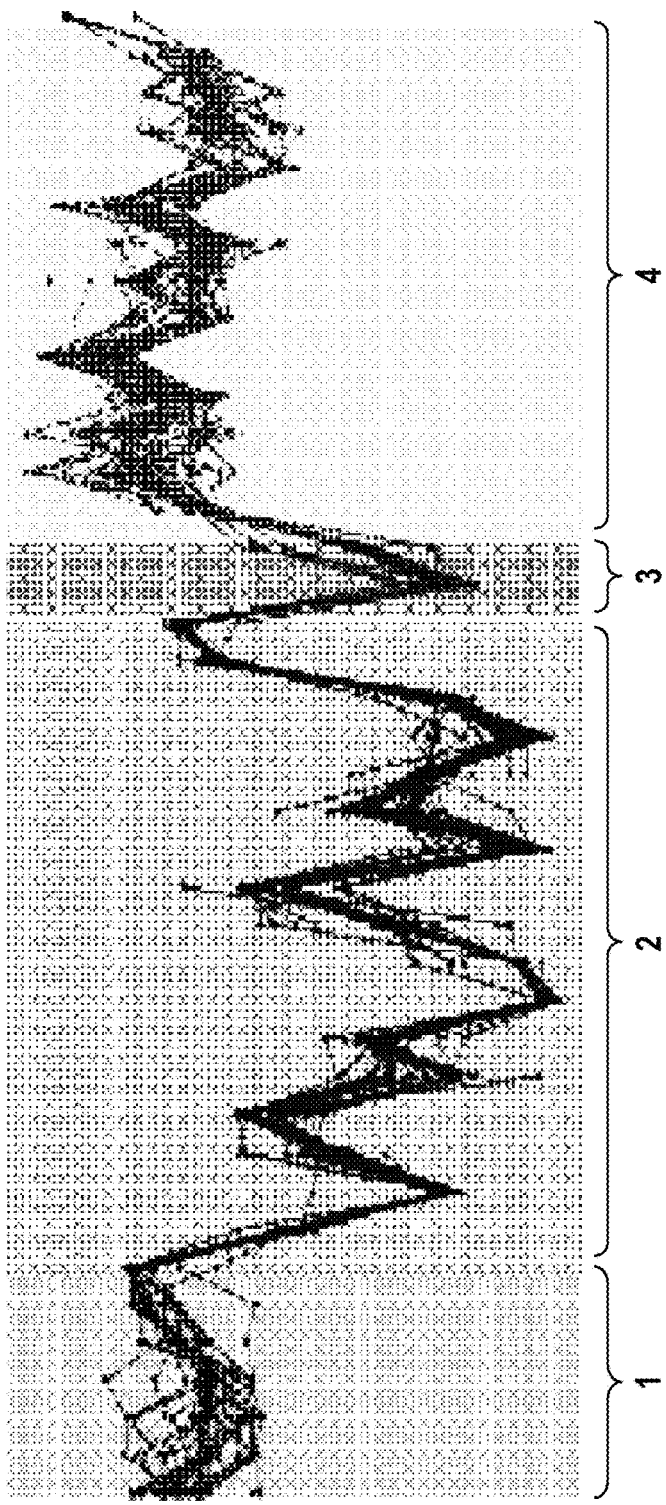
FIG. 8 shows the consensus DNA sequence of UA02 through MspA. Section 1 marks the homopolymeric 5'-overhang initially in the nanopore. Section 2 marks the sense section of the DNA strand. Section 3 marks the turn. Section 4 marks the anti-sense region of the DNA strand. The polynucleotide sequence that corresponds to each section is shown below that section number.

UA02 (Table 4) has the same sequence as UZ07, but with the addition of an extra 25 bases of non-complementary ssDNA on the 3'-end of the construct. The consensus sequence obtained from UA02 (FIG. 6) shows a closely matching sequence profile to UZ07 (FIG. 5), but with an additional ~20 states at the end. The additional 25 bases on the 3'-end permits the full length of anti-sense to be read before the up-strand enzyme falls off the end of the DNA (~20 bases upstrand of the read-head). FIG. 8 shows the consensus sequence from UA02—the homopolymeric 5'-overhang initially in the nanopore (section 1), the sense (section 2), turn (section 3) and antisense (section 4) regions.

Markers can be placed in or near the hairpin turn, that when sequenced can produce a characteristic signal that permits simple identification of the sense and anti-sense regions of unknown DNA sequences. MS23 (Table 4) has the same sequence as UZ07, but with the addition of an abasic marker in the 4T turn of the hairpin separating the sense and anti-sense strands. The consensus sequence obtained from MS23 (FIG. 7) shows a closely matching sequence profile to UZ07 (FIG. 5), but with an altered large upwards spike in current in the turn region (marked with *) as a result of the abasic passing through the nanopore read-head at this point. This large upwards spike in current is characteristic of the reduced ionic blocking of abasic residues in the nanopore constriction relative to normal bases, and provides a clear signal by which to separate the sense and anti sense regions.

Summary:

These experiments demonstrate that Phi29 DNA polymerase is able to read around the hairpin turn of dsDNA constructs, due to its ability to act as an efficient molecular brake along the ssDNA section.

The read-head of MspA nanopores in this implementation is ~20 bases downstrand from the DNA at the entrance to the Phi29 enzyme. As a result, when the enzyme gets to the end of a DNA strand and releases the substrate, the remaining ~20 bases translocate in an uncontrolled manner through the nanopore too quickly to be resolved/sequenced. However, optional 3'-extensions (in this 5' to 3' reading direction) can be added to the DNA constructs to extend the reading distance, which permits full sequencing of the entire antisense strand.

Markers that produce characteristics current signatures can optionally be placed in or near the hairpin turn of a DNA construct to aid in identification of the sense and anti-sense regions of the sequence. The markers could be, but are not limited to, unique known sequence motifs of normal bases, or unnatural or modified bases that produce alternative current signatures.

Example 2—Reading Around dsDNA Hairpins on Genomic DNA

Figure 9:
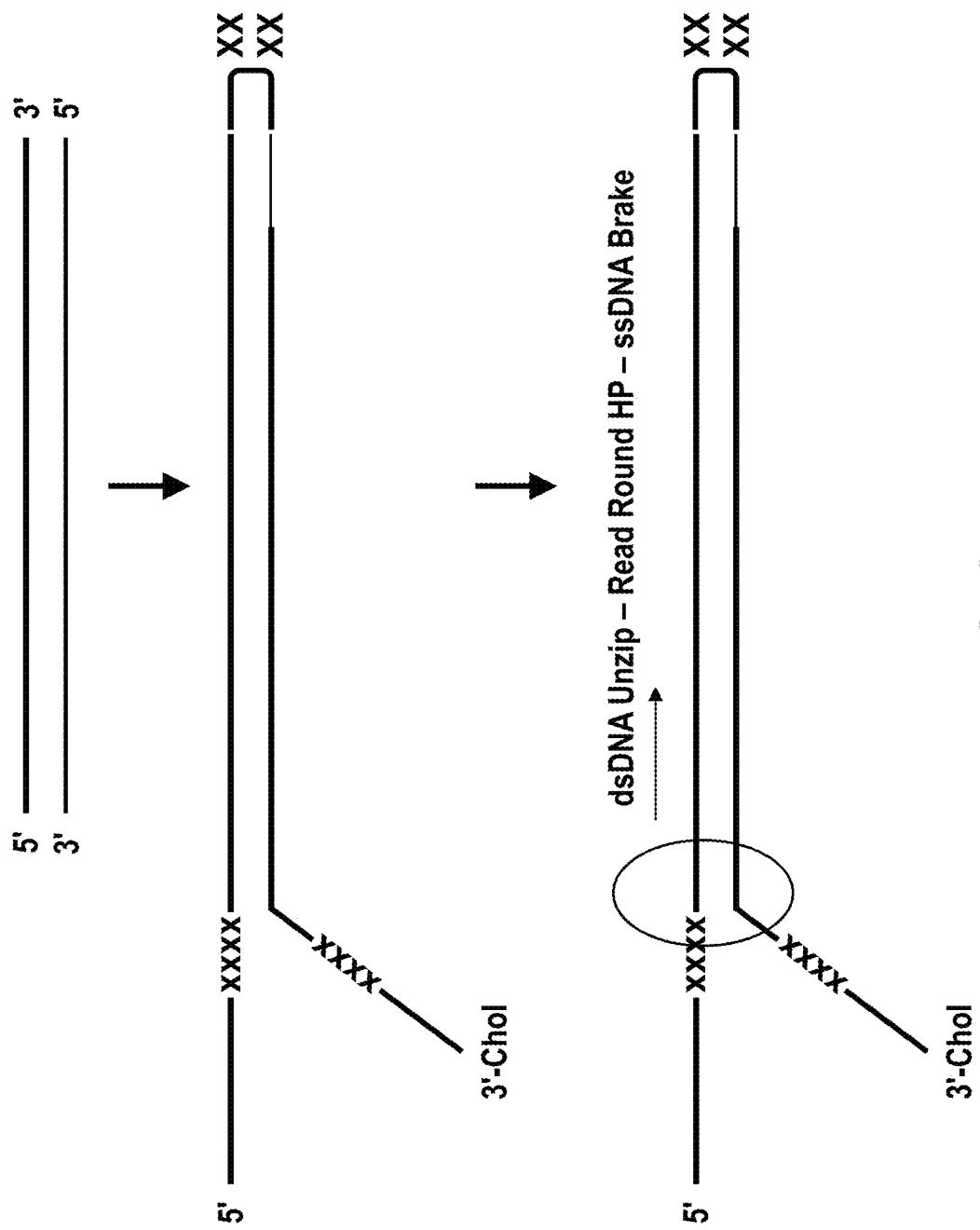
FIG. 9 shows a schematic of a genomic template for unzipping through MspA nanopores using Phi29 DNA polymerase. It shows a general design outline for creating dsDNA suitable for reading around hairpins. The constructs have a leader sequence with optional marker (e.g. abasic DNA) for capture in the nanopore, and hairpin with optional marker, and a tail for extended reading into anti-sense strand with optional marker.

Reading around hairpins using Phi29 DNA polymerase can be extended to long genomic dsDNA with ligated hairpins (FIG. 9). FIG. 9 shows a general design outline for creating dsDNA suitable for reading around hairpins. The constructs have a leader sequence with optional marker (e.g. abasic DNA) for capture in the nanopore, and hairpin with optional marker, and a tail for extended reading into anti-sense strand with optional marker.

Figure 10:
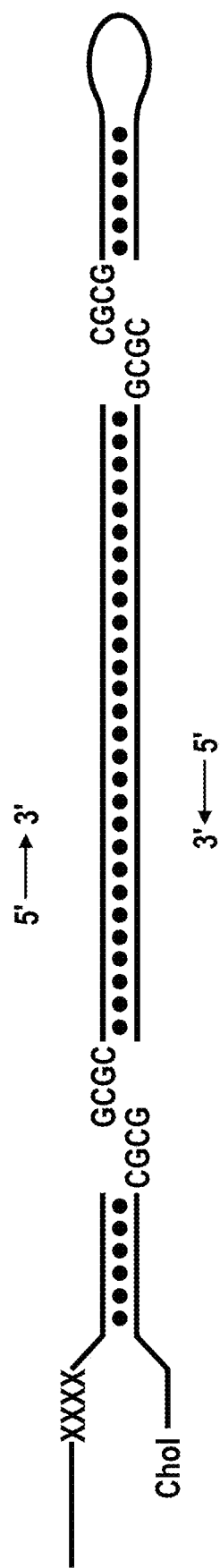
FIG. 10 shows a schematic of the adapter design for ligating ssDNA overhangs (left) and hairpin turns (right) onto genomic dsDNA. X=abasic DNA. Chol=cholesterol-TEG DNA modification.

Methods:

DNA: A 400 base-pair section of PhiX 174 RF1 genomic DNA was amplified using PCR primers containing defined restriction sites. Following KasI and MluI restriction endonuclease digestion of the 400 bp fragment, DNA adapters containing complimentary ends were then ligated (FIG. 10). The desired product was finally isolated by PAGE purification and quantified by absorbance at A260 nm.

For ease of analysis each adapter piece contained set abasic markers so that the progress of the DNA through the nanopore could be tracked. The sequences of all primers and adapters are given in Table 5

TABLE 5

Primer and adapter DNA for creating the genomic hairpin DNA constructs in Example 2.

| ONT Name | DNA sequence |
| --- | --- |
| KasI Sense Primer | 5'-TTTTTTTTTTGGCGCCCTGCCGTTTCTGATAAGTT GCTT-3' (SEQ ID NO: 21) |
| MluI Antisense Primer | 5'-AAAAAAAAAAACGCGTAAACCTGCTGTTGCTTGGA AAG-3' (SEQ ID NO: 22) |
| KasI Sense Adapter | 5'-TTTTTTTTTTTTTTTTTTTTTTTTTTTTTTT TTTTTTTTTTTTTTXXXXTTTTTTTTTGGCTAACAA ACAAGAAACATAAACAGAATAG-3' (SEQ ID NO: 23) |
| KasI Antisense Adapter | 5'-GCGCCTATTCTGTTTATGTTTCTTGTTTGTTAGCC TTTTTTXXXXTTTTTTTTTTTTTTTTTTTTTTTTTT TTT-3' (SEQ ID NO: 24) |
| MluI HP | 5'-CGCGCTATTCTGTTTATGTTTCTTGTTTGTTAGCC XXXXGGCTAACAAACAAGAAACATAAACAGAATAG-3' (SEQ ID NO: 25) |

Abasic DNA bases (abasic = X) in the adapters provide markers for easily identifying the start of the sense strand, the hairpin turn, and the end of the anti-sense strand.

MspA production: See Example 1.
Unzipping experiments: See Example 1.

The genomic DNA constructs were incubated with Phi29 DNA polymerase (Enzymatics, 150 µM) in 100 µl, of strand EP buffer and pre-incubated for 5 mins (DNA=5 nM, Enzyme=2 µM). This pre-incubation mix was added to 900 µL of buffer in the cis compartment of the electrophysiology chamber to initiate capture and unzipping of the complexes in the MspA nanopore (to give final concentrations of DNA=0.5 nM, Enzyme=0.2 µM). Only one type of DNA was added into the system in a single experiment. Unzipping experiments were carried out at a constant potential of +180 mV.

Figure 11:
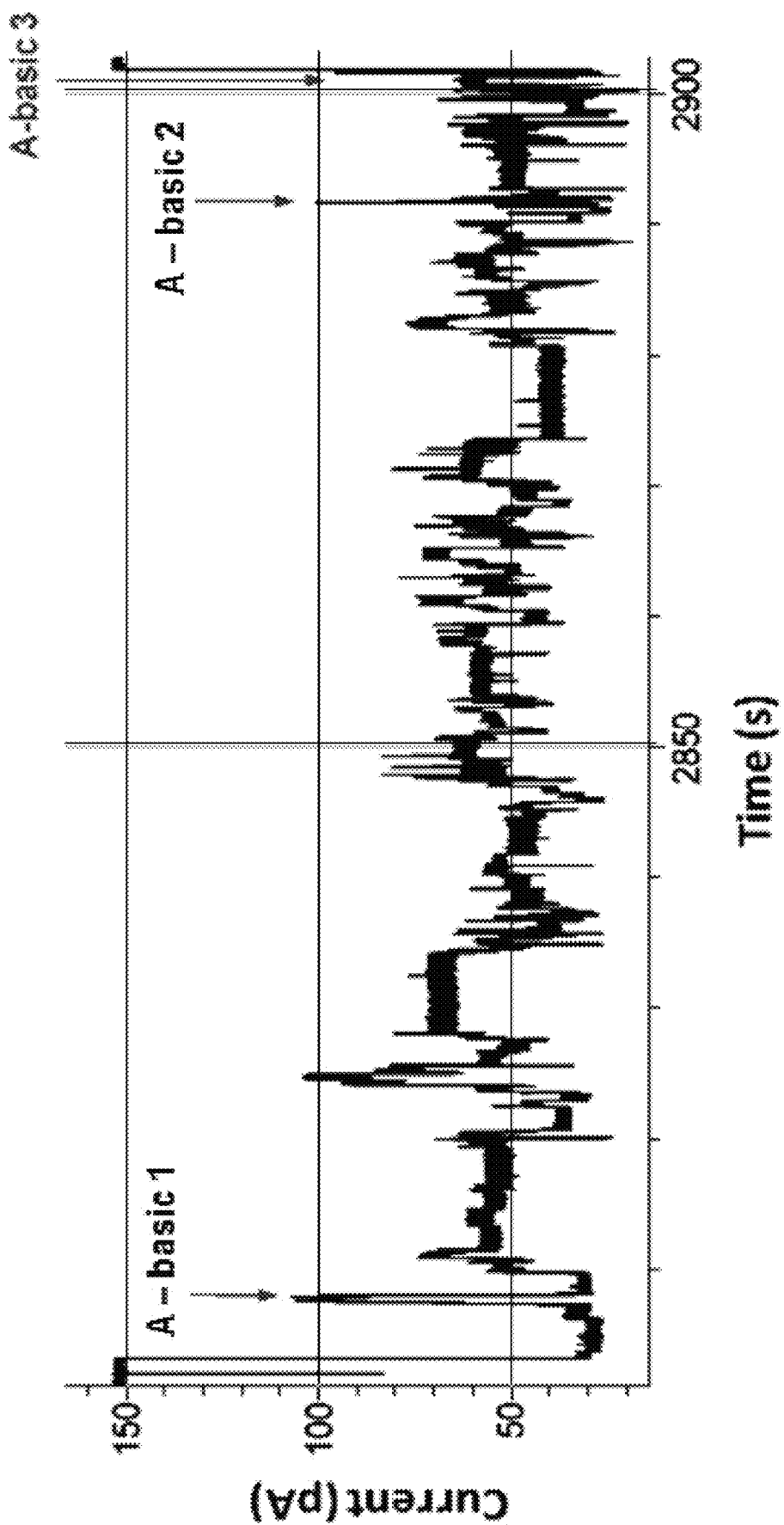
FIG. 11 shows typical polymerase controlled DNA movement of a 400mer-hairpin through MspA using Phi29 DNA polymerase. Sense region=abasic 1 to 2. Anti-sense region=abasic 2 to 3.
Figure 12:
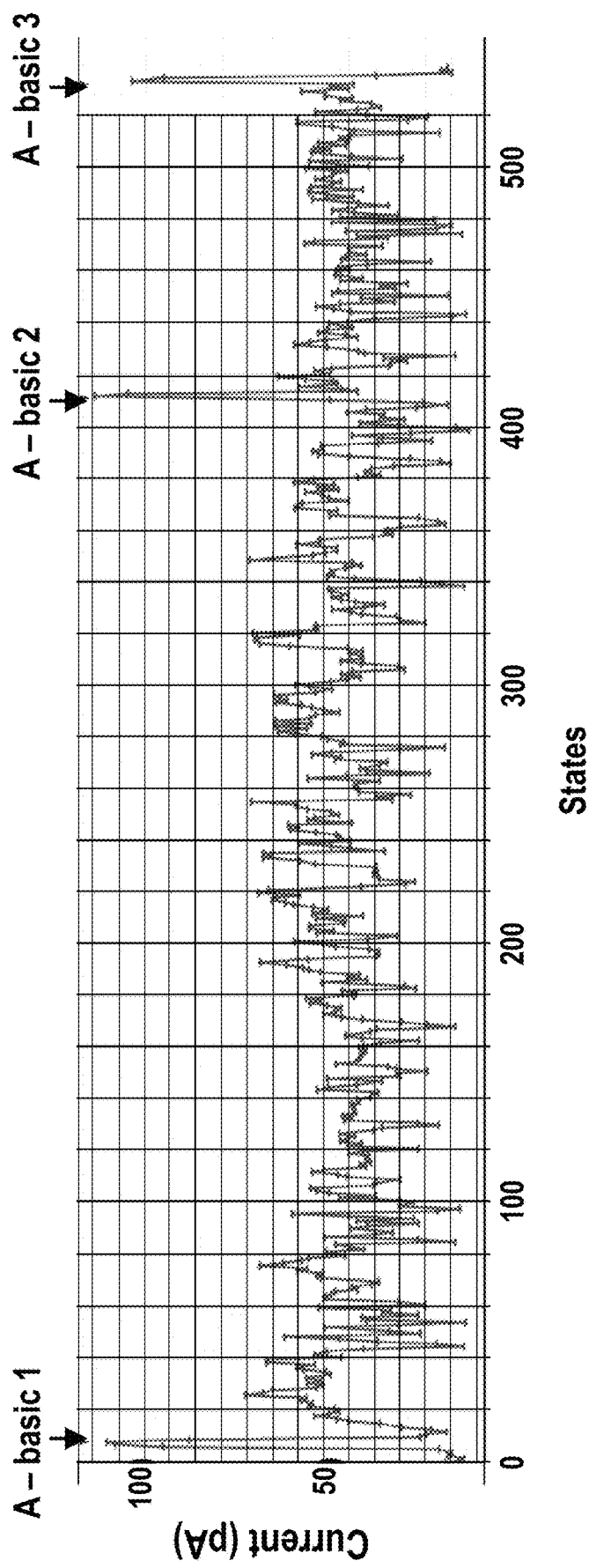
FIG. 12 shows a consensus DNA sequence profile from multiple polymerase controlled DNA movements of a 400mer-hairpin through MspA. Sense region=abasic 1 to 2. Anti-sense region=abasic 2 to 3.

Results:

400mer-No3 (which has a 3' cholesterol TEG) (Table 6) added to MspA nanopores with Phi29 DNA polymerase resulted in unzipping of the DNA and polymerase controlled DNA movement lasting 1-3 mins with a large number of sequence dependent states (FIGS. 11 and 12). The abasic markers, at the start of the sense strand, in the middle of the hairpin turn, and at the end of the anti-sense strand, permit easy identification of the separate sections of the sequence. FIGS. 11 and 12 clearly show 3 abasic peaks, demonstrating the ability to read around hairpins ligated to long genomic DNA, and thus sequence both the sense and anti-sense strands of the dsDNA.

TABLE 6

Full DNA sequence of genomic construct with ligated adapters used in this example.

| ONT Name | DNA sequence |
| --- | --- |
| 400mer No3 | 5'-TTTTTTTTTTTTTTTTTTTTTTTTTTTTT TTTTTTTTTTTTTTTTXXXXTTTTTTTTTTGGCTA ACAAACAAGAAACATAAACAGAATAGGCGCCCTGCC GTTTCTGATAAGTTGCTTGATTTGGTTGGACTTGGT GGCAAGTCTGCCGCTGATAAAGGAAAGGATACTCGT GATTATCTTGCTGCTGCATTTCCTGAGCTTAATGCT TGGGAGCGTGCTGGTGCTGATGCTTCCTCTGCTGGT ATGGTTGACGCCGGATTTGAGAATCAAAAAGAGCTT ACTAAAATGCAACTGGACAATCAGAAAGAGATTGCC GAGATGCAAAATGAGACTCAAAAAGAGATTGCTGGC ATTCAGTCGGCGACTTCACGCCAGAATACGAAAGAC CAGGTATATGCACAAAATGAGATGCTTGCTTATCAA CAGAAGGAGTCTACTGCTCGCGTTGCGTCTATTATG GAAAACACCAATCTTTCCAAGCAACAGCAGGTTTAC GCGCTATTCTGTTTATGTTTCTTGTTTGTTAGCCXX XXGGCTAACAAACAAGAAACATAAACAGAATAGCGC GTAAACCTGCTGTTGCTTGGAAAGATTGGTGTTTTC CATAATAGACGCAACGCGAGCAGTAGACTCCTTCTG TTGATAAGCAAGCATCTCATTTTGTGCATATACCTG GTCTTTCGTATTCTGGCGTGAAGTCGCCGACTGAAT GCCAGCAATCTCTTTTTGAGTCTCATTTTGCATCTC GGCAATCTCTTTCTGATTGTCCAGTTGCATTTTAGT AAGCTCTTTTGATTCTCAAATCCGGCGTCAACCAT ACCAGCAGAGGAAGCATCAGCACCAGCACGCTCCCA AGCATTAAGCTCAGGAAATGCAGCAGCAAGATAATC ACGAGTATCCTTTCCTTTATCAGCGGCAGACTTGCC ACCAAGTCCAACCAAATCAAGCAACTTATCAGAAAC GGCAGGGCGCCTATTCTGTTTATGTTTCTTGTTTGT TAGCCTTTTTTXXXXTTTTTTTTTTTTTTTTTTTT TTTTTTTTT-3' (SEQ ID NO: 26) |

Example 3—Sample Preparation for Sequencing

A 400 base-pair section of PhiX 174 RF1 genomic DNA was amplified using PCR primers containing defined restriction sites. Following KasI and MluI restriction endonuclease digestion of the 400 bp fragment. DNA adapters containing complimentary ends were then ligated. The desired product was finally isolated by PAGE purification and quantified by absorbance at A260 nm.

For case of analysis each adapter piece contained set abasic markers so that the progress of the DNA through the nanopore could be tracked. The sequences of all primers and adapters are given below (X=abasic modification):

KasI Sense Primer (SEQ ID NO. 21)
TTTTTTTTTTGGCGCCCTGCCGTTTCTGATAAGTTGCTT

-continued

MluI Antisense Primer
(SEQ ID NO. 22)
AAAAAAAAAAACGCGTAAACCTGCTGTTGCTTGGAAAG

KasI Sense Adapter
(SEQ ID NO. 23)
TTTTTTTTTTTTTTTTTTTTTTTTTTTTTTTTTTTTTTTT

XXXXTTTTTTTTTGGCTAACAAACAAGAAACATAAACAGAATAG

KasI Antisense Adapter
(SEQ ID NO. 24)
GCGCCTATTCTGTTTATGTTTCTTGTTTGTTAGCCTTTTTTXXXXTTTTT

TTTTTTTTTTTTTTTTTTTTTTTT

MluI HP
(SEQ ID NO. 25)
CGCGCTATTCTGTTTATGTTTCTTGTTTGTTAGCCXXXXGGCTAACAAAC

AAGAAACATAAACAGAATAG

The construct is shown in FIG. 10.

If the above adapters contain non-complimentary bases instead of abasic sites then it is possible to open out the analyte using a primer complimentary to the ssDNA section of the antisense Y-shaped adapter and a strand displacing polymerase (such as Phi29 or Klenow). If the primer and Y-shaped adapter complimentary region also contain a restriction site then another hairpin can be ligated, after the amplification, and the process repeated to expand the template further. This gives the ability to sequence the molecule twice; the original sense-antisense in a fully dsDNA unzipping mode and then the amplified sense-antisense strand in fully ssDNA unzipping mode.

Ligation of DNA adapters to target DNA has been well described previously and this is still the most widespread technique. Ligation of the adapters could occur either by single strand ligation using T4 RNA ligase 1 or by double strand ligation of annealed adapters using T4 DNA ligase. To prevent target dimer and adapter dimer formation the target can be first dA-tailed using a polymerase such as Klenow exo-.

More recently, advances with artificial transposons (such as the Nextera system) have begun to show promise in rapidly speeding up adapter attachment while also simultaneously fragmenting the DNA. In theory a similar approach might be achieved using homologous recombination, such as the Cre LoxP system (NEB), providing compatible sequences lie within the DNA. Advances in chemical ligation have also improved recently, demonstrated with highest success by the successful amplification of DNA strands containing an unnatural triazole linkage (Sagheer and Brown, 2009). For chemical ligation the modification of either the 5' or 3' of the DNA is usually first required to include a suitable reactive group. Groups can be easily added to the 3' using a modified dNTP and terminal transferase. Modification of the 5' end of DNA has also been demonstrated but this has so far been limited to thiol groups using using T4 Polynucleotide kinase. Some success for direct coupling of molecules to the 5' of DNA via chemical means has been demonstrated using carboiimide coupling and such kits are commercially available. However side products are a frequent problem with this chemistry.

Example 4—Reading Around dsDNA Hairpins of Genomic DNA Using a Helicase

Figure 17:
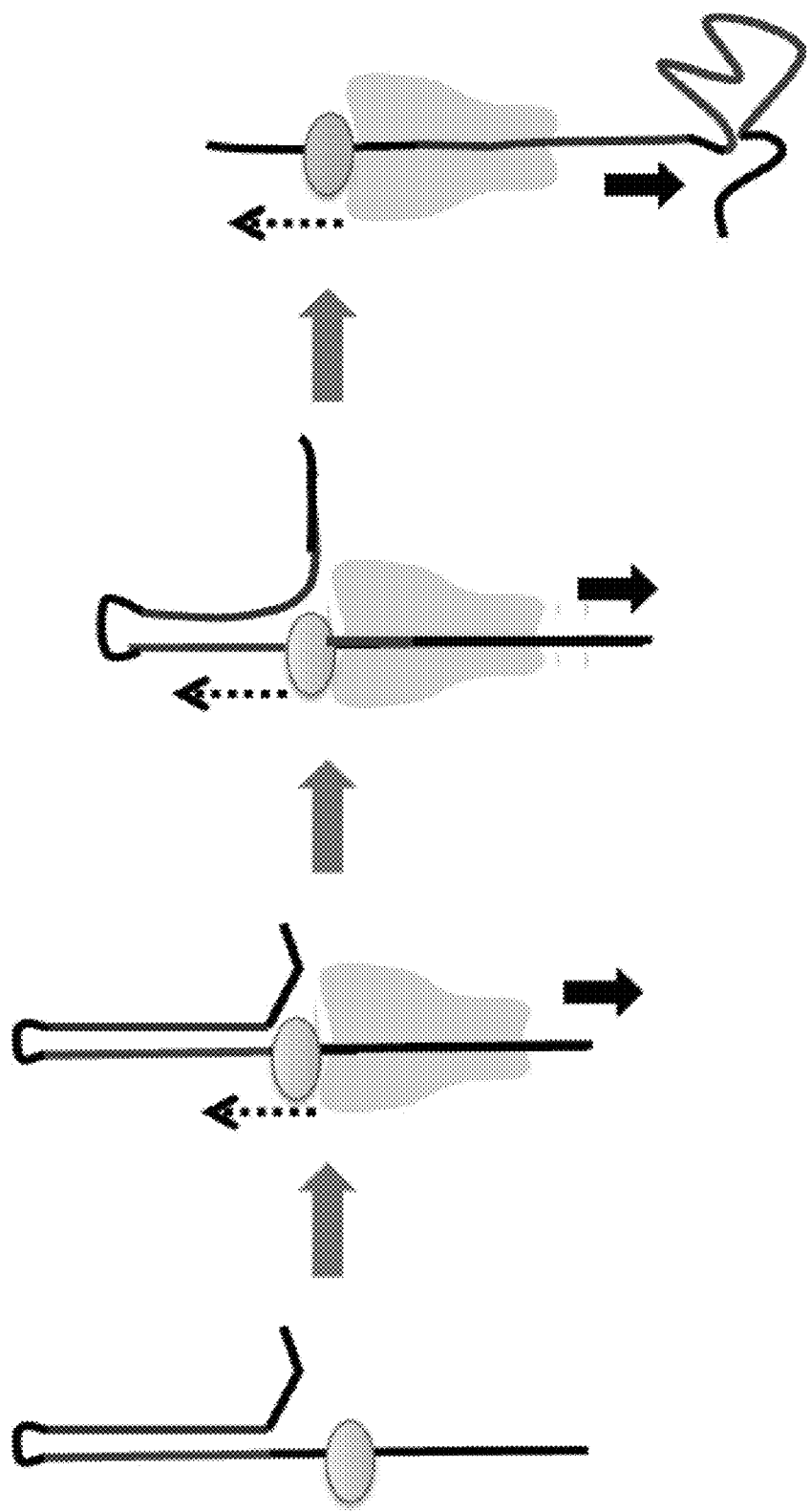
FIG. 17 shows a schematic of helicase controlled dsDNA and ssDNA translocation through a nanopore. The dsDNA has a hairpin turn linking the sense and anti-sense strands of the dsDNA. Once the enzyme reaches the hairpin it remains bound to the DNA, proceeds around the hairpin turn, and along the anti-sense strand. In the hairpin and antisense regions the enzyme functions as an ssDNA molecular brake, continuing to sufficiently control translocation of the DNA through the nanopore to sequence the DNA.

Reading around DNA strands, which consist of connected long genomic dsDNA ligated by hairpins, using a helicase enzyme was investigated (FIG. 17). The constructs used have a leader sequence with optional marker (e.g. abasic DNA) for capture in the nanopore, a hairpin with optional marker, and a tail which has an extended reading sequence and a cholesterol tether attached to the end.

Methods:

To link the sense and antisense strands a bridging hairpin (SEQ ID NO: 32) was ligated to one end. A synthetic Y-adaptor was ligated on to allow enzyme binding and threading into the nanopore: the sense strand (SEQ 1) NO: 29 attached to SEQ ID NO: 30 via four abasic DNA bases, see FIG. 18) of this adaptor contains the 5' leader, a sequence that is complementary to the tether sequence (SEQ ID NO: 35, which at the 3' end of the sequence has six iSp18 spacers attached to two thymine residues and a 3' cholesterol TEG) and 4 abasics. The antisense half of the adaptor also has a 3' hairpin which will act as an intramolecular primer for later conversion to a DUO analyte (SEQ ID NO: 31, see FIG. 22 starter template). MONO analyte DNA was prepared using a ~400 bp region of PhiX 174 (Sense strand sequence=SEQ ID NO: 33 and antisense strand sequence=SEQ ID NO: 34). The region of interest was PCR amplified with primers containing SacI and KpnI restriction sites (SEQ ID NO's: 27 and 28 respectively). Purified PCR product was then SacI and KpnI digested before a Y-shaped adapter (sense strand sequence (SEQ ID NO: 29 attached to SEQ ID NO: 30 via four abasic DNA bases) is ligated onto the 5' end of SEQ ID NO: 33 and the anti-sense strand (SEQ ID NO: 31) is ligated onto the 3' end of the SEQ ID NO: 34) and a hairpin (SEQ ID NO: 32, used to join SEQ ID NO's: 33 and 34) were ligated to either end, using T4 DNA ligase (See FIG. 18 for final DNA construct). The product was purified from a 5% TBE PAGE gel and eluted by crush and soak method into TE buffer.

MspA production: Purified MspA oligomers of the mutant MspA pore MS(B1-G75S-G77S-L88N-Q126R)8 MspA (SEQ ID NO: 2 with the mutations G75S/G77S/L88N/Q126R) were made in a cell-free Escherichia coli in vitro transcription translation system (Promega). Purified oligomers were obtained by cutting the appropriate oligomer band from a gel after SDS-PAGE, then re-solvating in TE buffer.

Helicase experiments—Electrical measurements were acquired from single MspA nanopores (MS(B1-G75S-G77S-L88N-Q126R)8 MspA (SEQ ID NO: 2 with the mutations G75S/G77S/L88N/Q126R)) inserted in 1,2-diphytanoyl-glycero-3-phosphocholine lipid (Avanti Polar Lipids) bilayers. Bilayers were formed across ~100 μm diameter apertures in 20 μm thick PTFE films (in custom Delrin chambers) via the Montal-Mueller technique, separating two 1 mL buffered solutions. All experiments were carried out in a butter of 400 mM NaCl, 100 mM Hepes, 10 mM potassium ferrocyanide, 10 mM potassium ferricyanide, pH8.0, at an applied potential of +140 mV. Single-channel currents were measured on Axopatch 200B amplifiers (Molecular Devices) equipped with 1440A digitizers. Platinum electrodes were connected to the buffered solutions so that the cis compartment (to which both nanopore and enzyme/DNA are added) is connected to the ground of the Axopatch headstage, and the trans compartment is connected to the active electrode of the headstage.

Figure 18:
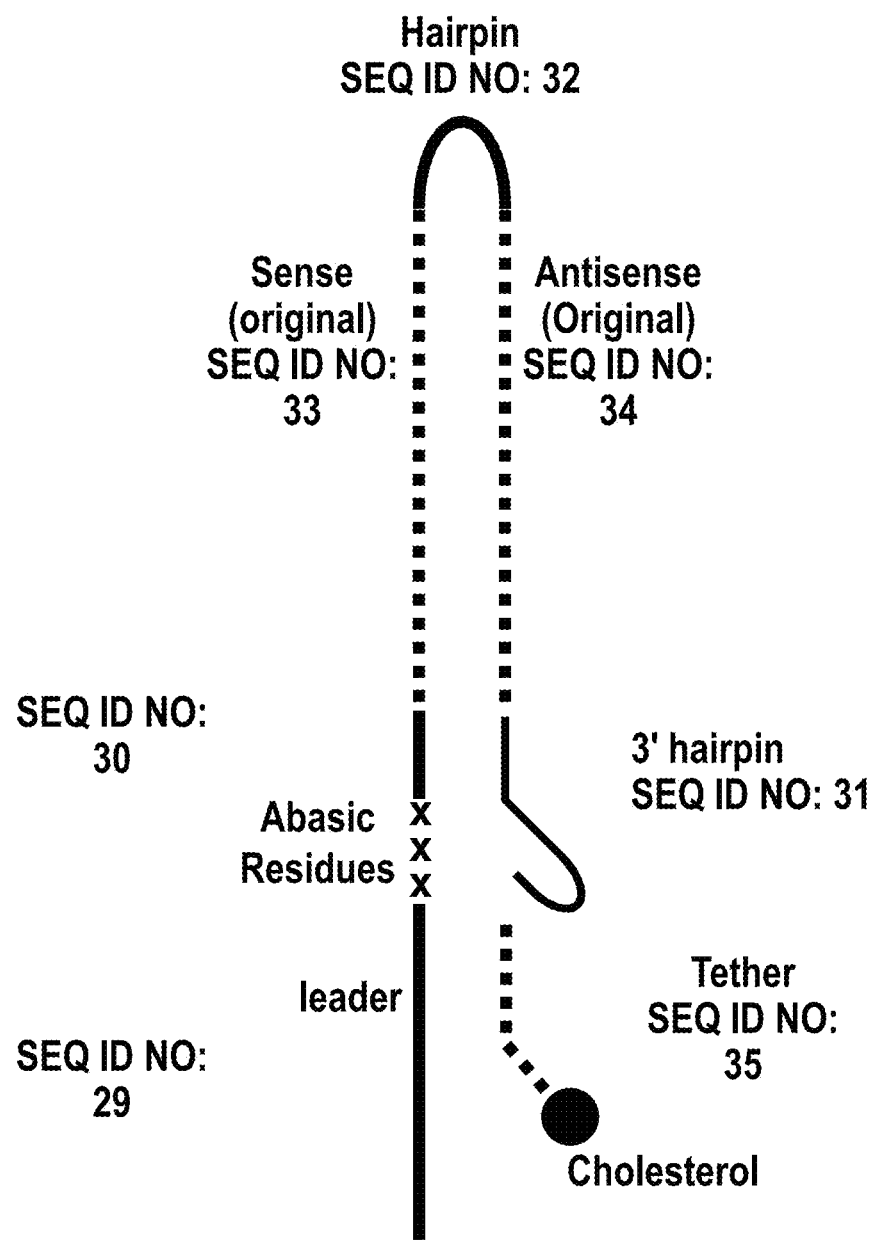
FIG. 18 shows the polynucleotide MONO hairpin construct (SEQ ID NOs: 29 to 35) used in Example 4.

A single pore was obtained before MgCl2 and dTTP were added to the cis chamber to give final concentrations of 10 mM and 5 mM respectively. Data was obtained for 5 mins at +140 mV before DNA (SEQ ID NOs: 29-35 connected as shown in FIG. 18) was added to the cis chamber for a final concentration of 0.1 nM and data obtained for a further 5 mins. Helicase was added to the cis chamber to a final concentration of 100 nM and any helicase controlled DNA movements were recorded at +140 mV.

Figure 19:
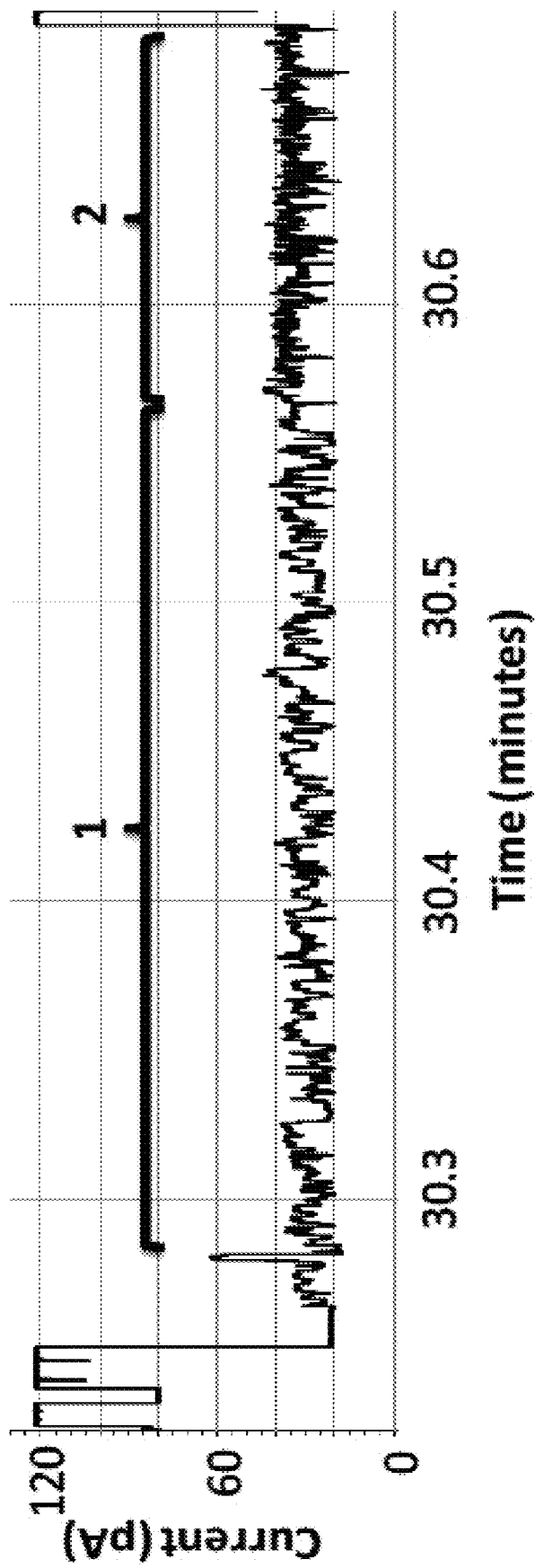
FIG. 19 shows a typical helicase controlled DNA movement of a 400 bp hairpin (SEQ ID NOs: 29 to 35 connected as shown in FIG. 18) through an MspA nanopore (MS(B1-G75S-G77S-L88N-Q126R)8 MspA (SEQ ID NO: 2 with the mutations G75S/G77S/L88N/Q126R)). Sense region 1. Anti-sense=region 2.
Figure 20:
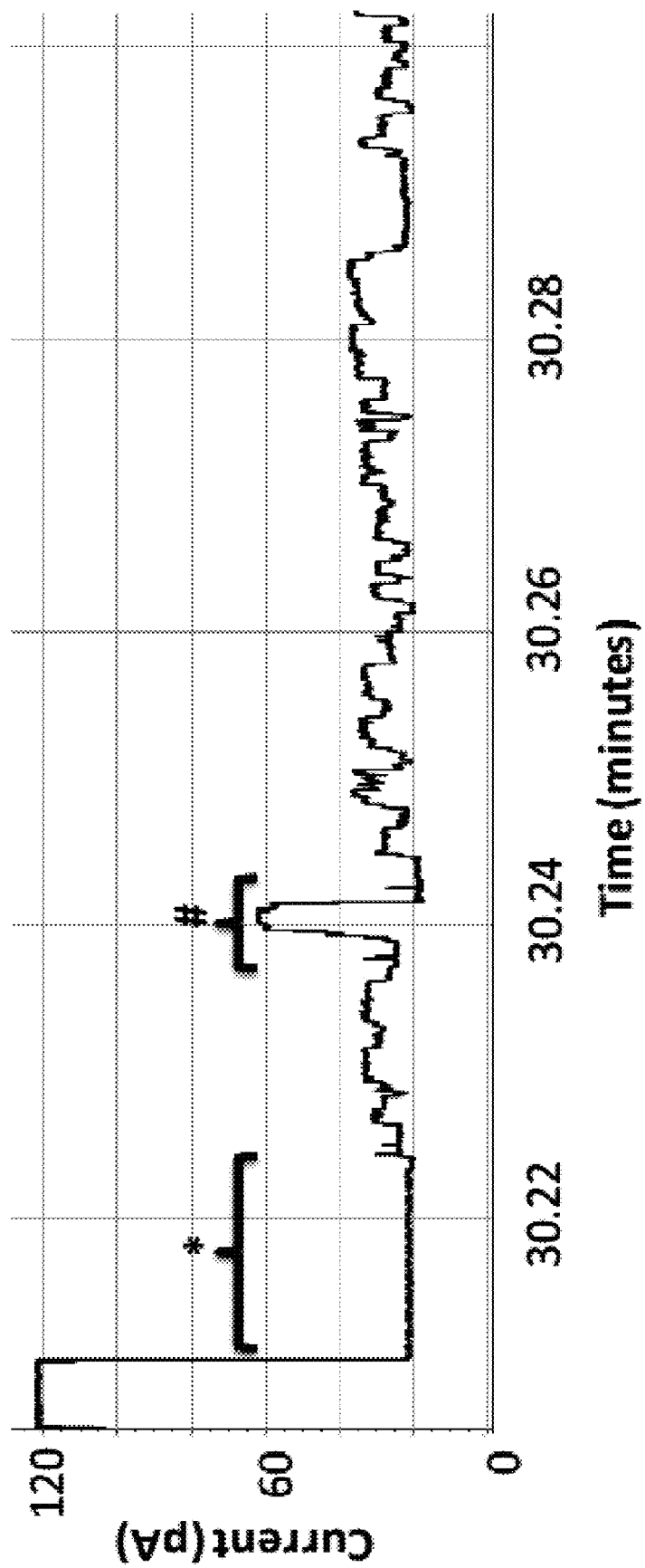
FIG. 20 shows the beginning of a typical helicase controlled DNA movement of a 400 bp hairpin (SEQ ID NOs: 29 to 35 connected as shown in FIG. 18) through an MspA nanopore (MS(B1-G75S-G77S-L88N-Q126R)8 MspA (SEQ ID NO: 2 with the mutations G75S/G77S/L88N/Q126R)). The polyT region at the beginning of the sequence is highlighted with a * and the abasic DNA bases as a #.
Figure 21:
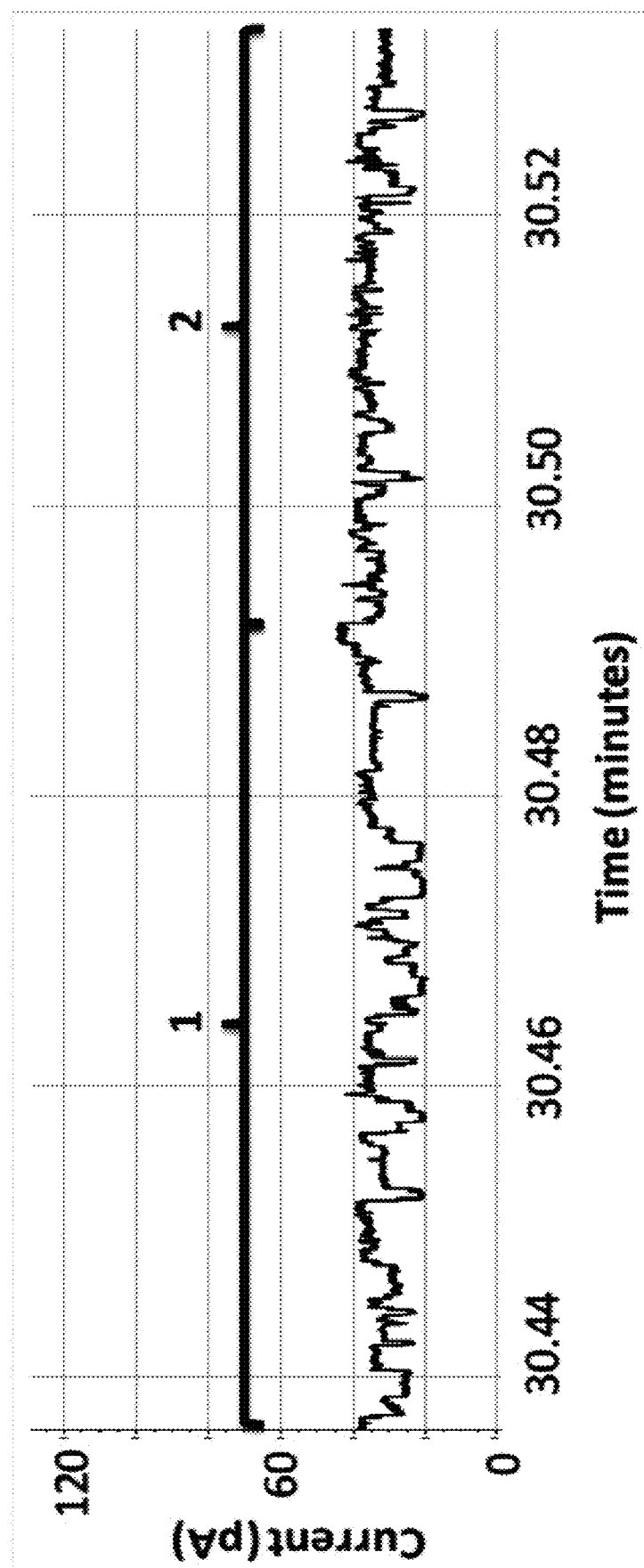
FIG. 21 shows the transition between the sense and antisense regions of a typical helicase controlled DNA movement of a 400 bp-hairpin (SEQ ID NOs: 29 to 35 connected as shown in FIG. 18) through an MspA nanopore (MS(B1-G75S-G77S-L88N-Q126R)8 MspA (SEQ ID NO: 2 with the mutations G75S/G77S/L88N1Q126R)). The transition region between the sense and antisense regions of the sequence is highlighted by a *, the sense region labeled 1 and the antisense region labeled 2.

Results:

The 400 bp sense/antisense hairpin construct (SEQ ID NO's: 29-35 connected as shown in FIG. 18) when added to an MspA nanopore (MS(B1-G75S-G77S-L88N-Q126R)8 MspA (SEQ ID NO: 2 with the mutations G75S/G77S/L88N; Q126R)) with a helicase resulted in unzipping of the DNA and helicase controlled DNA movement, with a large number of sequence dependent states (FIGS. 19 to 21). The 400 bp sense/antisense hairpin construct (SEQ ID NO's: 29-35 connected as shown in FIG. 18) produced helicase controlled DNA movement that permitted easy identification of the start of the sequence, as the polyT region and the abasic DNA bases at the start of the sense strand can be observed (highlighted with a * and a #respectively in FIG. 20). Therefore, it was possible to show that the helicase could control the movement and unzipping of a 400 bp hairpin. The clear change in speed, between the sense and antisense regions, highlights the point where the enzyme passed around the corner and is a useful marker between these regions (FIG. 21, the change from reading the sense region (1) to reading the anti-sense region (2) is shown with a *). This alteration in speed eliminates the need for markers to mark the hairpin turn. This demonstrates the ability to read around hairpins ligated to long genomic DNA with a helicase, and thus sequence both the sense and anti-sense strands of the dsDNA.

Example 5—Production of DUO Polynucleotide Hairpin Strands

It has been demonstrated already that linking the information from the sense and the antisense strands is possible by ligating a synthetic hairpin to one end of the DNA. This serves to give a read of the natural sense and antisense strands from one molecule at the same time, so making base-calling more accurate as one gets two chances to call a single position.

To link the sense and antisense strands a bridging hairpin (SEQ ID NO: 32) can be ligated to one end. It is also possible to ligate on a synthetic Y-adaptor to allow enzyme binding and threading into the nanopore: the sense strand (SEQ ID NO: 29 attached to SEQ ID NO: 30 via four abasic DNA bases, see FIG. 22 starter template) of this adaptor contains the 5' leader, a sequence that is complementary to the tether sequence (SEQ ID NO: 35, which at the 3' end of the sequence has six iSp18 spacers attached to two thymine residues and a 3' cholesterol TEG) and 4 abasics, the antisense half of the adaptor also has a 3' hairpin (SEQ ID NO: 31) which will act as an intramolecular primer for later conversion to a DUO analyte (see FIG. 22 starter template).

Figure 22:
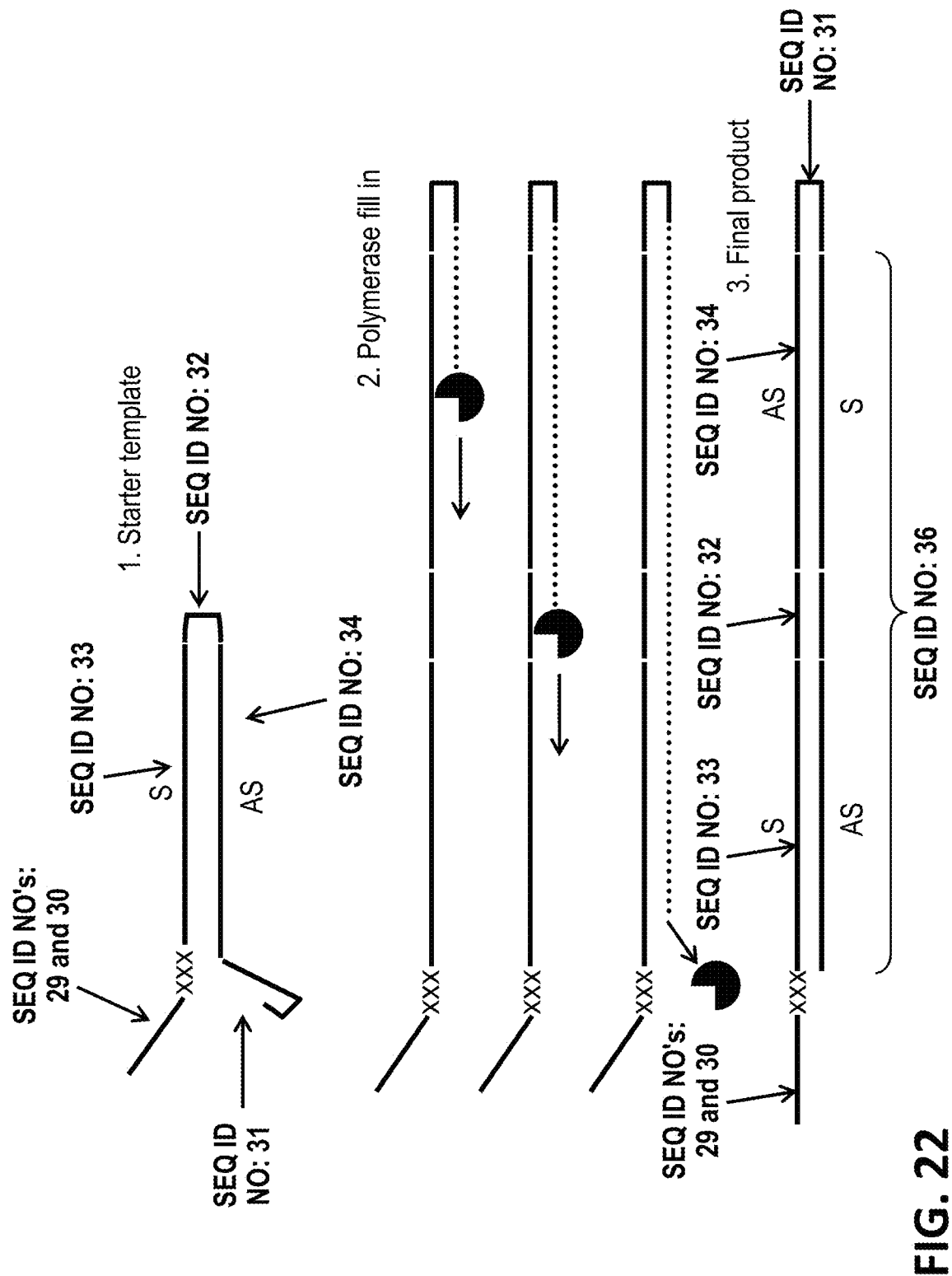
FIG. 22 shows an example sample prep method for forming DUO hairpin constructs. The double stranded DNA analyte is contacted by and modified to contain a Y-shaped adapter (the sense strand (SEQ ID NO: 29 attached to SEQ ID NO: 30 via four abasic DNA bases) of this adaptor contains the 5' leader, a sequence that is complementary to the tether (SEQ ID NO: 35, which at the 3' end of the sequence has six iSp18 spacers attached to two thymine residues and a 3' cholesterol TEG) and 4 abasics and the antisense half of the adaptor contains a 3' hairpin (SEQ ID NO: 31)) at one end of the duplex and a hairpin (SEQ ID NO: 32) at the other. The Y-shaped adapter itself also carries a 3'-hairpin (SEQ ID NO: 31), which allows extension either by a polymerase or by ligation. This extension is preferentially carried out by a mesophilic polymerase that has strand displacement activity. As the polymerase extends from the 3' of the Y-shaped adapter hairpin (SEQ ID NO: 31) it copies the antisense strand (SEQ ID NO: 34) and so displaces the original sense strand (SEQ ID NO: 33). When the polymerase reaches the end of the antisense strand (SEQ ID NO: 34) it fills-in opposite the hairpin (SEQ ID NO: 32) and then begins to fill-in opposite the now single stranded and original sense strand (SEQ ID NO: 33). Extension is then halted by a section of abasic or spacer modifications (other possible modifications which could halt enzyme extension include RNA, PNA or morpholino bases and iso-dC or iso-dG) to leave the 5'-region of the Y-shaped adapter single stranded (SEQ ID NO: 29).

When the bridging hairpin (SEQ ID NO: 32) is ligated it is also possible to ligate on a synthetic Y-adaptor: the sense strand (SEQ ID NO: 29 attached to SEQ ID NO: 30 via four abasic DNA bases, see FIG. 22 starter template) of this adaptor contains the 5' leader, a sequence that is complementary to the tether sequence (SEQ ID NO: 35, which at the 3' end of the sequence has six iSp18 spacers attached to two thymine residues and a 3' cholesterol TEG) and 4 abasics, and the antisense half of the adaptor has a 3' hairpin which will act as an intramolecular primer (SEQ ID NO: 31, see FIG. 22 starter template) this affords us the opportunity to further expand the template by copying the entire, now linked sense and antisense, using a strand displacing polymerase that binds to the 3' end of the Y-adaptor (Step 2 of FIG. 22). The Y-shaped and hairpin adaptors contain mismatched restriction sites (not sensitive to restriction digest, see top of FIG. 23). When the analyte is subsequently filled-in and expanded (see FIG. 22 steps 2 to 3), the restriction sites are completed (See bottom of FIG. 23), therefore, the fully filled-in analyte (SEQ ID NO: 29-36 connected as shown in FIG. 25) can be digested using site specific restriction endonucleases to confirm successful fill-in.

DUO analyte was prepared from the MONO analyte disclosed in Example 4 above. The doubly ligated MONO PAGE purified analyte (SEQ ID NO's: 29-35 connected as shown in FIG. 18) was further incubated with Klenow DNA polymerase, SSB and nucleotides to allow extension from the Y-shaped adapter hairpin (SEQ ID NO: 31). To screen for successful DUO product (SEQ D NOs: 29-36 connected as shown in FIG. 25) a series of mismatch restriction sites were incorporated into the adapter sequences, whereby the enzyme will cut the analyte only if the restriction site has been successfully replicated by the DUO extension process (See FIG. 23, MONO analyte at the top and DUO analyte at the bottom).

Figure 23:
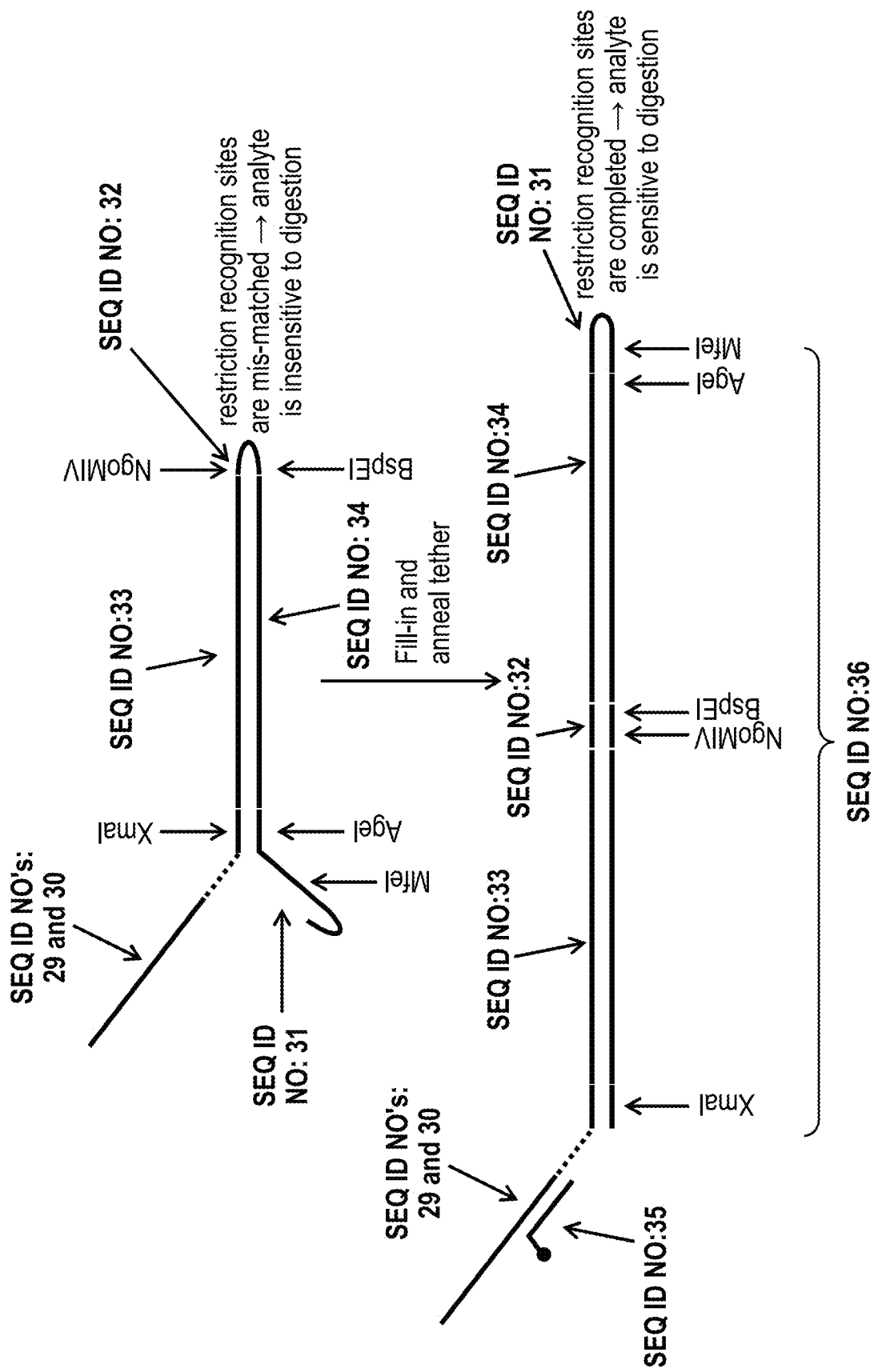
FIG. 23 shows the specific preparation method used in Example 5 for preparing a DUO hairpin construct (SEQ ID NOs: 29 to 36 connected as shown in FIG. 25). A ~400 bp region of PhiX 174 was PCR amplified with primers containing SacI and KpnI restriction sites (SEQ ID Nos: 27 and 28 respectively). Purified PCR product was then SacI and KpnI digested before a Y-shaped adapter (sense strand sequence (SEQ ID NO: 29 attached to SEQ ID NO: 30 via four abasic DNA bases) is ligated onto the 5' end of SEQ ID NO: 33 and the anti-sense strand (SEQ ID NO: 31) is ligated onto the 3' end of the SEQ ID NO: 34) and a hairpin (SEQ ID NO: 32, used to join SEQ ID NO's: 33 and 34) were ligated to either end, using T4 DNA ligase (See FIG. 18 for final DNA construct). The doubly ligated product was PAGE purified before addition of Klenow DNA polymerase, SSB and nucleotides to allow extension from the Y-shaped adapter hairpin (SEQ ID NO: 31). To screen for successful DUO product a series of mismatch restriction sites were incorporated into the adapter sequences, whereby the enzyme will cut the analyte only if the restriction site has been successfully replicated by the DUO extension process.
Figure 24:
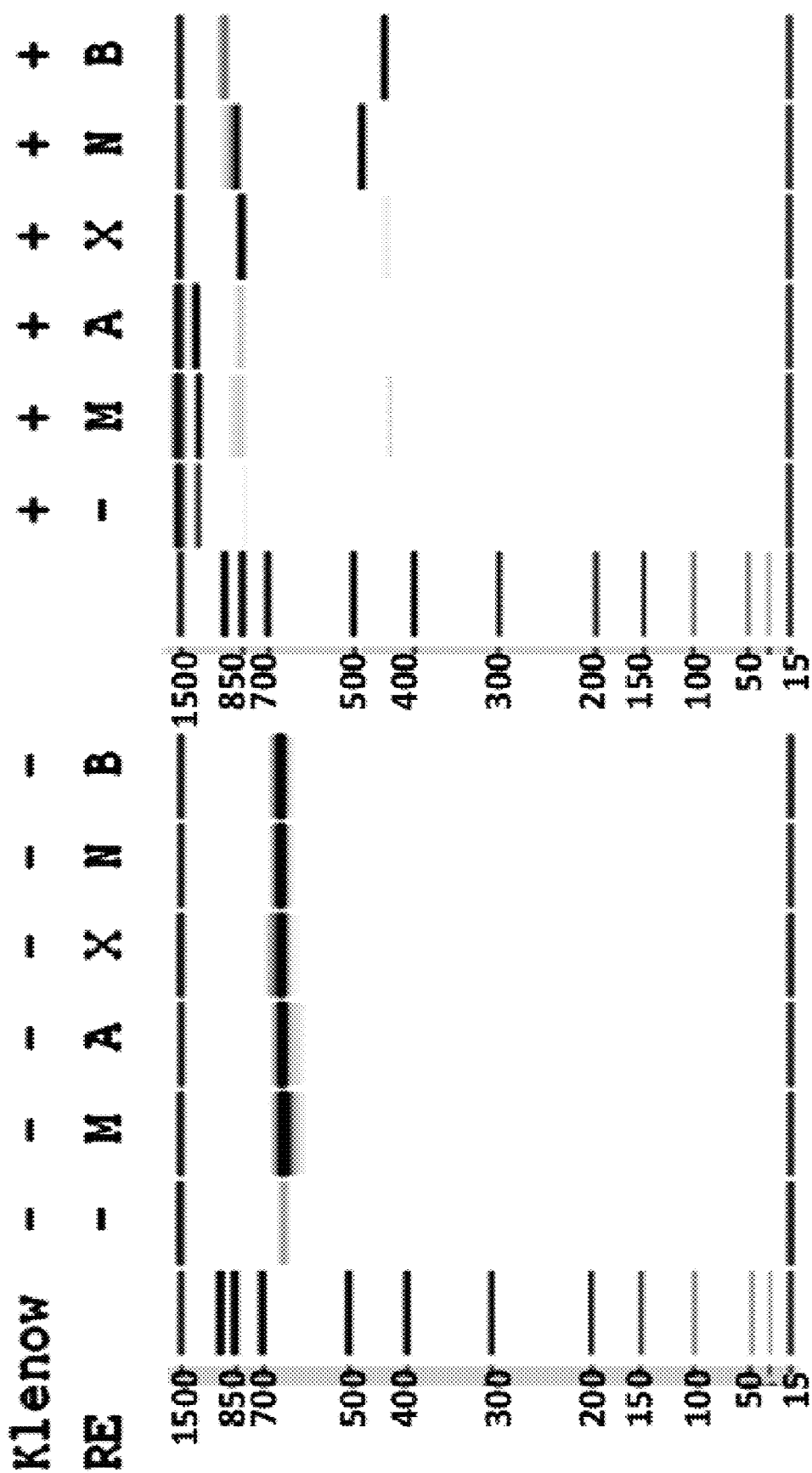
FIG. 24 shows that the adapter modified analyte (MONO, SEQ ID NOs: 29-35 connected as shown in FIG. 18) in the absence of polymerase does not digest with the restriction enzymes (see gel on the left, Key: M=MfeI, A=AgeI, X=XmaI, N=NgoMIV, B=BspEI), due to the fact they are mismatched to one another. However, on incubation with polymerase there is a noticeable size shift and the shifted product (DUO. SEQ ID NOs: 29-36 connected as shown in FIG. 25) now digests as expected with each of the restriction enzymes (see gel on the right, Key: M=MfeI, A=AgeI, X=XmaI, N=NgoMIV, B=BspEI).

FIG. 24 shows that the adapter modified analyte (MONO, SEQ ID NO: 29-35) in the absence of polymerase does not digest with the restriction enzymes (see gel on the left in FIG. 24, Key: M=MfeI, A=AgeI, X=XmaI, N=NgoMIV, B=BspEI), due to the fact they are mismatched to one another, as shown in FIG. 23 top. However, on incubation with polymerase there is a noticeable size shift and the shifted product (DUO) now digests as expected with each of the restriction enzymes (see gel on the right in FIG. 24, Key: M=MfeI, A=AgeI, X=XmaI, N=NgoMIV, B=BspEI). This shows that using the described method it is possible to produce DUO product (SEQ ID NOs: 29-36 connected as shown in FIG. 25).

Figure 25:
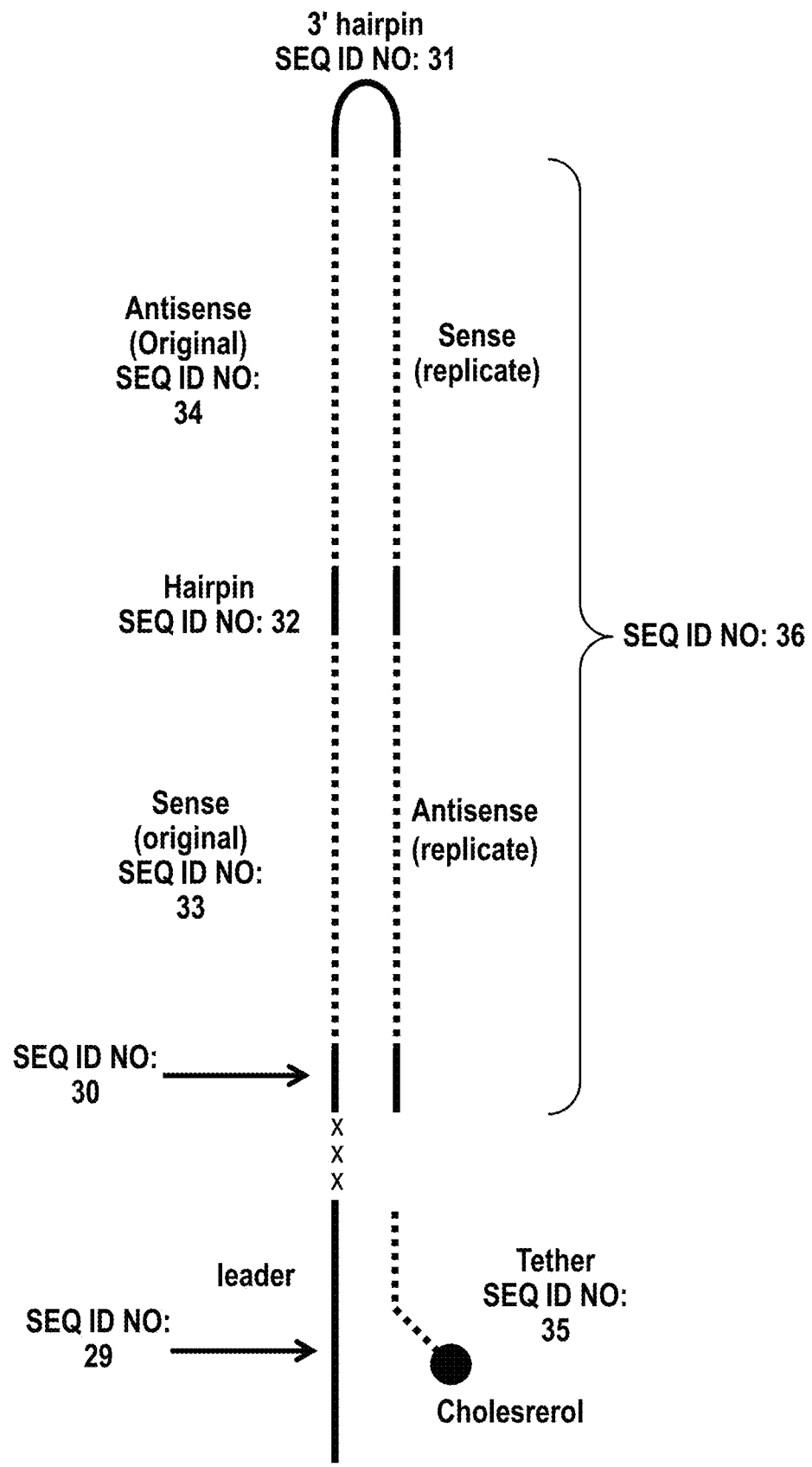
FIG. 25 shows the polynucleotide DUO hairpin construct (SEQ ID NOs: 29 to 36) used in Examples 6.

Reading around DUO hairpins constructs (SEQ ID NO's: 29-36 connected as shown in FIG. 25), which consist of original sense (SEQ ID NO: 33) and anti-sense strands (SEQ ID NO: 34) as well as replicate sense and replicate strands (SEQ ID NO: 36), using a helicase enzyme was investigated.

Methods: The DNA construct used in this experiment was produced by the method disclosed in Example 5 above.

MspA production: The MspA pore MS(B1-G75S-G77S-L88N-Q126R)8 MspA (SEQ ID NO: 2 with the mutations G75S/G77S/L88N/Q126R) was produced by the method described in Example 4.

Unzipping experiments—Electrical measurements were acquired, as described in Example 4, from single MspA nanopores (MS(B1-G75S-G77S-L88N-Q126R)8 MspA (SEQ ID NO: 2 with the mutations G75S/G77S/L88N/Q126R)) inserted in 1,2-diphytanoyl-glycero-3-phosphocholine lipid (Avanti Polar Lipids) bilayers in buffer solution (400 mM NaCl, 100 mM Hepes, 10 mM potassium ferrocyanide, 10 mM potassium ferricyanide, pH8.0) at an applied potential of +140 mV.

Initially, MgCl2 (10 mM) and dTTP (5 mM) were added to the cis compartment and a control experiment run for 5 mins. Secondly, the DNA construct (0.1 nN, SEQ ID NOs: 29-36 connected as shown in FIG. 25) was added to the cis compartment and a further control experiment run for 5 mins. Finally, the helicase (100 nM) was added to the electrophysiology chamber to initiate helicase activity. All unzipping experiments were carried out at a constant potential of +140 mV.

Figure 26:
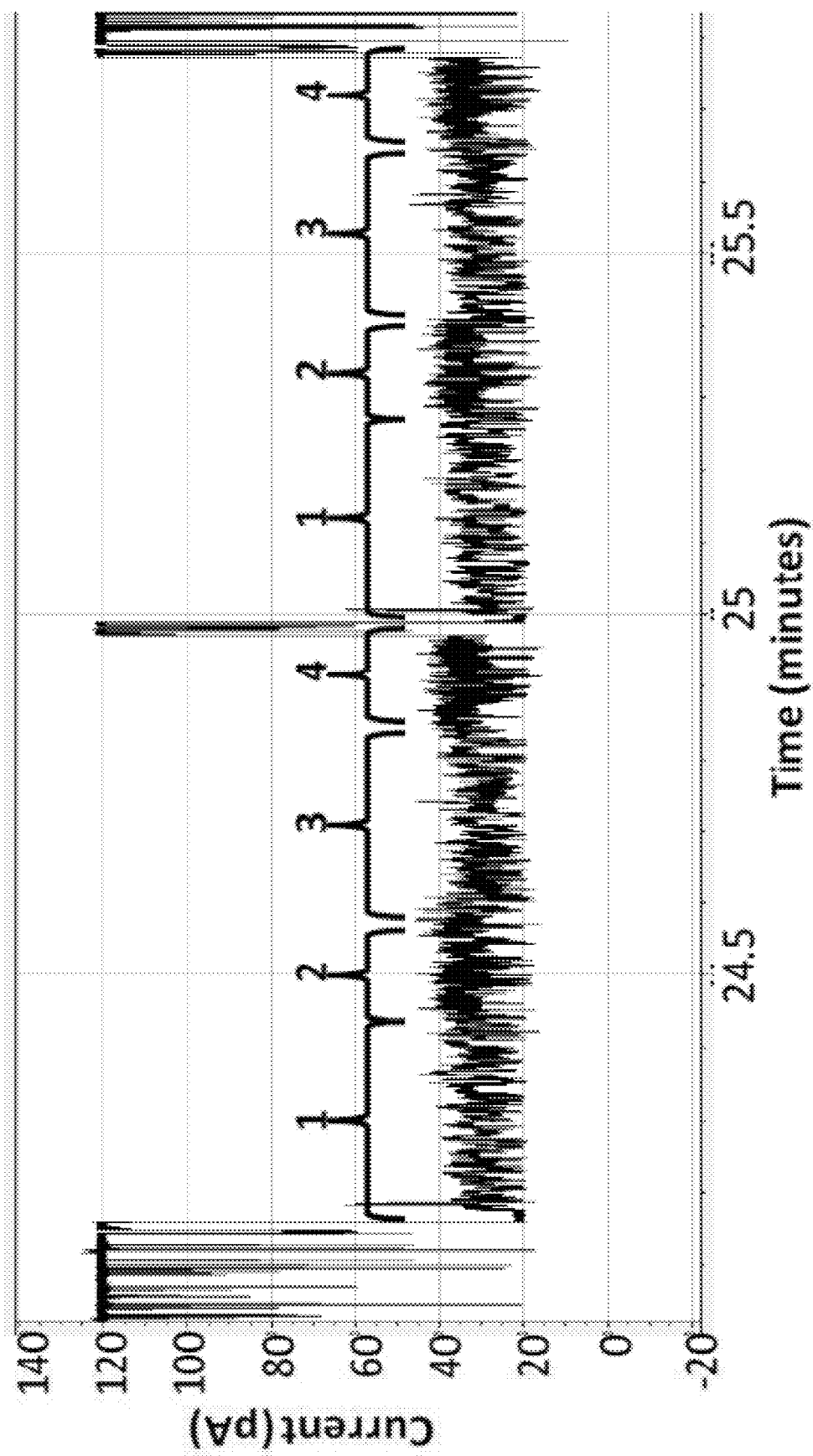
FIG. 26 shows two typical helicase controlled DNA movements for the DUO hairpin construct (SEQ ID NOs: 29 to 36 connected as shown in FIG. 25) through an MspA nanopore (MS(B1-G75S-G77S-L88N-Q126R)8 MspA (SEQ ID NO: 2 with the mutations G75S/G77S/L88N/Q126R)). Sense original=region 1. Anti-sense original=region 2. Sense replicate=region 3. Anti-sense replicate=region 4.
Figure 27:
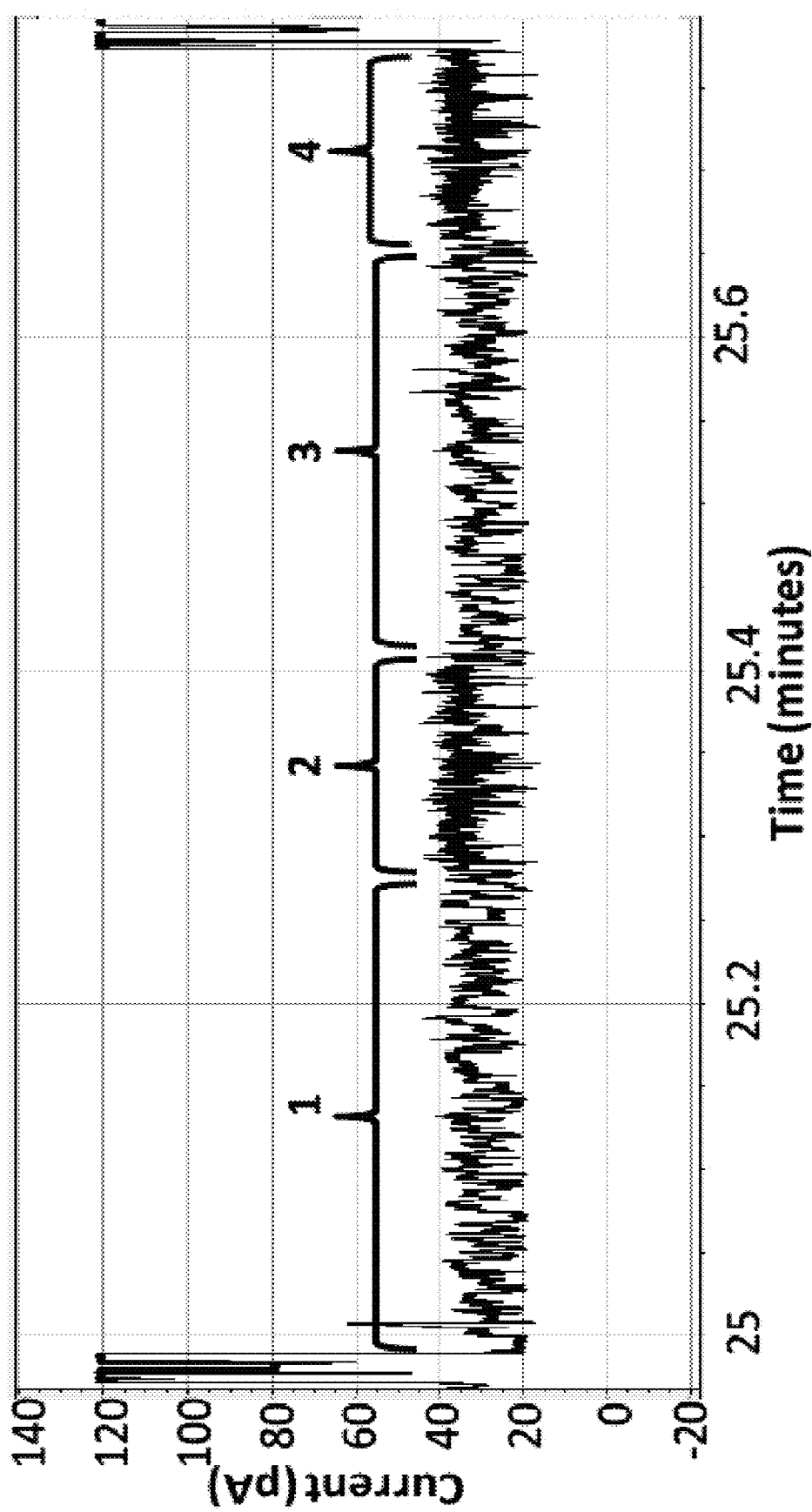
FIG. 27 shows an expanded view of a typical helicase controlled DNA movement for the DUO hairpin construct (SEQ ID NOs: 29 to 36 connected as shown in FIG. 25) through an MspA nanopore (MS(B1-G75S-G77S-L88N-Q126R)8 MspA (SEQ ID NO: 2 with the mutations G75S/G77S/L88N/Q126R)). Sense original=region 1. Anti-sense original=region 2. Sense replicate=region 3. Anti-sense replicate=region 4.
Figure 28:
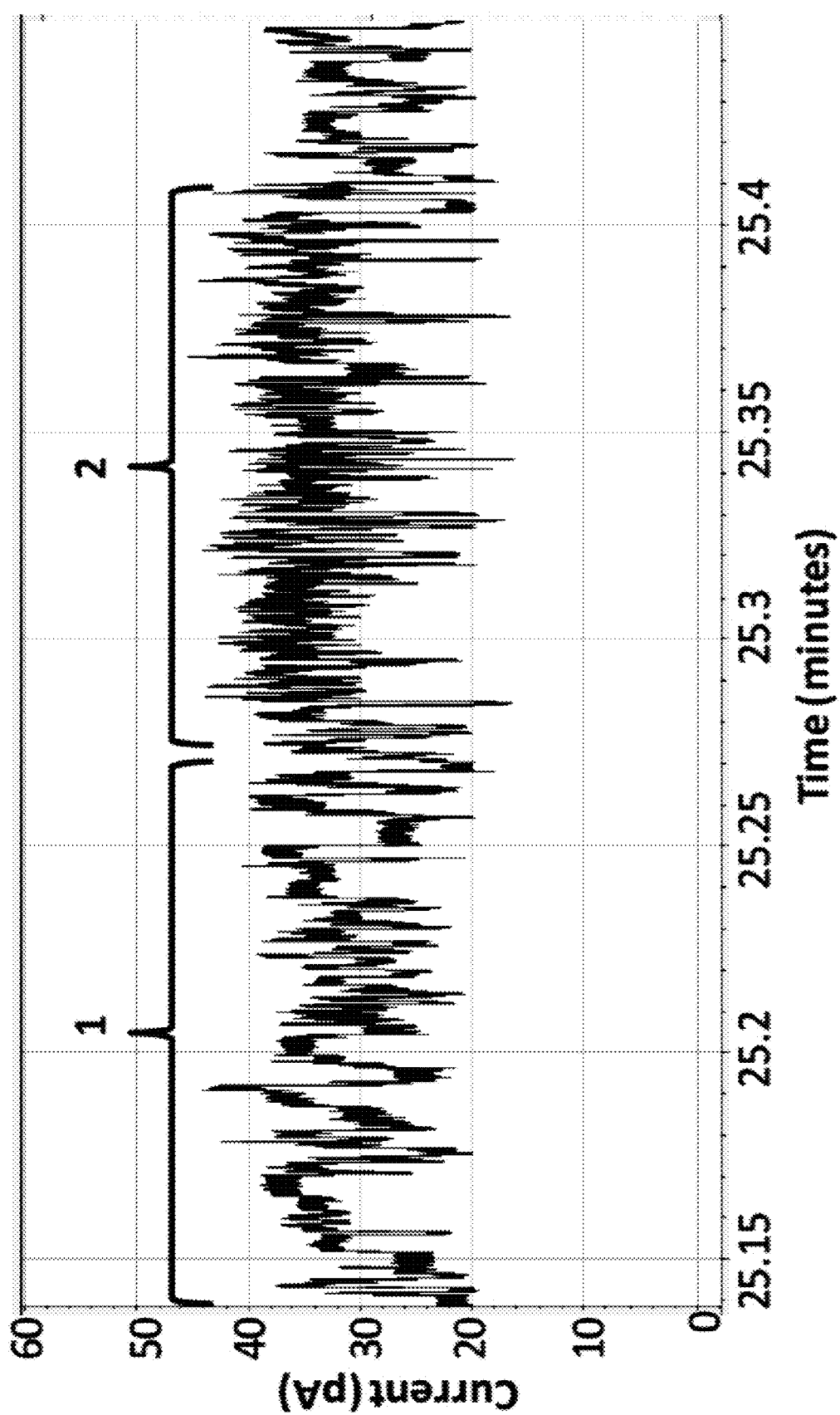
FIG. 28 shows an expanded view of a typical transition between the sense original and antisense original regions of the DUO hairpin construct (SEQ ID NOs: 29 to 36 connected as shown in FIG. 25) when under helicase controlled DNA movement through an MspA nanopore (MS(B1-G75S-G77S-L88N-Q126R)8 MspA (SEQ ID NO: 2 with the mutations G75S/G77S/L88N/Q126R)). Sense original=region 1. Anti-sense original=region 2.

Results:

The DUO hairpin construct (SEQ ID NOs: 29-36 connected as shown in FIG. 25) when added to an MspA nanopore (MS(B1-G75S-G77S-L88N-Q126R)8 MspA (SEQ ID NO: 2 with the mutations G75S/G77S/L88N/Q126R)) with a helicase resulted in unzipping of the DNA and helicase controlled DNA movement, with a large number of sequence dependent states (FIGS. 26 to 28). FIG. 26 shows two typical helicase controlled DNA movements, the regions which correspond to the original sense section, original antisense section, the replicate sense region and the replicate antisense sections are labeled 1 to 4 respectively. FIG. 27 shows a magnified view of one of the helicase controlled DNA movement from FIG. 26 and FIG. 28 shows another magnified view of the transition between the original sense and anti sense strands. The change in speed between the helicase controlling the movement of the sense strand in comparison to the antisense strand is clearly visible (FIGS. 26-28). This alteration in speed eliminates the need for markers to mark the hairpin turn. This demonstrates the ability to read around DUO hairpin constructs (SEQ ID NOs: 29-36 connected as shown in FIG. 25), and thus sequence both the sense and anti-sense strands of the dsDNA twice. This makes base-calling more accurate as one gets four chances to call a single position.

The invention claimed is:

1. A method comprising:
   (i) preparing a nucleic acid construct by ligating a polynucleotide bridging moiety to a 3' terminus of a first strand and a 5' terminus of a second strand of a double stranded nucleic acid, wherein the first strand of the double stranded nucleic acid comprises a first nucleic acid sequence and the second strand of the double stranded nucleic acid comprises a second nucleic acid sequence that is complementary to the first nucleic acid sequence;
   (ii) using a single molecule sequencing apparatus to perform a sequencing reaction that reads through the first strand, the bridging moiety, and the second strand to produce orthogonal proof-reading sequence information for a methylated nucleobase in the first strand of the construct, wherein the movement of the nucleic acid construct through the single molecule sequencing apparatus is controlled by a Phi29 DNA polymerase;
   (iii) comparing the sequence information between the first nucleic acid sequence and the second nucleic acid sequence; and
   (iv) determining the presence of a methylated nucleobase in the first sequence.

2. The method of claim 1, wherein the polynucleotide bridging moiety comprises a marker.

3. The method of claim 2, wherein the marker is an abasic DNA or a sequence specific nucleic acids.

4. The method of claim 2, wherein the method further comprising obtaining a signal from the marker in sequencing the bridging moiety that is indicative of the first strand having been sequenced.

5. The method of claim 1, wherein the Phi29 DNA polymerase is not chemically modified.

6. The method of claim 1, wherein the Phi29 DNA polymerase comprises an amino acid sequence at least 90% identical to SEQ ID NO: 6.

7. The method of claim 1, wherein the preparing comprises synthesizing a complement of the first sequence to produce the double stranded nucleic acid, wherein the complement contains nucleobases selected from adenine, guanine, thymine, uracil, and cytosine.

8. The method of claim 1, wherein the first nucleic acid sequence is present in a biological sample, wherein the biological sample is obtained or extracted from an organism or a microorganism.

9. The method of claim 1, wherein the bridging moiety is a hairpin loop.

10. The method of claim 9, wherein the hairpin loop is 4-100 nucleotides in length.

11. The method of claim 1, wherein the hairpin loop is 4-8 nucleotides in length.

12. The method of claim 1, wherein the first nucleic acid sequence is a DNA sequence.

13. The method of claim 1, wherein the methylated nucleobase is 5-methylcytosine, 5-hydroxymethylcytosine, or methylcytidine.

14. The method of claim 1, wherein the double-stranded nucleic acid comprises hemi-genomic DNA.

* * * * *

SEQUENCE LISTING

<160> NUMBER OF SEQ ID NOS: 37

<210> SEQ ID NO 1
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125
```

```
Ala Thr Phe Ser Val Arg Val Ser Gly Ala Lys Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
                180

<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaaactgc tagttattag aacaaaaggt    180
accattgctg gtcaatatag agtttatagc gaagaaggtg ctaacaaaag tggtttagcc     240
tggccttcag cctttaaggt acagttgcaa ctacctgata tgaagtagc tcaaatatct      300 gattactatc caagaaattc gattgataca aaaaactata tgagtacttt aacttatgga    360
ttcaacggta atgttactgg tgatgataca ggaaaaattg gcggcttat tggtgcaaat      420 gtttcgattg gtcatacact gaactatgtt caacctgatt tcaaaacaat tttagagagc    480
ccaactgata aaaagtaggg ctggaaagtg atatttaaca atggtgaa tcaaaattgg      540 ggaccatacg atcgagattc ttggaacccg gtatatggca atcacttttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa attaa                     885

<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
```

```
                        85                  90                  95
Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
            130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
            290

<210> SEQ ID NO 5
<211> LENGTH: 1830
<212> TYPE: DNA
<213> ORGANISM: bacteriophage phi AR29

<400> SEQUENCE: 5
atgaaacaca tgccgcgtaa aatgtatagc tgcgcgtttg aaaccacgac caaagtggaa      60
gattgtcgcg tttgggccta tggctacatg aacatcgaag atcattctga atacaaaatc     120
ggtaacagtc tggatgaatt tatggcatgg gtgctgaaaa ttcaggcgga tctgtacttc     180
cacaacctga aatttgatgg cgcattcatt atcaactggc tggaacgtaa tggctttaaa     240
tggagcgcgt atggtctgcc gaacacgtat aataccatta tctctcgtat gggccagtgg     300
tatatgattg atatctgcct gggctacaaa ggtaaacgca aaattcatac cgtgatctat     360
gatagcctga aaaactgccg gtttccggtg aagaaaattg cgaaagattt caaactgacg     420
gttctgaaag gcgatattga ttatcacaaa gaacgtccgg ttggttacaa aatcaccccg     480
gaagaatacg catacatcaa aaacgatatc cagatcatcg cagaagcgct gctgattcag     540
tttaaacagg gcctggatcg catgaccgcg ggcagtgata gcctgaaagg tttcaaagat     600
atcatcacga ccaaaaaatt caaaaaagtg ttcccgacgc tgagcctggg tctggataaa     660
gaagttcgtt atgcctaccg cggcggtttt acctggctga cgatcgtttc aaagaaaaaa     720
gaaattggcg agggtatggt gtttgatgtt aatagtctgt atccggcaca gatgtacagc     780
cgcctgctgc cgtatggcga accgatcgtg ttcgagggta aatatgtttg ggatgaagat     840
tacccgctgc atattcagca catccgttgt gaatttgaac tgaaagaagg ctatattccg     900
```

```
accattcaga tcaaacgtag tcgcttctat aagggtaacg aatacctgaa aagctctggc    960
ggtgaaatcg cggatctgtg gctgagtaac gtggatctgg aactgatgaa agaacactac   1020
gatctgtaca acgttgaata catcagcggc ctgaaattta agccacgac cggtctgttc    1080
aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccggatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg tgtggttct ggtggatgat acgtttacca ttaaatctgg cggtagtgcg    1740
tggagccatc cgcagttcga aaaaggcggt ggctctggtg gcggttctgg cggtagtgcc   1800
tggagccacc cgcagtttga aaataataa                                      1830
```

<210> SEQ ID NO 6
<211> LENGTH: 608
<212> TYPE: PRT
<213> ORGANISM: bacteriophage phi AR29

<400> SEQUENCE: 6

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

```
Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 7
<211> LENGTH: 184
<212> TYPE: PRT
```

<213> ORGANISM: Mycobacterium smegmatis

<400> SEQUENCE: 7

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 8
<211> LENGTH: 184
<212> TYPE: PRT
<213> ORGANISM: Mycobacterium smegmatis

<400> SEQUENCE: 8

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
```

Tyr Gly Glu Pro Trp Asn Met Asn
            180

<210> SEQ ID NO 9
<211> LENGTH: 183
<212> TYPE: PRT
<213> ORGANISM: Mycobacterium smegmatis

<400> SEQUENCE: 9

Val Asp Asn Gln Leu Ser Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 10
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 10
aaaaaaaaaa aa                                                       12

<210> SEQ ID NO 11
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(4)
<223> OTHER INFORMATION: n = i
<220> FEATURE:
<221> NAME/KEY: misc_feature
<222> LOCATION: (7)..(8)
<223> OTHER INFORMATION: n = i
<220> FEATURE:
<221> NAME/KEY: misc_feature
<222> LOCATION: (12)..(12)

<223> OTHER INFORMATION: n = i

<400> SEQUENCE: 11
tttnttnntt tn                                                          12

<210> SEQ ID NO 12
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(25)
<223> OTHER INFORMATION: n = abasic nucleotide

<400> SEQUENCE: 12
tttttttttt tttttttttt nnnnntgtac tgccgtacgt aaaaaaatag ctgatcgtac      60
ttactagcat gtt                                                         73

<210> SEQ ID NO 13
<211> LENGTH: 99
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(25)
<223> OTHER INFORMATION: n = abasic nucleotide

<400> SEQUENCE: 13
tttttttttt tttttttttt nnnnntgtac tgccgtacgt aaaaaaatag ctgatcgtac      60
ttacatgacg gcatgcattt ttttatcgac tagcatgtt                             99

<210> SEQ ID NO 14
<211> LENGTH: 99
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(25)
<223> OTHER INFORMATION: n = abasic nucleotide
<220> FEATURE:
<221> NAME/KEY: misc_feature
<222> LOCATION: (64)..(64)
<223> OTHER INFORMATION: n = i
<220> FEATURE:
<221> NAME/KEY: misc_feature
<222> LOCATION: (67)..(67)
<223> OTHER INFORMATION: n = i
<220> FEATURE:
<221> NAME/KEY: misc_feature
<222> LOCATION: (71)..(71)
<223> OTHER INFORMATION: n = i
<220> FEATURE:
<221> NAME/KEY: misc_feature
<222> LOCATION: (76)..(76)
<223> OTHER INFORMATION: n = i
<220> FEATURE:
<221> NAME/KEY: misc_feature
<222> LOCATION: (80)..(80)
<223> OTHER INFORMATION: n = i
<220> FEATURE:
<221> NAME/KEY: misc_feature
<222> LOCATION: (83)..(83)
<223> OTHER INFORMATION: n = i
<220> FEATURE:
<221> NAME/KEY: misc_feature
<222> LOCATION: (87)..(87)
<223> OTHER INFORMATION: n = i

<400> SEQUENCE: 14 ttttttttttt tttttttttt nnnnntgtac tgccgtacgt aaaaaaatag ctgatcgtac      60
ttanatnacg ncatgnattn ttntatngac tagcatgtt                              99

<210> SEQ ID NO 15
<211> LENGTH: 99
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (21)..(25)
<223> OTHER INFORMATION: n = abasic nucleotide
<220> FEATURE:
<221> NAME/KEY: misc_feature
<222> LOCATION: (66)..(66)
<223> OTHER INFORMATION: n = deoxyuridine
<220> FEATURE:
<221> NAME/KEY: misc_feature
<222> LOCATION: (78)..(78)
<223> OTHER INFORMATION: n = deoxyuridine
<220> FEATURE:
<221> NAME/KEY: misc_feature
<222> LOCATION: (82)..(82)
<223> OTHER INFORMATION: n = deoxyuridine

<400> SEQUENCE: 15 ttttttttttt tttttttttt nnnnntgtac tgccgtacgt aaaaaaatag ctgatcgtac      60
ttacangacg gcatgcantt tyttatcgac tagcatgtt                              99

<210> SEQ ID NO 16
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 16
cccccccccc ccccaccccc cccccccccc ccccctattc tgtttatgtt tcttgtttgt      60
tagccttttg gctaacaaac aagaaacata aacagaatag                            100

<210> SEQ ID NO 17
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 17
cccccccccc ccccaccccc cccccccccc ccccctattc tgtttatgtt tcttgtttgt      60
tagcc                                                                  65

<210> SEQ ID NO 18
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 18
ggctaacaaa caagaaacat aaacagaata g                                     31

<210> SEQ ID NO 19
<211> LENGTH: 125
<212> TYPE: DNA
<213> ORGANISM: Artificial Sequence
<220> FEATURE:
<223> OTHER INFORMATION: Synthetic polynucleotide

<400> SEQUENCE: 19
cccccccccc ccccaccccc cccccccccc cccctattc tgtttatgtt tcttgtttgt    60 tagcctttg gctaacaaac aagaaacata aacagaatag cccccccccc tcagatctca   120
ctatc                                                              125

<210> SEQ ID NO 20
<211> LENGTH: 101
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (68)..(68)
<223> OTHER INFORMATION: n = abasic nucleotide

<400> SEQUENCE: 20
cccccccccc ccccaccccc cccccccccc cccctattc tgtttatgtt tcttgtttgt    60
tagccttntt ggctaacaaa caagaaacat aaacagaata g                      101

<210> SEQ ID NO 21
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 21
tttttttttt ggcgccctgc cgtttctgat aagttgctt                          39

<210> SEQ ID NO 22
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 22
aaaaaaaaaa acgcgtaaac ctgctgttgc ttggaaag                           38

<210> SEQ ID NO 23
<211> LENGTH: 95
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (51)..(54)
<223> OTHER INFORMATION: n = abasic nucleotide

<400> SEQUENCE: 23
tttttttttt tttttttttt tttttttttt tttttttttt tttttttttt nnnntttttt    60
ttttggctaa caaacaagaa acataaacag aatag                              95

<210> SEQ ID NO 24
<211> LENGTH: 76

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(45)
<223> OTHER INFORMATION: n = abasic nucleotide

<400> SEQUENCE: 24
gcgcctattc tgtttatgtt tcttgtttgt tagccttttt tnnnnttttt tttttttttt      60
tttttttttt tttttt                                                    76

<210> SEQ ID NO 25
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(39)
<223> OTHER INFORMATION: n = abasic nucleotide

<400> SEQUENCE: 25
cgcgctattc tgtttatgtt tcttgtttgt tagccnnnng gctaacaaac aagaaacata      60
aacagaatag                                                           70

<210> SEQ ID NO 26
<211> LENGTH: 1051
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (51)..(54)
<223> OTHER INFORMATION: n = abasic nucleotide
<220> FEATURE:
<221> NAME/KEY: misc_feature
<222> LOCATION: (536)..(539)
<223> OTHER INFORMATION: n = abasic nucleotide
<220> FEATURE:
<221> NAME/KEY: misc_feature
<222> LOCATION: (1017)..(1020)
<223> OTHER INFORMATION: n = abasic nucleotide

<400> SEQUENCE: 26
tttttttttt tttttttttt tttttttttt tttttttttt tttttttttt nnnnttttttt    60 ttttggctaa caaacaagaa acataaacag aataggcgcc ctgccgtttc tgataagttg     120
cttgatttgg ttggacttgg tggcaagtct gccgctgata aggaaagga tactcgtgat     180 tatcttgctg ctgcatttcc tgagcttaat gcttgggagc gtgctggtgc tgatgcttcc     240
tctgctggta tggttgacgc cggatttgag aatcaaaaag agcttactaa aatgcaactg     300
gacaatcaga aagagattgc cgagatgcaa aatgagactc aaaagagat tgctggcatt     360 cagtcggcga cttcacgcca gaatacgaaa gaccaggtat atgcacaaaa tgagatgctt     420
gcttatcaac agaaggagtc tactgctcgc gttgcgtcta ttatggaaaa caccaatctt     480
tccaagcaac agcaggttta cgcgctattc tgtttatgtt tcttgtttgt tagccnnnng    540
gctaacaaac aagaaacata aacagaatag cgcgtaaacc tgctgttgct tggaaagatt    600
ggtgttttcc ataatagacg caacgcgagc agtagactcc ttctgttgat aagcaagcat    660 ctcatttttgt gcatataccct ggtctttcgt attctggcgt gaagtcgccg actgaatgcc    720
```

| | |
|---|---|
| agcaatctct ttttgagtct cattttgcat ctcggcaatc tctttctgat tgtccagttg | 780 |
| cattttagta agctctttt gattctcaaa tccggcgtca accataccag cagaggaagc | 840 |
| atcagcacca gcacgctccc aagcattaag ctcaggaaat gcagcagcaa gataatcacg | 900 |
| agtatccttt cctttatcag cggcagactt gccaccaagt ccaaccaaat caagcaactt | 960 |
| atcagaaacg gcagggcgcc tattctgttt atgtttcttg tttgttagcc ttttttnnnn | 1020 |
| tttttttttt tttttttttt tttttttttt t | 1051 |

<210> SEQ ID NO 27
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 27

| | |
|---|---|
| tttttttttt accggtggta ccttggttgt ttctgttggt gctgatat | 48 |

<210> SEQ ID NO 28
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 28

| | |
|---|---|
| tttttttttt accggtgagc tcgaccgcct ccaaacaatt tag | 43 |

<210> SEQ ID NO 29
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 29

| | |
|---|---|
| tttttttttt tttttttttt tttttttttt tttttttttt tttttttttt tctgttggtg | 60 |
| ctgatattgc | 70 |

<210> SEQ ID NO 30
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 30

| | |
|---|---|
| gtttctgtcc cgggcttttg atgtac | 26 |

<210> SEQ ID NO 31
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 31

| | |
|---|---|
| atcaaaagac cggtacagaa accaattgga tcggaagagc ggttttacc gctcttccga | 60 |
| tc | 62 |

<210> SEQ ID NO 32
<211> LENGTH: 78

```
<212> TYPE: DNA
<213> ORGANISM: Artificial Sequence
<220> FEATURE:
<223> OTHER INFORMATION: Synthetic polynucleotide

<400> SEQUENCE: 32
cggttgtttc tgtgccggcc gatattgctt ttgattttta tcaaaagcaa tatcgtccgg      60
aacagaaaca accgagct                                                    78

<210> SEQ ID NO 33
<211> LENGTH: 408
<212> TYPE: DNA
<213> ORGANISM: Artificial Sequence
<220> FEATURE:
<223> OTHER INFORMATION: Synthetic polynucleotide

<400> SEQUENCE: 33
cttggttgtt tctgttggtg ctgatattgc ttttgatgcc gaccctaaat ttttgcctg       60 tttggttcgc tttgagtctt cttcggttcc gactaccctc ccgactgcct atgatgttta    120
tcctttgaat ggtcgccatg atggtggtta ttataccgtc aaggactgtg tgactattga    180
cgtccttccc cgtacgccgg gcaataacgt ttatgttggt ttcatggttt ggtctaactt    240
taccgctact aaatgccgcg gattggtttc gctgaatcag gttattaaag agattatttg    300
tctccagcca cttaagtgag gtgatttatg tttggtgcta ttgctggcgg tattgcttct    360
gctcttgctg gtggcgccat gtctaaattg tttggaggcg gtcgagct                 408

<210> SEQ ID NO 34
<211> LENGTH: 408
<212> TYPE: DNA
<213> ORGANISM: Artificial Sequence
<220> FEATURE:
<223> OTHER INFORMATION: Synthetic polynucleotide

<400> SEQUENCE: 34
cgaccgcctc caaacaattt agacatggcg ccaccagcaa gagcagaagc aataccgcca      60
gcaatagcac caaacataaa tcacctcact taagtggctg gagacaaata atctctttaa    120
taacctgatt cagcgaaacc aatccgcggc atttagtagc ggtaaagtta gaccaaacca    180
tgaaaccaac ataaacgtta ttgcccggcg tacggggaag gacgtcaata gtcacacagt    240
ccttgacggt ataataacca ccatcatggc gaccattcaa aggataaaca tcataggcag    300
tcgggagggt agtcggaacc gaagaagact caaagcgaac caaacaggca aaaaatttag    360
ggtcggcatc aaaagcaata tcagcaccaa cagaaacaac caaggtac                 408

<210> SEQ ID NO 35
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 35
gcaatatcag caccaacaga aacaaccctt                                       29

<210> SEQ ID NO 36
<211> LENGTH: 948
<212> TYPE: DNA
<213> ORGANISM: Artificial Sequence
<220> FEATURE:
<223> OTHER INFORMATION: Synthetic polynucleotide
```

```
<400> SEQUENCE: 36
caattggttt ctgtaccggt cttttgatgt accttggttg tttctgttgg tgctgatatt      60
gcttttgatg ccgaccctaa atttttgcc tgtttggttc gctttgagtc ttcttcggtt      120
ccgactaccc tcccgactgc ctatgatgtt tatcctttga atggtcgcca tgatggtggt     180
tattataccg tcaaggactg tgtgactatt gacgtccttc cccgtacgcc gggcaataac     240
gtttatgttg gtttcatggt ttggtctaac tttaccgcta ctaaatgccg cggattggtt     300
tcgctgaatc aggttattaa agagattatt tgtctccagc cacttaagtg aggtgattta     360
tgtttggtgc tattgctggc ggtattgctt ctgctcttgc tggtggcgcc atgtctaaat     420
tgtttggagg cggtcgagct cggttgtttc tgttccggac gatattgctt ttgataaaaa     480
tcaaaagcaa tatcgccgg cacagaaaca accgagctcg accgcctcca aacaatttag      540
acatggcgcc accagcaaga gcagaagcaa taccgccagc aatagcacca aacataaatc     600
acctcactta agtggctgga gacaaataat ctctttaata acctgattca gcgaaaccaa     660
tccgcggcat ttagtagcgg taaagttaga ccaaaccatg aaaccaacat aaacgttatt     720
gcccggcgta cggggaagga cgtcaatagt cacacagtcc ttgacggtat aataaccacc     780
atcatggcga ccattcaaag gataaacatc ataggcagtc gggagggtag tcggaaccga     840
agaagactca aagcgaacca aacaggcaaa aaatttaggg tcggcatcaa aagcaatatc     900
agcaccaaca gaaacaacca aggtacatca aaagcccggg acagaaac                  948

<210> SEQ ID NO 37
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 37 cccctattc tgtttatgtt tcttgtttgt tagccttttg gctaacaaac aagaaacata      60
aacagaatag ccc                                                       73
```